(12) United States Patent
Solotoff

(10) Patent No.: US 12,144,756 B1
(45) Date of Patent: Nov. 19, 2024

(54) COMPRESSION GARMENTS

(71) Applicant: PREFERRED PRESCRIPTIONS, INC., Hollywood, FL (US)

(72) Inventor: Brandon Solotoff, Boca Raton, FL (US)

(73) Assignee: Preferred Prescription, INC., Hollywood, FL (US)

( * ) Notice: Subject to any disclaimer, the term of this patent is extended or adjusted under 35 U.S.C. 154(b) by 187 days.

(21) Appl. No.: 17/472,261

(22) Filed: Sep. 10, 2021

Related U.S. Application Data

(63) Continuation-in-part of application No. 17/020,072, filed on Sep. 14, 2020, now Pat. No. 11,839,570, (Continued)

(51) Int. Cl.
| | |
|---|---|
| *A61F 5/01* | (2006.01) |
| *A61F 7/00* | (2006.01) |
| *A61F 7/08* | (2006.01) |

(52) U.S. Cl.
CPC .......... *A61F 5/0118* (2013.01); *A61F 5/0109* (2013.01); *A61F 7/08* (2013.01);
(Continued)

(58) Field of Classification Search
CPC .. A61F 5/00; A61F 5/01; A61F 5/0102; A61F 5/0104; A61F 5/0106;
(Continued)

(56) References Cited

U.S. PATENT DOCUMENTS

| | | | |
|---|---|---|---|
| 2,573,791 A | 11/1951 | Howells | |
| 2,715,315 A | 8/1955 | Giardini | |

(Continued)

FOREIGN PATENT DOCUMENTS

| | | |
|---|---|---|
| CN | 102711683 B | 10/2012 |
| DE | 102006016988 A1 | 10/2007 |

(Continued)

OTHER PUBLICATIONS

Gonfalon: shapes, options, & accessories, Feb. 13, 2019, [online], [retrieved on Aug. 22, 2023]. Retrieved from the internet <URL: https://www.accentbanner.com/blog/gonfalon-shapes-options-accessories (Year: 2019).*

(Continued)

*Primary Examiner* — Ophelia A Hawthorne
*Assistant Examiner* — Gina McCarthy
(74) *Attorney, Agent, or Firm* — Thomas A. O'Rourke; James Bongiorno; O'Rourke IP Law PLLC

(57) ABSTRACT

A wrist brace includes a sleeve with a primary layer formed of elastic material that applies a first level of compression, and extends beyond the wrist onto the hand of the wearer, and onto at least a portion of the forearm of the wearer. A first opening and pocket in the sleeve receive a first correspondingly sized/shaped thermal pack, having a width formed to overlie the tendons of the third, fourth, and fifth compartments when the brace is worn. A second opening and second pocket in the sleeve receive a second correspondingly sized/shaped thermal pack having a width formed to overlie the tendons of the first and second compartments when the brace is worn. The sleeve has a particularly shaped layer(s) of high compression material that overlies and applies a second, higher level of compression to the thermal packs contained in the first and second pockets, and seals the openings.

8 Claims, 103 Drawing Sheets

(6 of 103 Drawing Sheet(s) Filed in Color)

Related U.S. Application Data which is a continuation-in-part of application No. 17/008,734, filed on Sep. 1, 2020, now Pat. No. 11,839,243.

(60) Provisional application No. 63/076,501, filed on Sep. 10, 2020, provisional application No. 62/911,495, filed on Oct. 7, 2019, provisional application No. 62/934,587, filed on Nov. 13, 2019, provisional application No. 62/934,591, filed on Nov. 13, 2019, provisional application No. 62/899,277, filed on Sep. 12, 2019.

(52) U.S. Cl.
CPC ..... *A61F 5/0111* (2013.01); *A61F 2007/0032* (2013.01); *A61F 2007/0035* (2013.01); *A61F 2007/0042* (2013.01); *A61F 2007/0043* (2013.01); *A61F 2007/0044* (2013.01)

(58) Field of Classification Search
CPC .... A61F 5/0109; A61F 5/0111; A61F 5/0118; A61F 5/0123; A61F 7/00; A61F 7/02; A61F 7/08; A61F 2007/00; A61F 2007/0001; A61F 2007/0039; A61F 2007/035; A61F 2007/108; A61F 2007/0042; A61F 2007/0043; A61F 2007/0044; A61F 2007/0225; A61F 2007/023; A61F 2007/0233; A61F 2007/0238; A61F 2013/00187; A61F 2013/00093; A61F 13/00; A61F 13/064; A61F 13/06; A61F 13/061; A61F 13/066; A61F 13/08; A41D 27/00; A41D 27/20; A41D 27/201; A41D 27/202; A41D 13/0051; A61H 9/005

See application file for complete search history.

(56) References Cited

U.S. PATENT DOCUMENTS

| | | | |
|---|---|---|---|
| 3,175,558 A | | 3/1965 | Caillouette |
| 3,327,703 A | | 6/1967 | Gamm |
| 3,900,035 A | | 8/1975 | Welch |
| 4,055,188 A | | 10/1977 | Pelton |
| 4,092,982 A | | 6/1978 | Salem |
| 4,201,203 A | * | 5/1980 | Applegate ............ A61F 5/0109 2/24 |
| 4,625,729 A | | 12/1986 | Roney |
| 4,669,476 A | | 6/1987 | Gordon |
| 4,800,867 A | | 1/1989 | Owens |
| 4,938,222 A | | 7/1990 | Bier |
| 4,964,402 A | | 10/1990 | Grim |
| 5,000,176 A | | 3/1991 | Daniel |
| 5,111,810 A | | 5/1992 | Fortney |
| 5,165,402 A | | 11/1992 | McCoy |
| 5,407,421 A | | 4/1995 | Goldsmith |
| 5,415,624 A | * | 5/1995 | Williams ............ A61F 7/02 602/14 |
| 5,483,703 A | | 1/1996 | Williams |
| 5,496,358 A | | 3/1996 | Rosenwald |
| 5,826,273 A | | 10/1998 | Eckes |
| 5,873,903 A | | 2/1999 | Garcia |
| 5,935,157 A | | 8/1999 | Harmon |
| 5,937,442 A | | 8/1999 | Yamaguchi |
| 6,001,122 A | | 12/1999 | Lyles |
| 6,173,589 B1 | | 1/2001 | Hayes |
| 6,440,094 B1 | | 8/2002 | Maas |
| 6,440,159 B1 | | 8/2002 | Edwards |
| 6,582,383 B2 | | 6/2003 | Horning |
| 6,589,272 B1 | | 7/2003 | Sheikh |
| 6,598,235 B2 | * | 7/2003 | Bulla ............ A41D 13/0051 2/69 |
| 6,617,485 B2 | | 9/2003 | Herzberg |
| 6,652,474 B1 | | 11/2003 | Quinn |
| 6,656,210 B1 | | 12/2003 | Plewes |
| 6,973,742 B2 | | 12/2005 | Gordon |
| 7,060,086 B2 | | 6/2006 | Wilson |
| 7,481,786 B2 | | 1/2009 | Flick |
| 7,871,388 B2 | | 1/2011 | Brown |
| 8,172,782 B2 | | 5/2012 | Rock |
| 8,220,074 B2 | | 7/2012 | Sutker |
| 8,231,816 B2 | | 7/2012 | Kingsford |
| 8,256,034 B2 | | 9/2012 | Berner |
| 8,454,545 B1 | | 6/2013 | Weber |
| 8,603,151 B2 | | 12/2013 | Latham |
| 8,827,767 B2 | | 9/2014 | Samoodi |
| 8,876,875 B1 | | 11/2014 | Nilforushan |
| 9,167,854 B2 | | 10/2015 | Levian |
| D818,138 S | | 5/2018 | Nicosia |
| 10,555,863 B2 | | 2/2020 | Hall |
| 2003/0195439 A1 | | 10/2003 | Caselnova |
| 2004/0158283 A1 | | 8/2004 | Shook |
| 2006/0218692 A1 | | 10/2006 | Lamarque |
| 2007/0100264 A1 | | 5/2007 | Hanson |
| 2007/0179421 A1 | * | 8/2007 | Farrow ............ A61H 9/005 601/151 |
| 2007/0299489 A1 | | 12/2007 | Francis |
| 2008/0125842 A1 | | 5/2008 | Petit |
| 2009/0062704 A1 | | 3/2009 | Brown |
| 2009/0125086 A1 | | 5/2009 | Juta |
| 2011/0224762 A1 | | 9/2011 | Gruber |
| 2012/0023782 A1 | | 2/2012 | Zaragosa |
| 2012/0078147 A1 | | 3/2012 | Ogulnick |
| 2014/0316314 A1 | | 10/2014 | Schubert |
| 2015/0119775 A1 | | 4/2015 | Gildersleeve |
| 2016/0228298 A1 | | 8/2016 | Geller |
| 2017/0367868 A1 | | 12/2017 | Ducharme |
| 2018/0055686 A1 | | 3/2018 | Munoz |

FOREIGN PATENT DOCUMENTS

| | | |
|---|---|---|
| WO | WO2006048619 A1 | 5/2006 |
| WO | WO2008077112 A2 | 6/2008 |
| WO | WO2011140487 A2 | 11/2011 |

OTHER PUBLICATIONS

How Do I Select the Right Size Brace? [retrieved on Aug. 22, 2023]. Retrieved from the Internet <URL:https://www.podactive.com/sizing-guide/ (Year: 2023).*

Lijing Wang, Martin Felder, Jackie Cai; "Study of Properties of Medical Compression Fabrics," J. of Fiber Bioengineering & Informatics, Global Science Press, p. 15-22 (2011).

Ying Xiong, Xiaoming Tao; "Compression Garments for Medical Therapy and Sports," Polymers, vol. 10, No. 663, 3-19, Jun. 14, 2018.

Li Z, Malengier B, Vasile S, Cools J, Van Langenhove L; "From 3d Scan to Body Pressure of Compression Garments," AUTEX2019—19th World Textile Conf., Jun. 11-15, 2019, Beljium.

Hugo Partsch, "Physics of Compression," , Published by Guset User, Nov. 24, 2015.

Dennis-Peter Born, Billy Sperlich, Hans-Christer Holmberg; "Bringing Light Into the Dark: Effects of Compression Clothing on Performance and Recovery,".

International Journal of Sports Physiology and Performance, 2013, 8:4-18 (2013).

Janwantanakuk, Prawit; "Cold pack/skin interface temperature during ince treatment with various levels of compression,". www.sciencedirect.com/science/article/abs/pii/S0031940606000824; 0vol. 92, Issue 4, Dec. 2006, pp. 254-259.

* cited by examiner

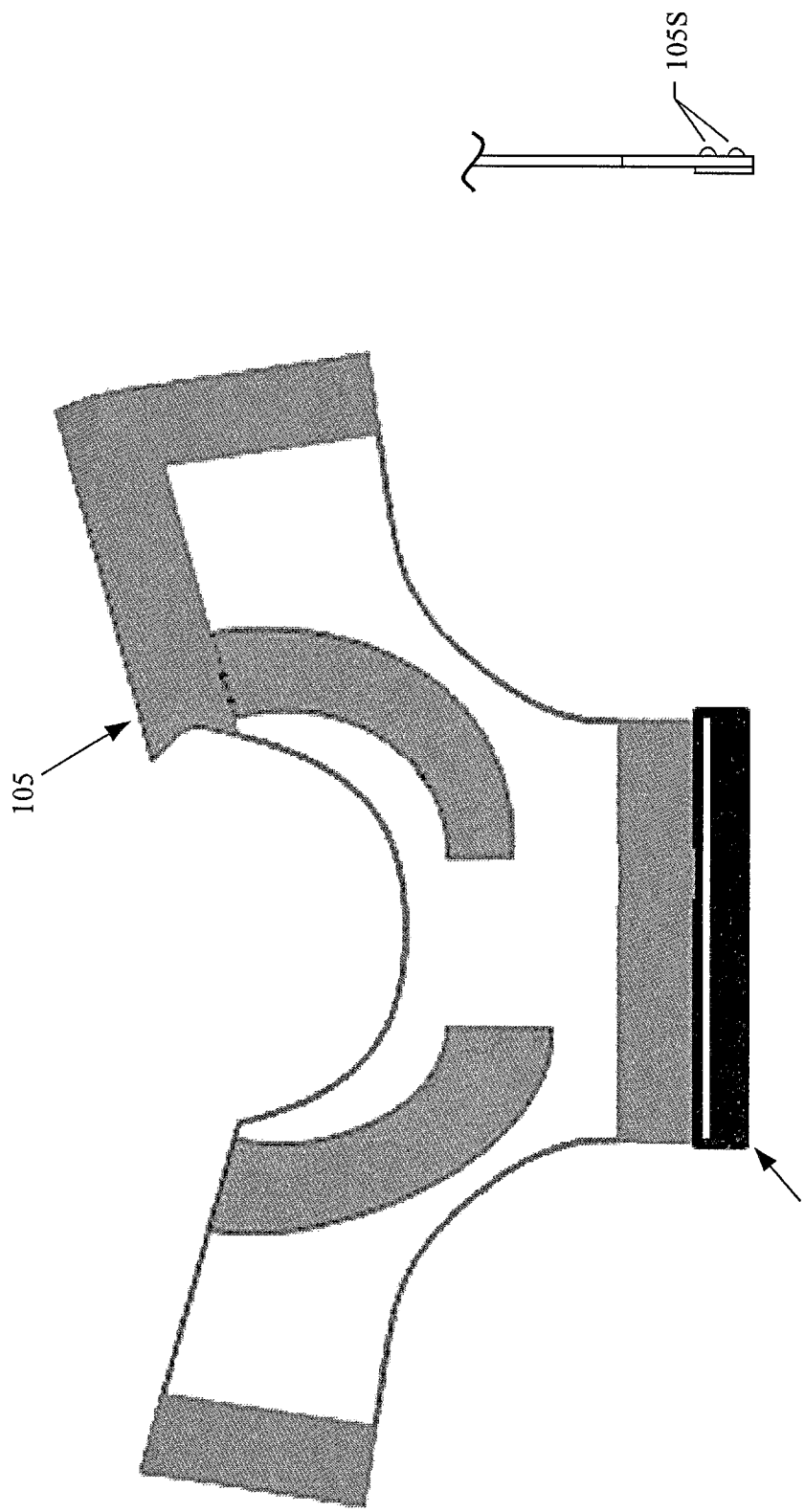

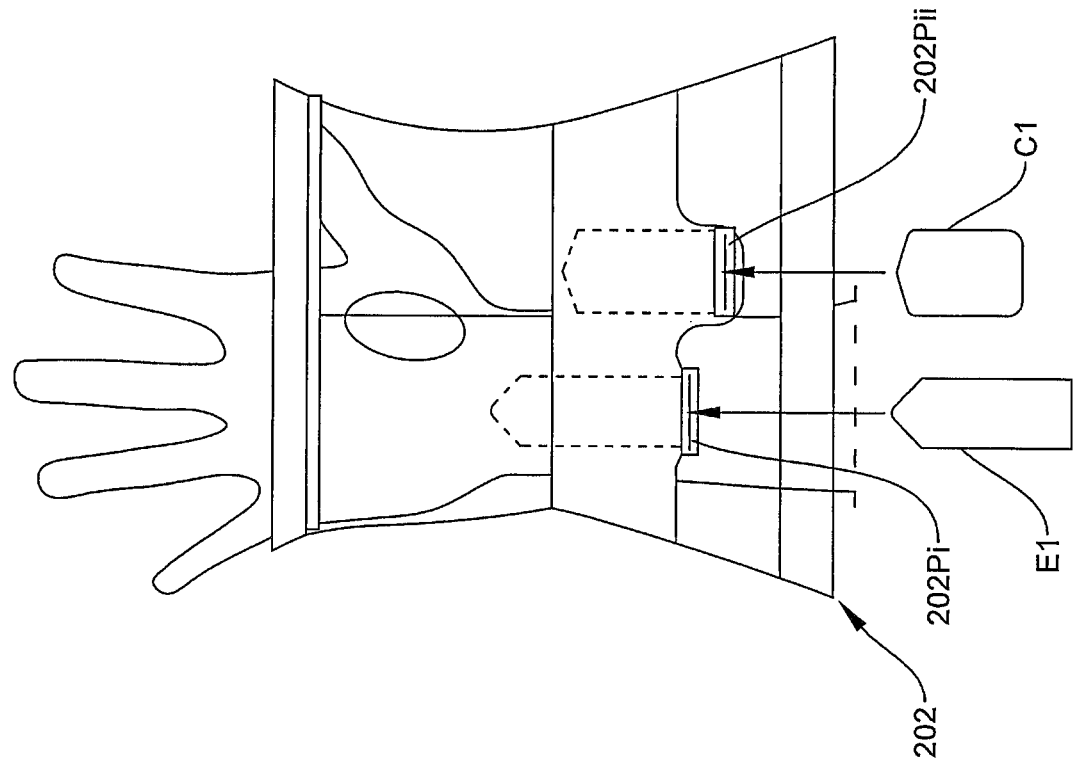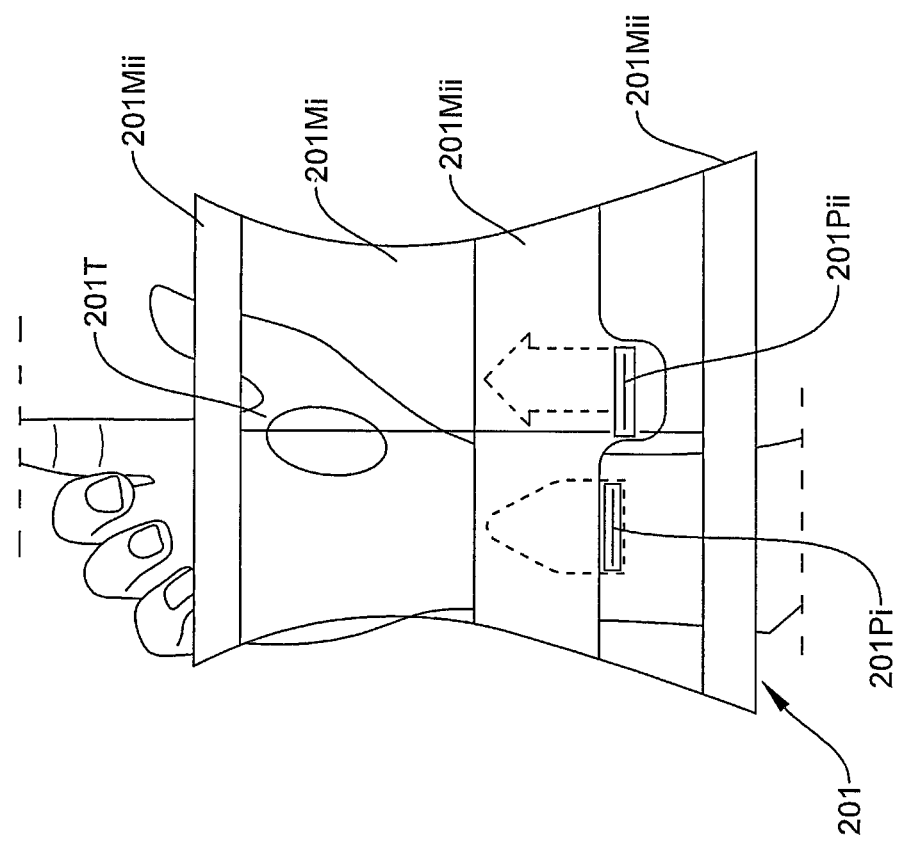
FIG. 15A
FIG. 15B

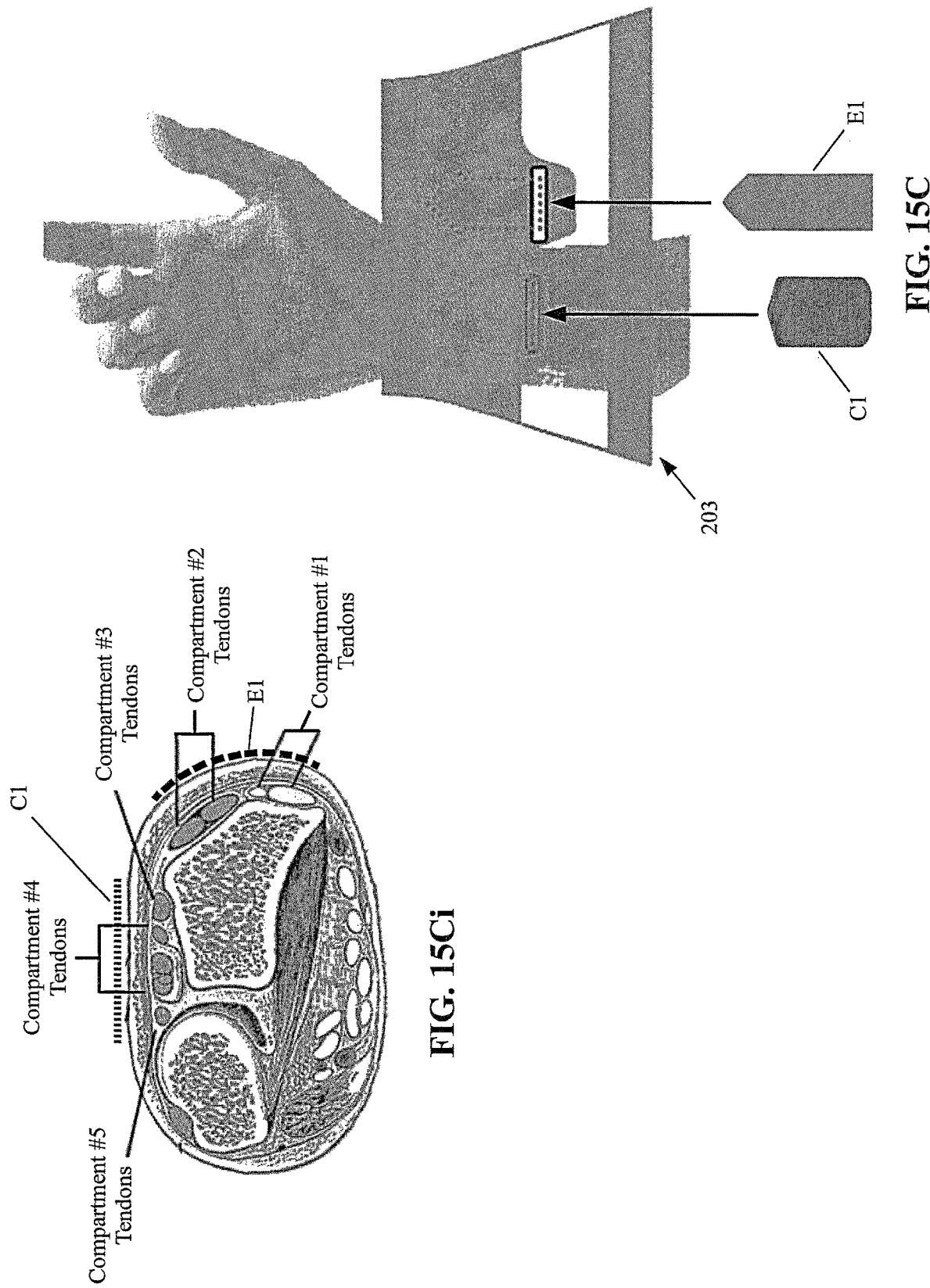

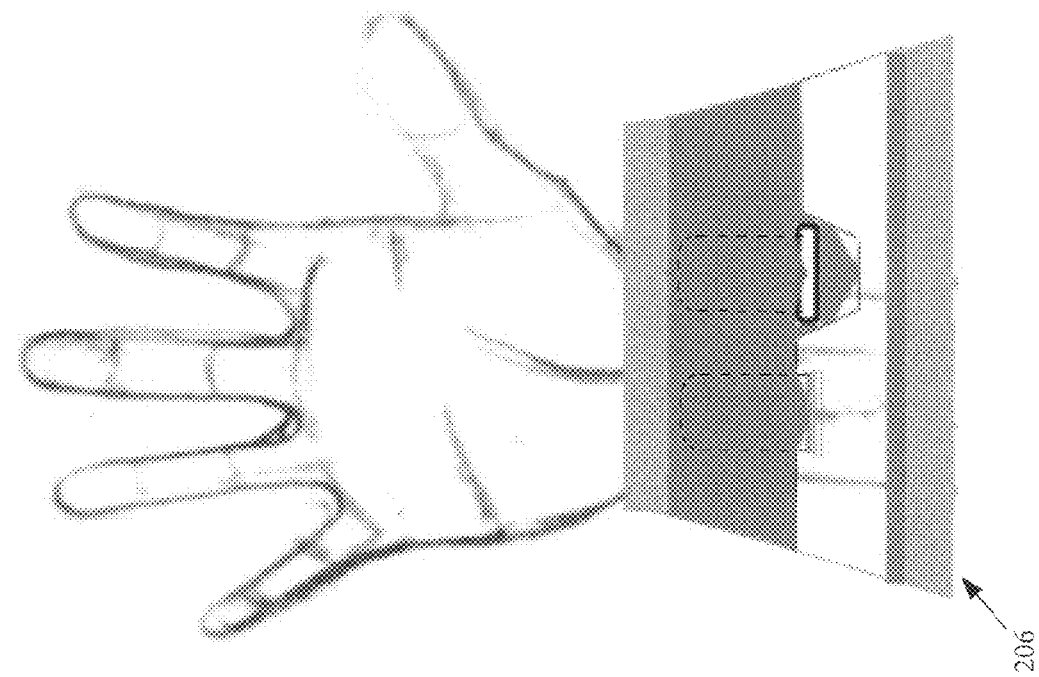
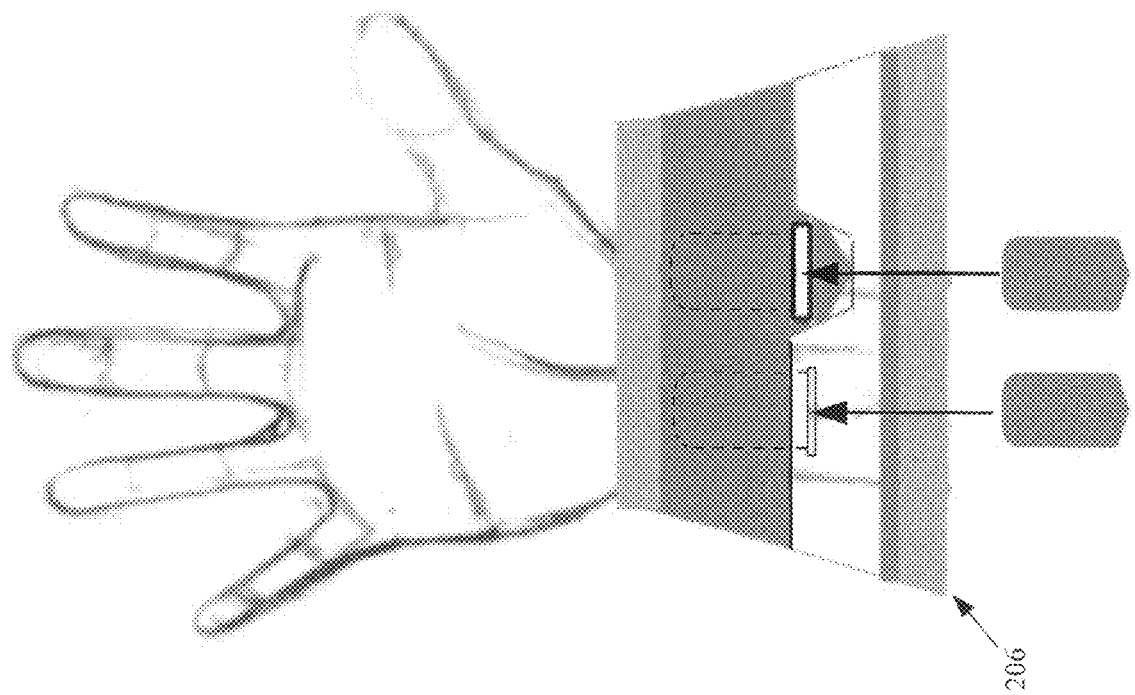

Treatment:
-Use compression to reduce pressure on medial nerve.
-Use ice packs (2) only Carpal Tunnel Syndrome Treatment:
-Use high compression to reduce rubbing of tendons in first dorsal compartment;
-Use ice packs (2) only De Quervains Tenosynovitis (DQT)

(Knee Brace-Older Person)

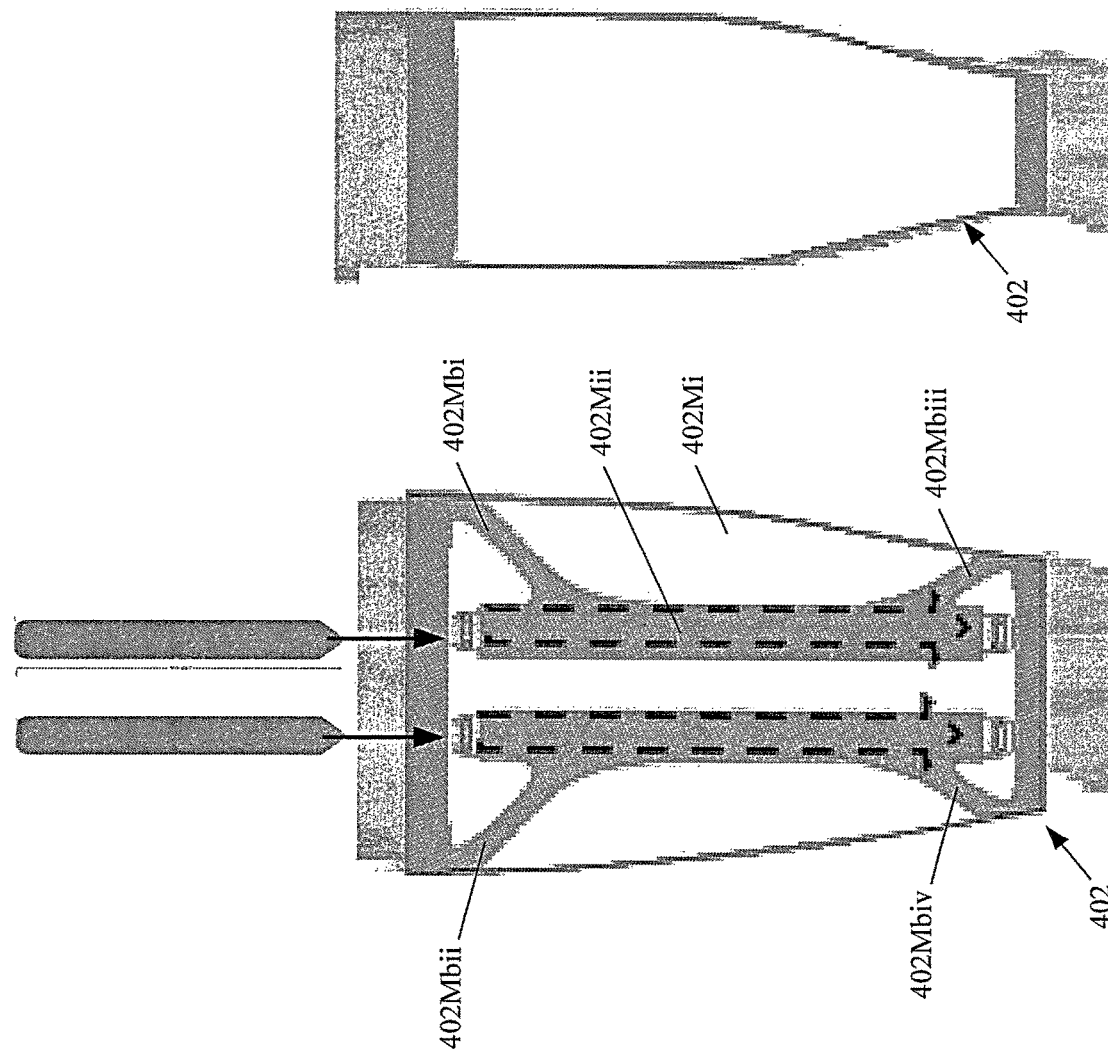

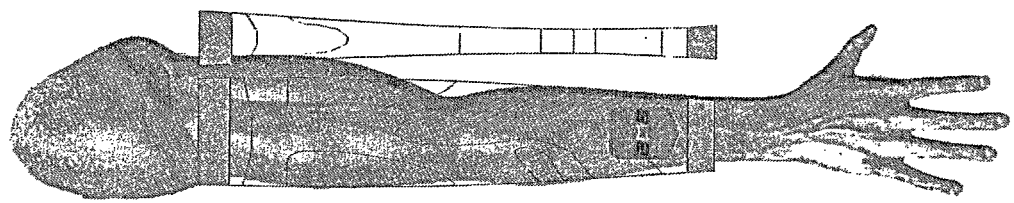
FIG. 34ZZZ
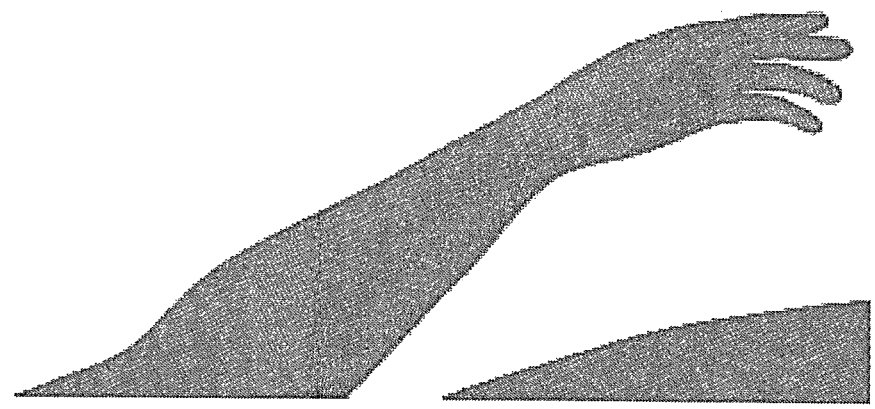
FIG. 34ZZ

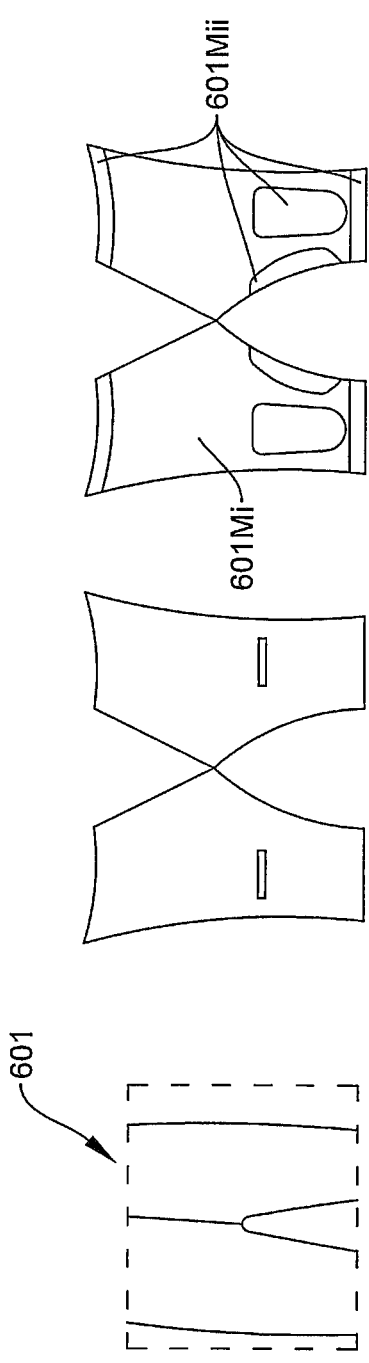
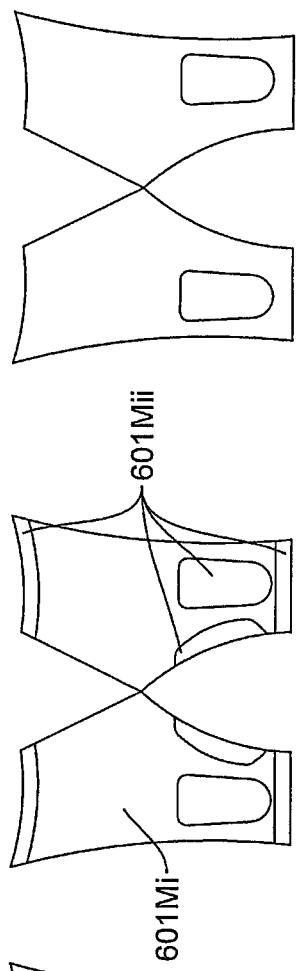
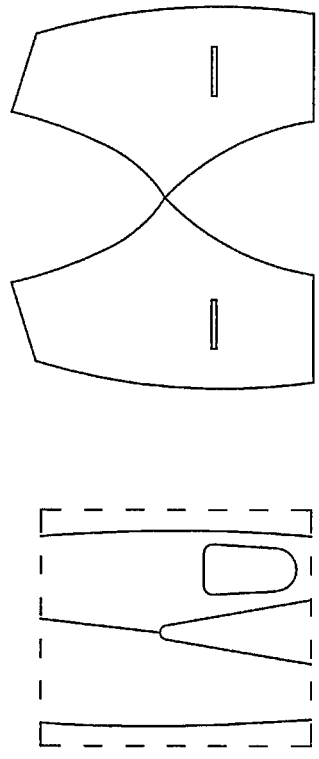
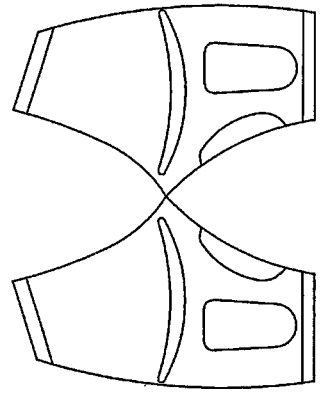
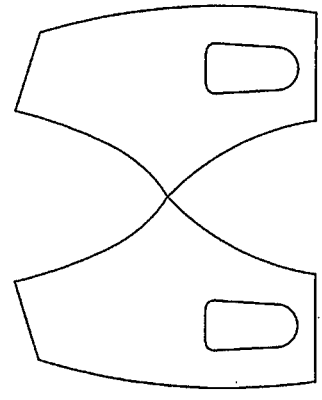
FIG. 35
FIG. 36
FIG. 37
FIG. 38
FIG. 39
FIG. 40
FIG. 41
FIG. 42

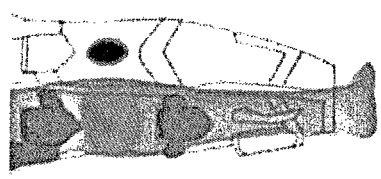
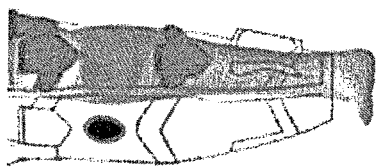
FIG. 55D
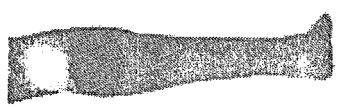
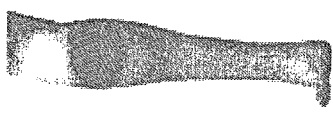
FIG. 55C
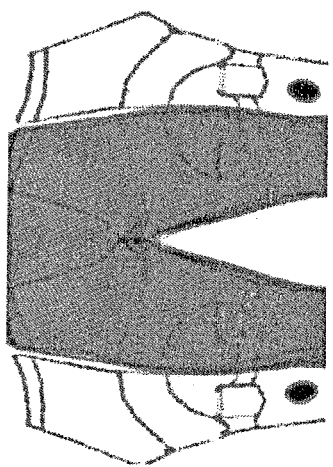
FIG. 55B
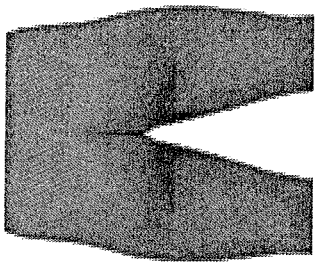
FIG. 55A

COMPRESSION GARMENTS

CROSS REFERENCES TO RELATED APPLICATIONS

This application is a continuation in part of U.S. patent application Ser. No. 17/020,072, filed on Sep. 14, 2020, which claims priority on: U.S. Provisional Application Ser. No. 63/076,501, filed on Sep. 10, 2020; U.S. Provisional Application Ser. No. 62/911,495, filed on Oct. 7, 2019; and U.S. Provisional Application Ser. No. 62/934,587, filed on Nov. 13, 2019; and U.S. patent application Ser. No. 17/020,072 also claims priority on: U.S. Provisional Application Ser. No. 62/634,591, filed on Sep. 12, 2018, having the title "Therapeutic Shirt with High Compression Material Positioned over Externally Accessed Pockets Housing Custom Heat/Cold Packs"; and U.S. patent application Ser. No. 17/020,072 is also a continuation in part of U.S. patent application Ser. No. 17/008,734, having the title "Therapeutic Shirt with High Compression Support for Improved Posture for Pregnant Women and Overweight Wearers," which claims priority on U.S. Provisional Application Ser. No. 62/899,277, filed on Sep. 12, 2019; all disclosures of which are incorporated herein by reference.

FIELD OF THE INVENTION

The subject technology relates generally to compression garments and thermal therapy garments, and more particularly to leg, arm, and pants garments configured with specially located high compression materials to provide targeted compression areas with pockets underneath those compression areas, which pockets receive heat and/or cold packs that are inserted externally, to effectively treat and/or prevent injuries.

BACKGROUND OF THE INVENTION

Compression garments are clothing items that may be worn to provide support in the form of compressive pressure applied to a particular region or regions of the wearer's body. Compression garments may be used by the wearer for therapeutic reasons and also for enhancing athletic performance during sporting events. In general, the use of various different pressures that may be achieved by compression fabrics with different engineered compression gradients for medical and athletic purposes has been studied. See e.g., "Study of Properties of Medical Compression Fabrics," Lijing Wang, Martin Felder, and Jackie Y. Cai, Journal of Fiber Bioengineering & Informatics, Global Science Press, p. 15-22 (2011); "Compression Garments for Medical Therapy and Sports," Ying Xiong and Xiaoming Tao, Polymers, Vol. 10, No. 663, 3-19, Jun. 14, 2018; "From 3d Scan To Body Pressure Of Compression Garments," Li Z, Malengier B, Vasile S, Cools J, Van Langenhove L, AUTEX2019—19th World Textile Conference on Textiles at the Crossroads, 11-15 Jun. 2019, Ghent, Belgium; "Physics of Compression," Hugo Partsch, Published by Guset User, 2015 Nov. 24; and "Bringing Light Into the Dark: Effects of Compression Clothing on Performance and Recovery," Dennis-Peter Born, Billy Sperlich, and Hans-Christer Holmberg, International Journal of Sports Physiology and Performance, 2013, 8:4-18 (2013).

Examples of the use of compression garments for medical reasons include compression stockings for improving blood circulation, and treating varicose veins, edema, lymphedema, and deep vein thrombosis. Compression socks may be worn on a plane where a person is inactive and confined in a small space to reduce the risk of blood clots. Compression stockings and socks may also be worn by a person who must stand for long periods of time. Compression sleeves may also be worn on a person's legs to treat shin splints, muscle cramps, and tendonitis.

With respect to the compression garments being used to enhance athletic performance, such use helps the muscles to more quickly recover from previous strenuous activity. Scientific studies have shown that the wearing of a compression sleeve causes the walls of the wearer's arteries to dilate, thereby increasing the flow of blood to those muscles, providing more oxygen and nutrients that are needed, which also tends to reduce the build-up of lactic acid. The wearing of a compression sleeve may also serve to support the muscles and reduce muscular vibrations, reducing the fatigue that results from those vibrations, thereby improving athletic endurance.

Some compression garments for enhancing various aspects of the wearer may include, for example, the following U.S. Pat. No. 5,937,442 to Yamaguchi; U.S. Pat. No. 6,440,094 to Maas; U.S. Pat. No. 7,871,388 to Brown; U.S. Pat. No. 8,172,782 to Rock, U.S. Pat. No. 8,827,767 to Samoodi; U.S. Pat. No. 9,167,854 to Levian; 2009/0062704 (Brown); and 2012/0078147 (Ogulnick).

In addition, some garments have been adapted to apply thermal treatment (applications of heat/cold) to portions of the person's body, as shown for example by the following U.S. Pat. No. 5,826,273 to Eckes; U.S. Pat. No. 8,220,074 to Sutker; U.S. Pat. No. 8,256,034 to Berner; U.S. Pat. No. 8,876,875 to Nilforushan; U.S. Pat. No. 9,339,065 to Willis; 2006/0218692 (Lamarque); 2007/0299489 (Francis); and 2008/0125842 (Petit).

One problem with many prior art devices is that they fail to target very specific areas of the person's body with compression, and also do not supply thermal treatments (heating/cooling) beneath the particularly located high compression areas, which compression improves the application of heat or cold from the thermal pack, to effectively treat certain ailments of the joints and muscles. The compression garments disclosed herein address those and other shortcomings of the prior art.

It is noted that citing herein of any patents, published patent applications, and non-patent literature is not an admission as to any of those references constituting prior art with respect to the herein disclosed and/or claimed apparatus.

OBJECTS OF THE INVENTION

It is an object of the invention to provide a compression garment in the form of a sleeve for an arm that may be worn to treat young people with golf/tennis elbow issues, and to prevent injury to a person's arm that is currently healthy.

It is another object of the invention to provide a compression garment in the form of a sleeve for an arm that may be worn to treat older people with golf/tennis elbow issues, and to prevent injury to a person's arm that is currently healthy.

It is a further object of the invention to provide a compression garment in the form of a sleeve for a leg that may be worn to treat young and older people with knee joint issues.

It is another object of the invention to provide a compression garment in the form of a sleeve for a leg that may be worn to treat young and older people with knee-related muscle issues.

It is also an object of the invention to provide a compression garment in the form of a sleeve for a leg that may be worn to treat people with shin-related issues such as shin splints.

It is another object of the invention to provide a compression garment in the form of a sleeve for a leg that may be worn to treat people with calf muscle issues.

It is also an object of the invention to provide a compression garment in the form of a sleeve for an arm that may be worn to treat young or older people with wrist-related issues such as carpal tunnel syndrome.

It is another object of the invention to provide a compression garment in the form of a sleeve for an ankle that may be worn to treat young or older people with ankle-related issues such as sprains, torn ligaments, etc.

It is a further object of the invention to provide a compression garment in the form of pants that may be worn to treat young and older people with hip-related and leg-related muscle, joint, or connective issues.

It is another object of the invention to provide a compression garment in the form of a sleeve for a leg that may be worn to treat people with thigh muscle issues.

It is another object of the invention to provide a compression garment in the form of a sleeve for a full arm that may be worn to treat young people with arm muscle tissue issues that extend from the upper arm to the wrist.

It is another object of the invention to provide a compression garment in the form of a sleeve for a full arm that may be worn to treat older people with arm joint or connective tissue issues that extend from the upper arm to the wrist.

It is another object of the invention to provide a compression garment in the form of a sleeve for the full leg that may be worn to treat young people with full leg compression to support muscle tissue issues that extend from the thigh to the ankle.

It is another object of the invention to provide a compression garment in the form of a sleeve for the full leg that may be worn to treat older people with full leg compression to support joint and connective tissue issues that extend from the thigh to the ankle.

It is another object of the invention to provide a compression garment for a particular region of the body that acts to help repair, support, protect the body region, and provide for pain relief and recovery of specific conditions affecting the body region, whether acute of chronic.

It is a further object of the invention to provide a body-part specific compression brace with physician endorsed areas of high and low compression targeted at supporting specific areas of the underlying muscle, tendons, and connective tissue, where the high compression areas are designed to offer optimum healing benefits and comfort for chronic or acute pain sites.

It is another object of the invention to provide a body-part specific compression brace that includes pockets that may receive heat and/or cold packs therein, which pockets are strategically placed to offer the highest benefit to the affected tissue or injury, where the injury type and desired results dictate whether to apply heat or cold treatments.

It is a further object of the invention to provide custom heat packs configured to be chilled, frozen, or heated for use in treating an injury using a compression brace disclosed herein.

It is another object of the invention to provide a compression sleeve with a stay-in-place material at each end to ensure the compression stays in the proper position while being worn, which ends may be rolled up to position the stay-in-place material away from the body for ease in putting the compression on the affected body region and for preventing overstretching of the circumference of the brace during application/removal, and which ends may thereafter be rolled down to position the stay-in-place material against the wearer's skin.

Further objectives and advantages of the various garments disclosed herein will become apparent from the following description and claims, and from the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description of the various example embodiments is explained in conjunction with appended drawings, in which:

FIG. 13 is a flat pattern for yet another embodiment of an ankle compression;

FIG. 13A is a cross-sectional view through one end of the flat pattern of FIG. 13;

FIG. 15A is a flat pattern for a therapeutic compression garment for a wrist injury, configured to extend from the palm of the hand to the forearm, and having openings formed to receive heat/cold packs into pockets therein to apply heat and/or cold therapy under compression to regions of an arm;

FIG. 15B is a flat pattern for yet a further embodiment of a therapeutic compression garment for a wrist, configured to extend from the palm of the hand to the forearm, and having openings formed to receive heat/cold packs into pockets therein to apply heat and/or cold therapy under compression to regions of an arm;

FIG. 15C is a therapeutic compression garment for treating carpal tunnel syndrome, configured to extend from the wrist to the forearm, and having openings formed to receive heat/cold packs into pockets therein to apply heat and/or cold therapy under compression to regions of an arm;

FIG. 15Ci is a cross-sectional view of the human wrist, showing the tendons of the first compartment, the second compartment, the third compartment, the fourth compartment, and the fifth compartment;

FIG. 16C is a flat pattern for yet a further embodiment of a therapeutic compression garment for treating carpal tunnel syndrome at a wrist of the wearer, shown prior to inserting of the cold packs into the pockets formed therein;

FIG. 16D is the flat pattern of FIG. 16C, shown after inserting of the cold packs into the pockets formed therein;

FIG. 27 is a front view of another embodiment of a therapeutic shin compression;

FIG. 28 is a rear view of the therapeutic shin compression of FIG. 27;

FIG. 34N shows the flat pattern of the therapeutic arm compression of FIG. 34H overlaid on an arm to illustrate treatment provided to an arm that may be affected by ulnar nerve—cubital tunnel syndrome;

FIG. 34O illustrates a flat pattern for a full arm compression configured to generally treat middle age to older individuals whose muscle pain may also involve connective tissue;

Figure 34A:
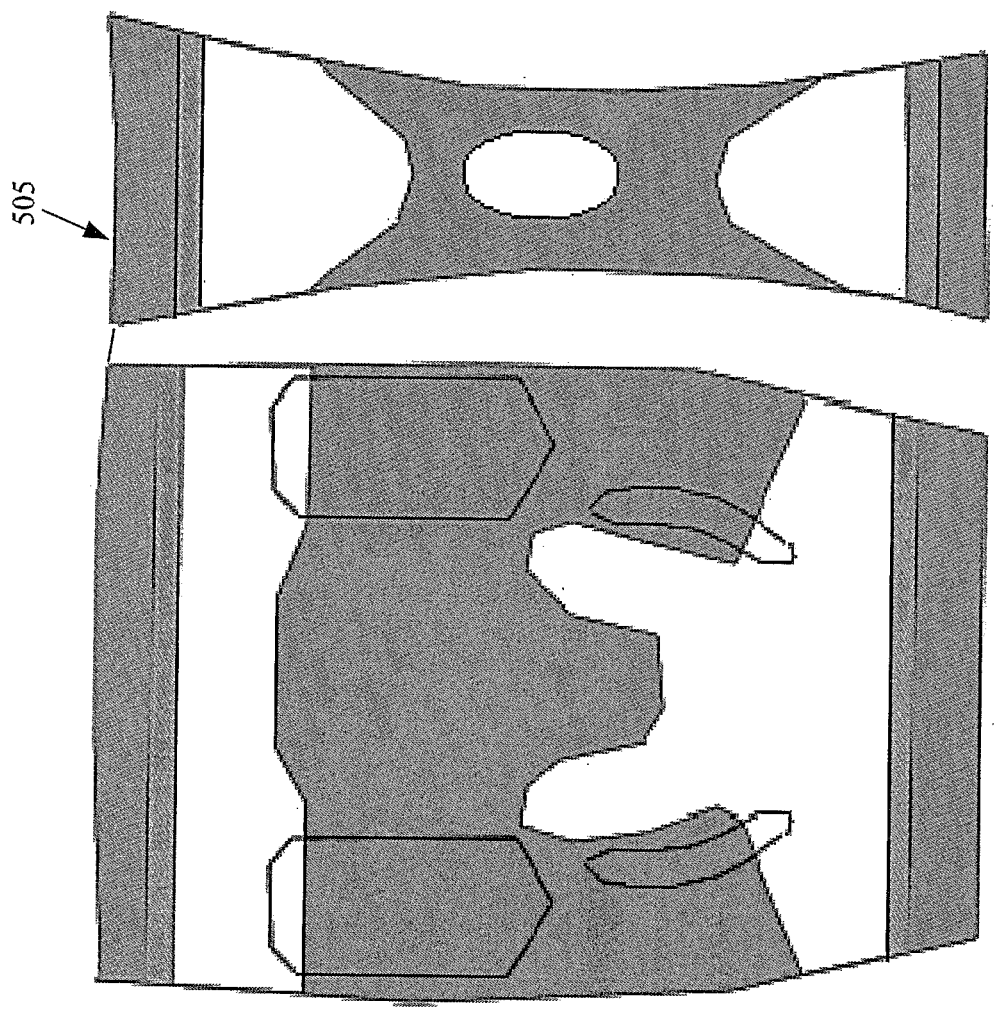
FIG. 34A illustrates a flat pattern for an arm compression configured to treat particular golf or tennis elbow related injuries.
Figure 34D:
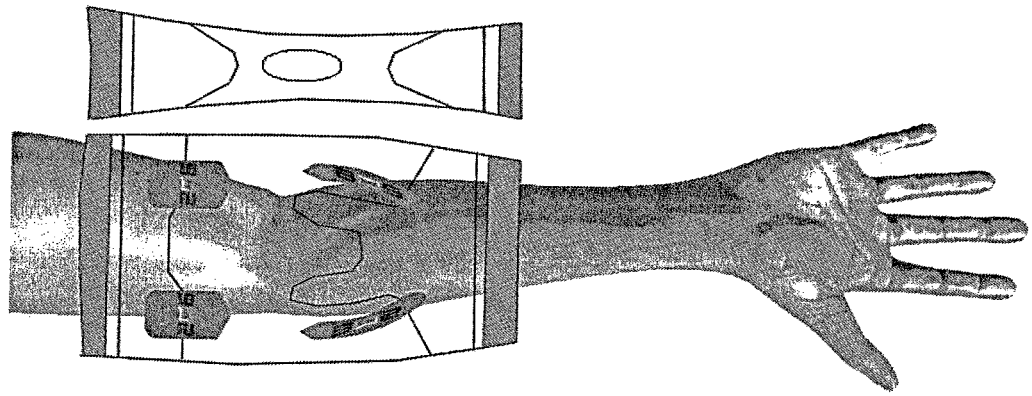
FIG. 34D shows the flat pattern of the therapeutic arm compression of FIG. 34A overlaid on an arm to illustrate treatment provided to an arm that may be affected by lateral epicondylitis and/or medial epicondylitis.
Figure 34C:
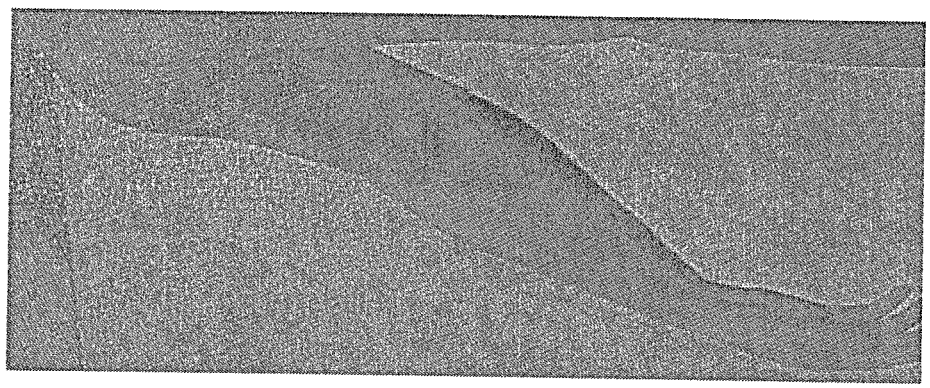
FIG. 34C is an image showing the region of the arm that may be affected by medial epicondylitis.
Figure 34B:
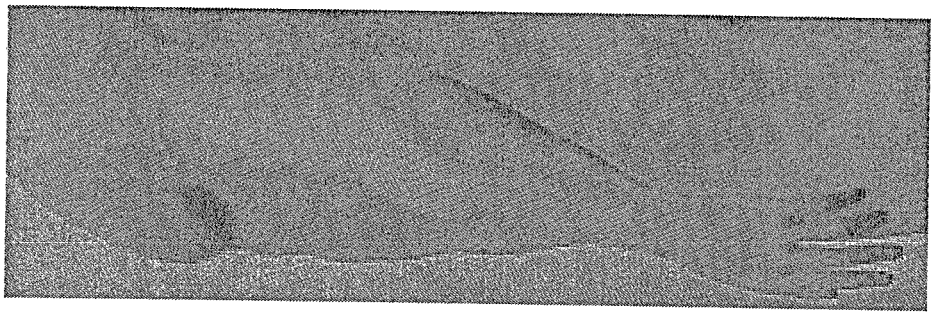
FIG. 34B is an image showing the region of the arm that may be affected by lateral epicondylitis.
Figure 34G:
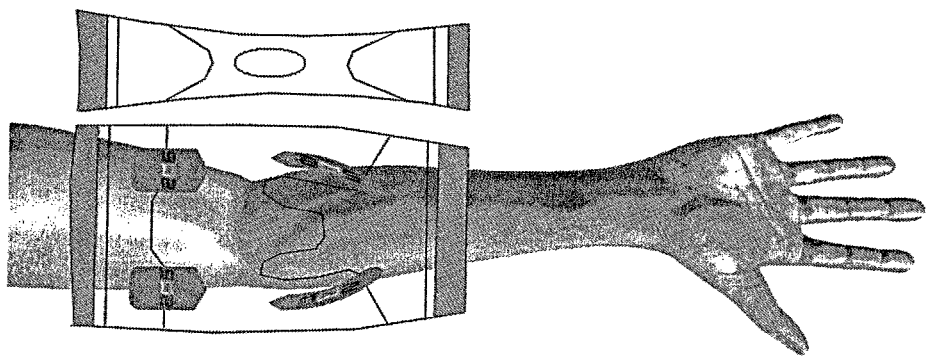
FIG. 34G shows the flat pattern of the therapeutic arm compression of FIG. 34A overlaid on an arm to illustrate treatment provided to an arm that may be affected by biceps strain and/or triceps strain.
Figure 34F:
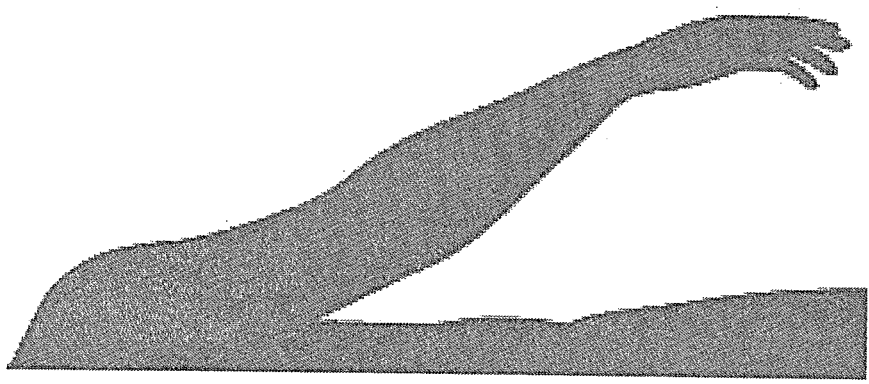
FIG. 34F is an image showing the region of the arm that may be affected by a triceps strain.
Figure 34E:
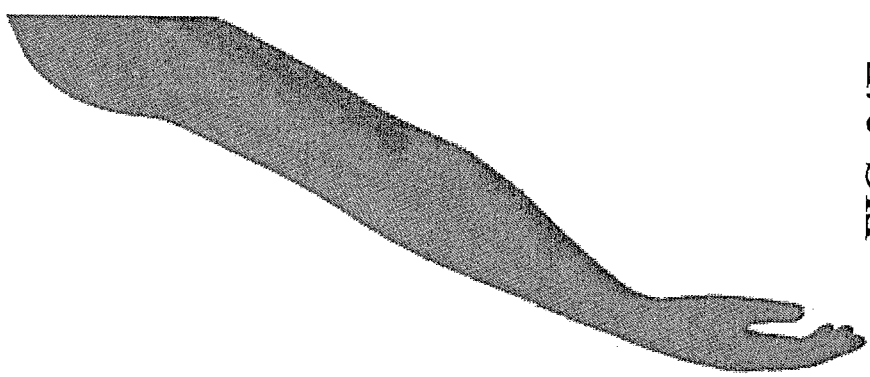
FIG. 34E is an image showing the region of the arm that may be affected by a biceps strain.
Figure 34H:
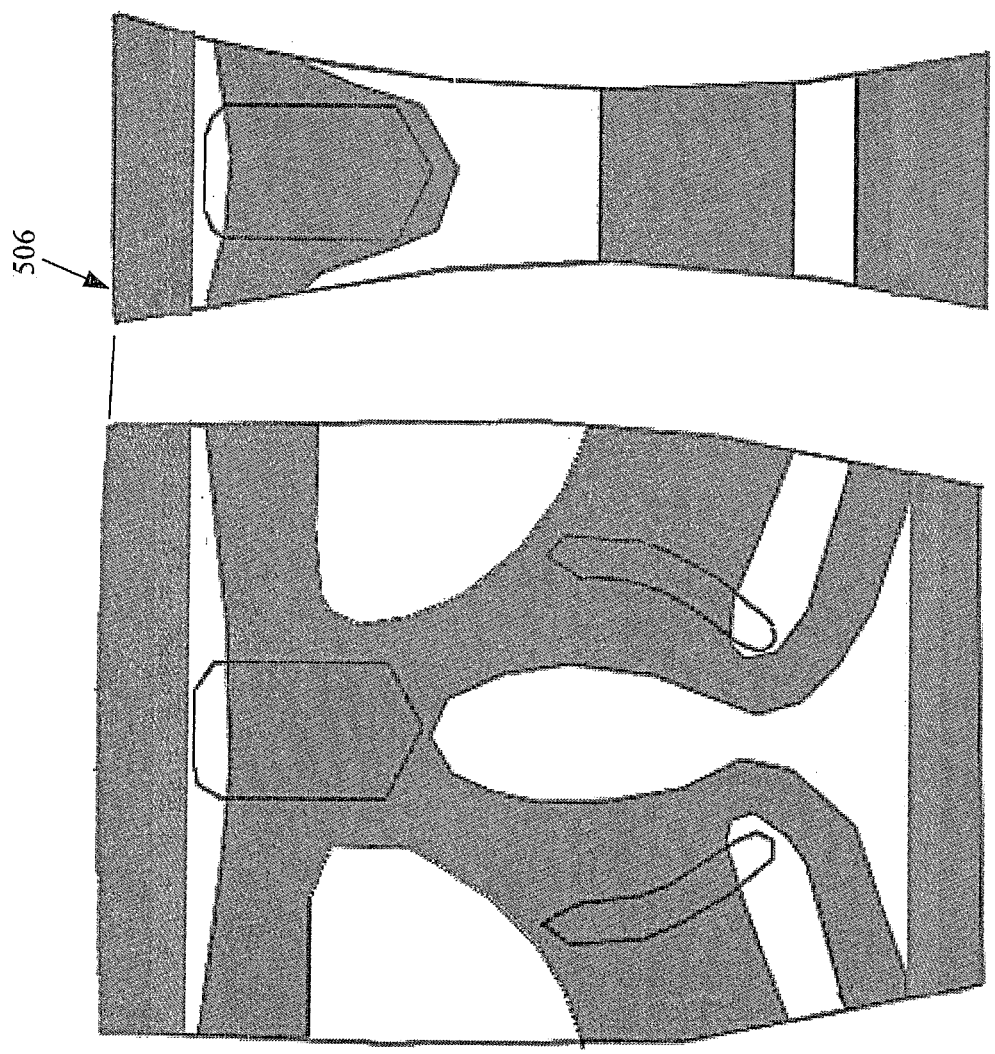
FIG. 34H illustrates a flat pattern for an arm compression configured to treat particular golf or tennis elbow related injuries.
Figure 34J:
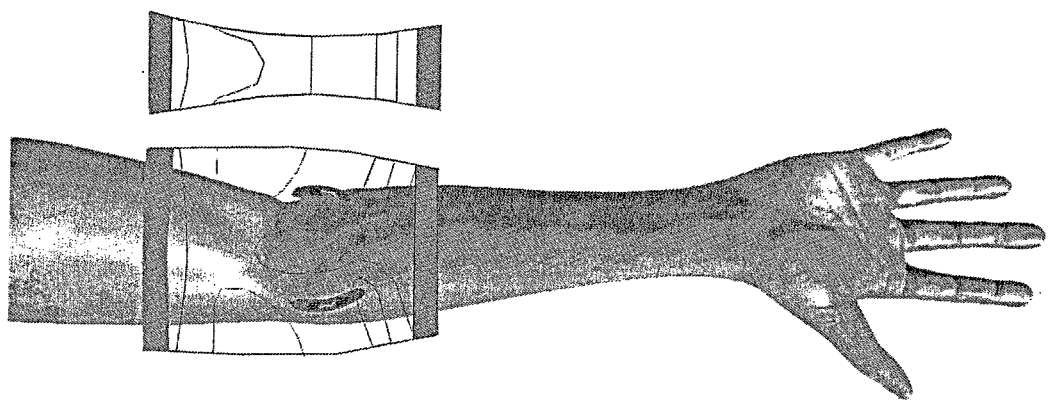
FIG. 34J shows the flat pattern of the therapeutic arm compression of FIG. 34H overlaid on an arm to illustrate treatment provided to an arm that may be affected by ulnar collateral ligament strain.
Figure 34I:
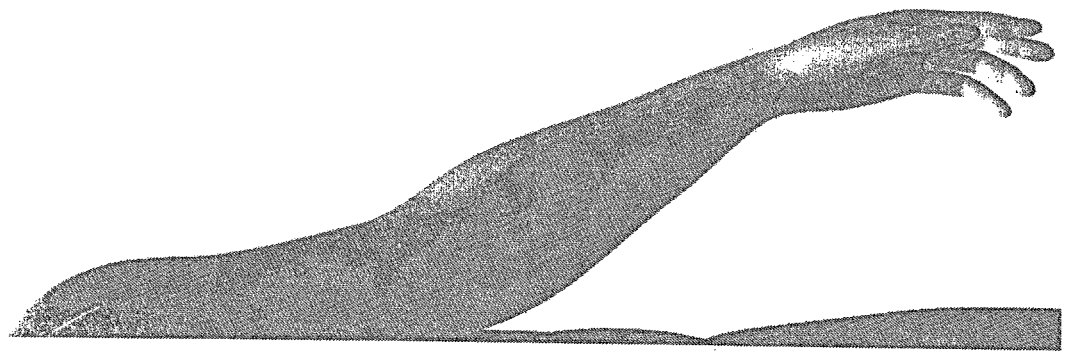
FIG. 34I is an image showing the region of the arm that may be affected by an ulnar collateral ligament strain.
Figure 34L:
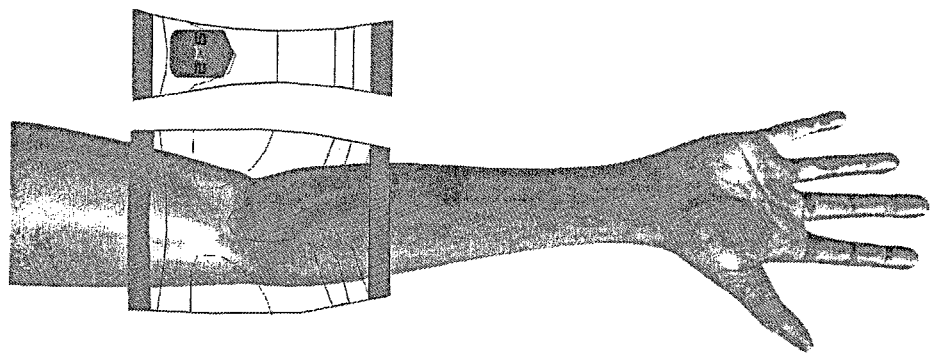
FIG. 34L shows the flat pattern of the therapeutic elbow compression of FIG. 34H overlaid on an arm to illustrate treatment provided to an arm that may be affected by distal biceps strain tendinitis.
Figure 34K:
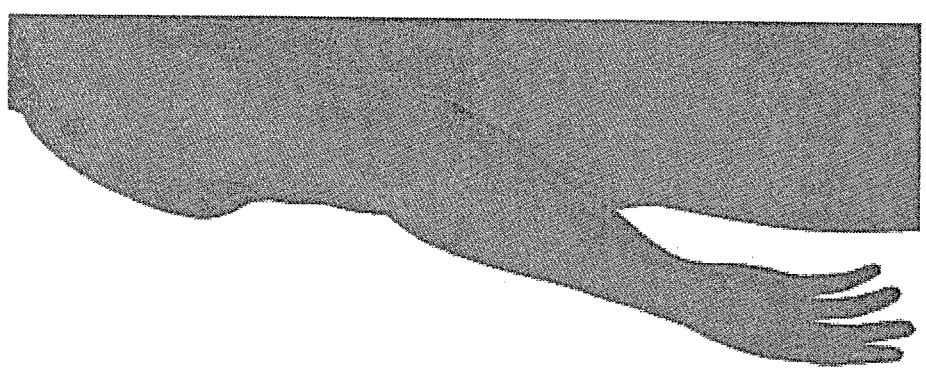
FIG. 34K is an image showing the region of the arm that may be affected by distal biceps strain tendinitis.
Figure 34N:
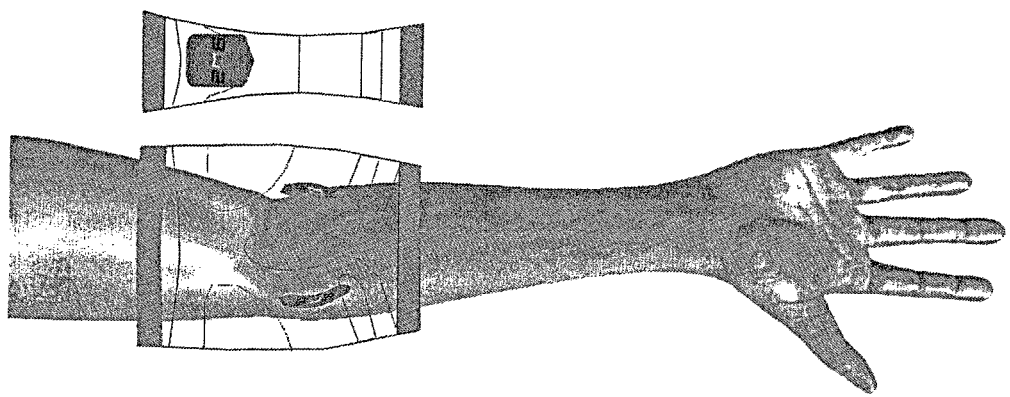
FIG. 34M is an image showing the region of the arm that may be affected by ulnar nerve—cubital tunnel syndrome.
Figure 34M:
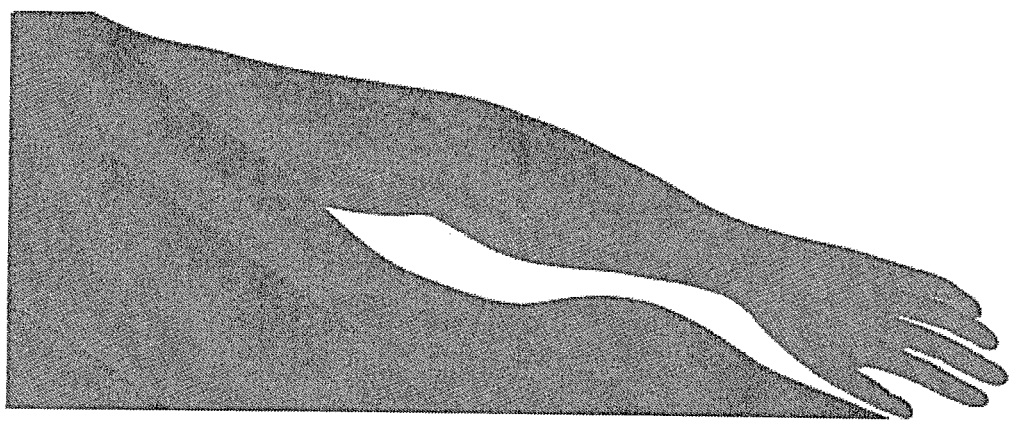
Figure 34O:
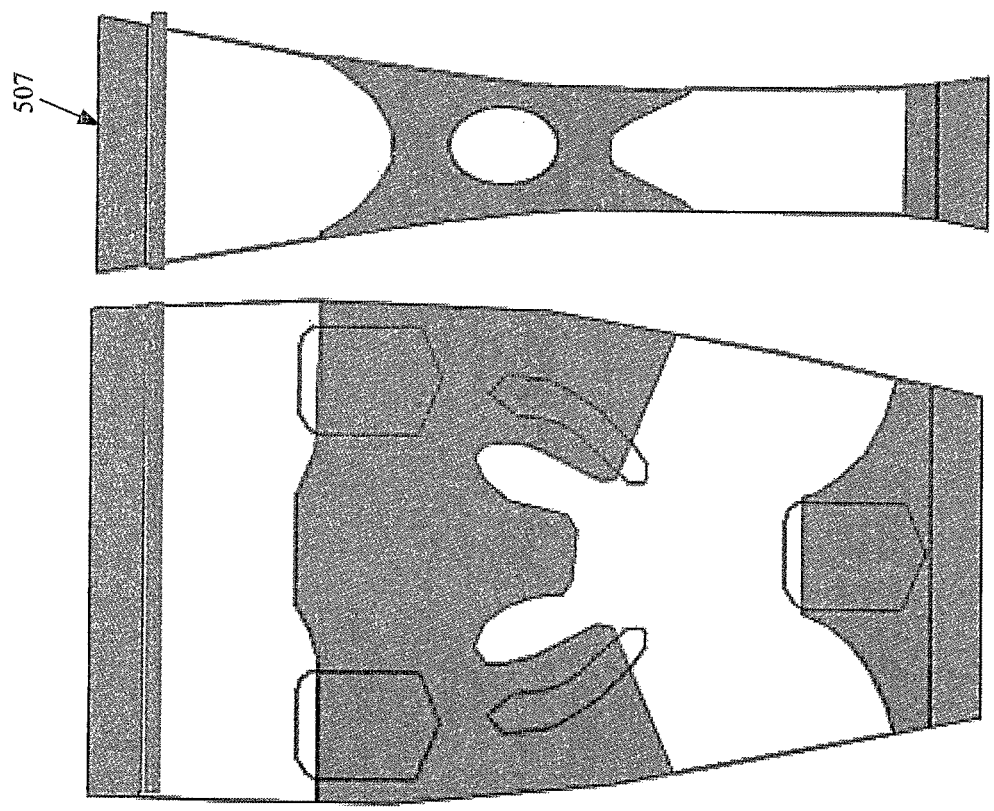
Figure 34O:
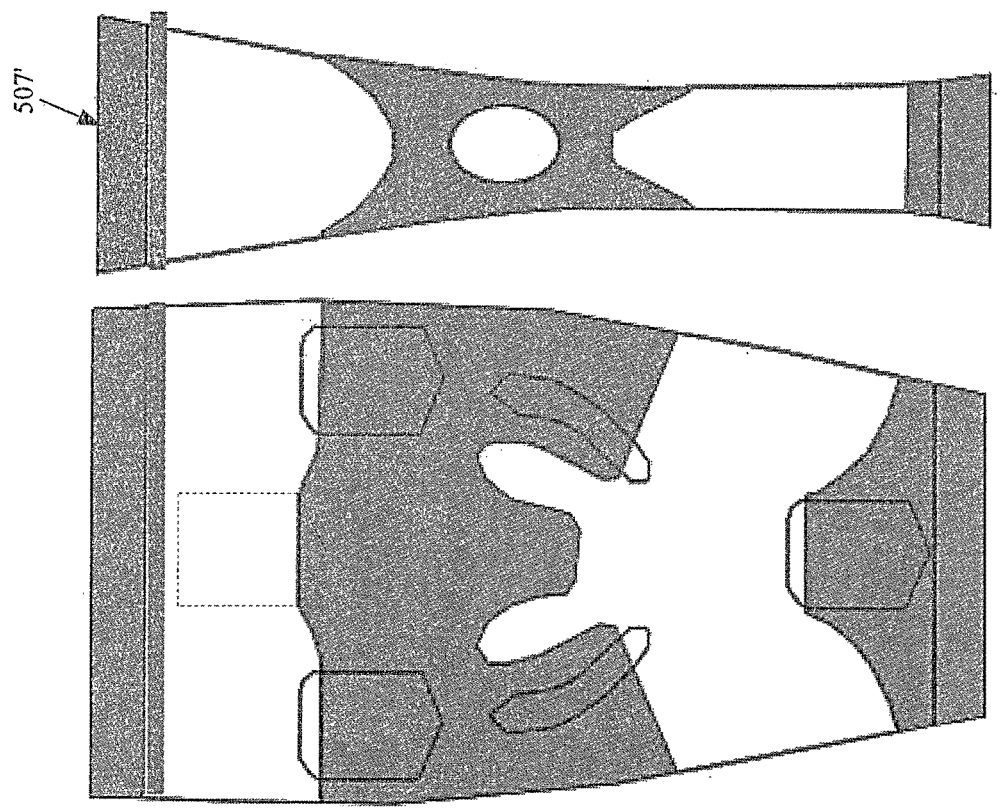
Figure 34Q:
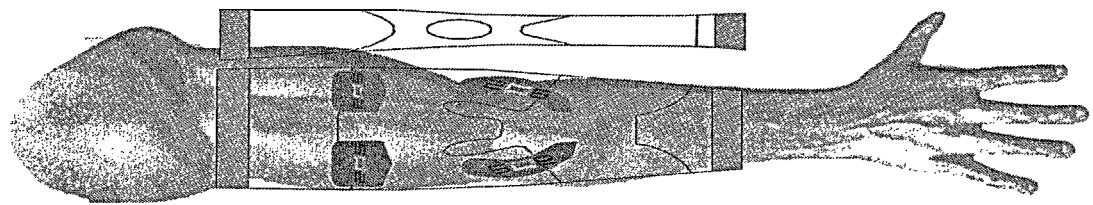
Figure 34P:
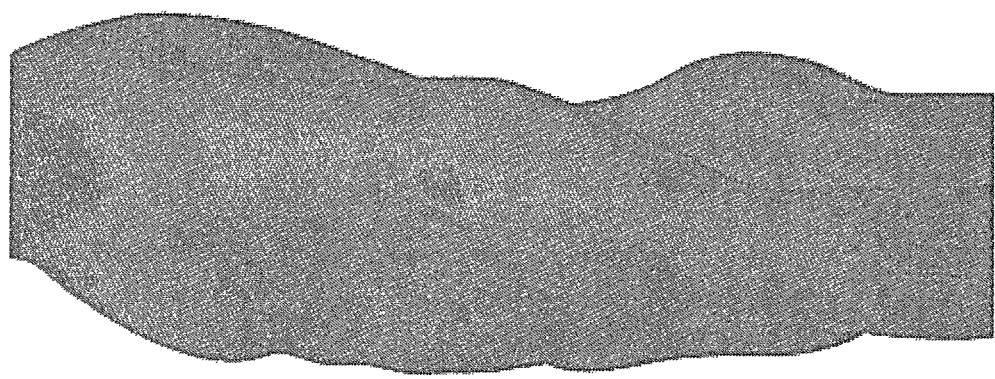
Figure 34S:
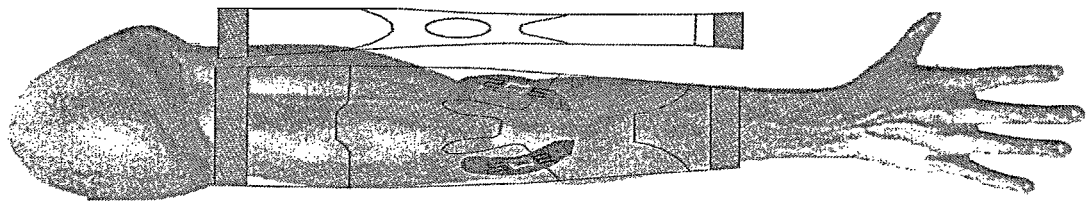
Figure 34R:
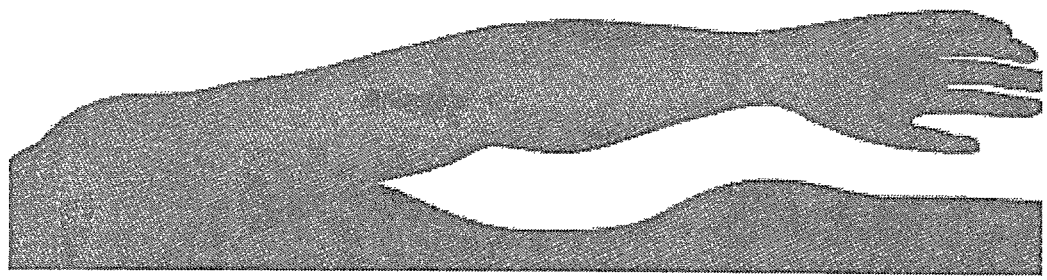
Figure 34U:
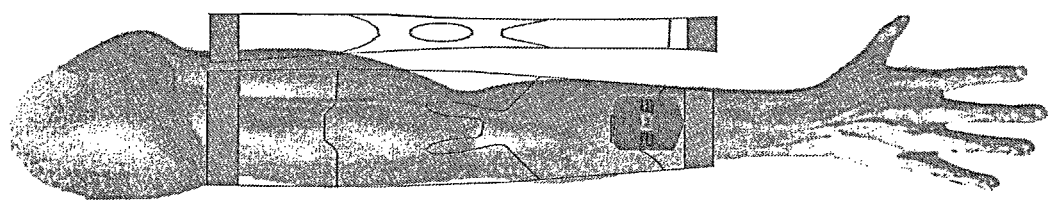
Figure 34T:
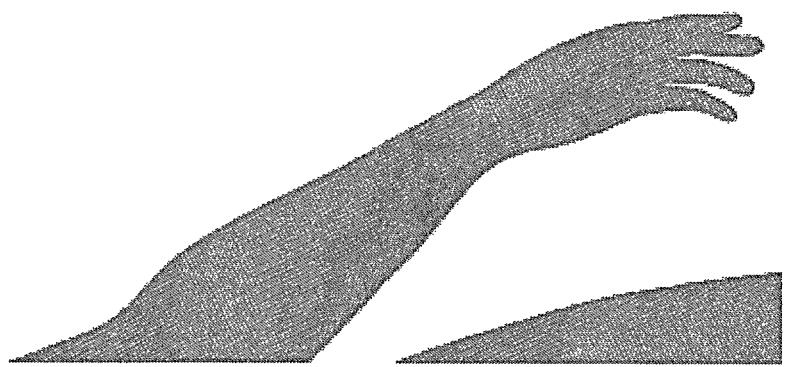
Figure 34V:
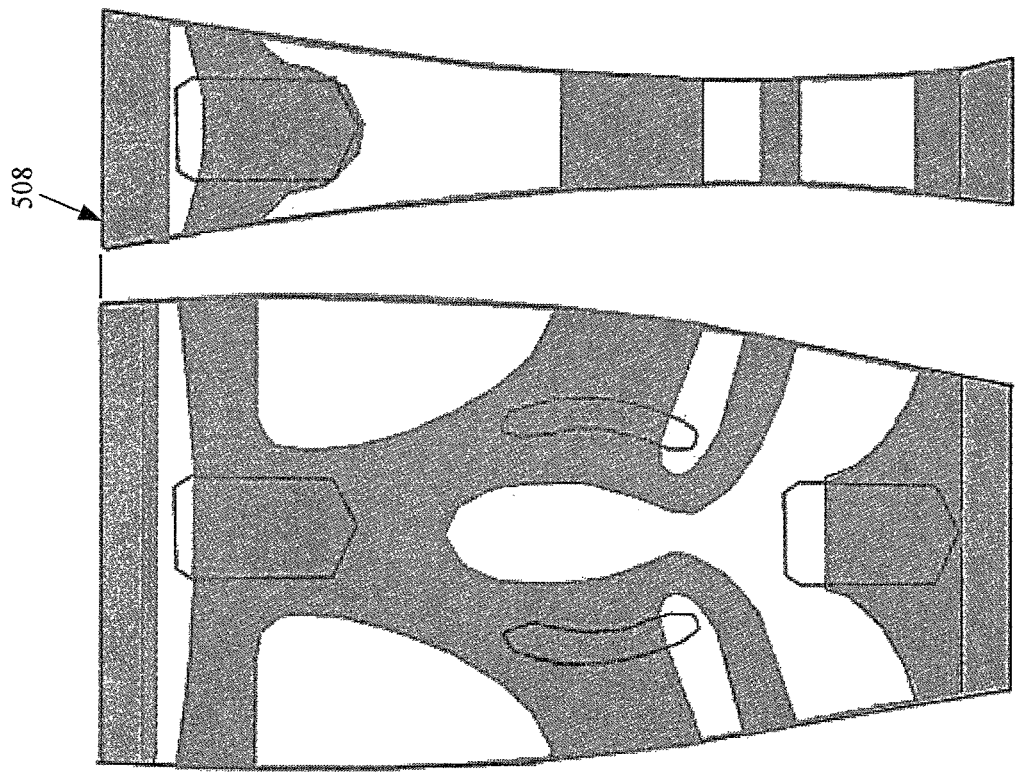
Figure 34X:
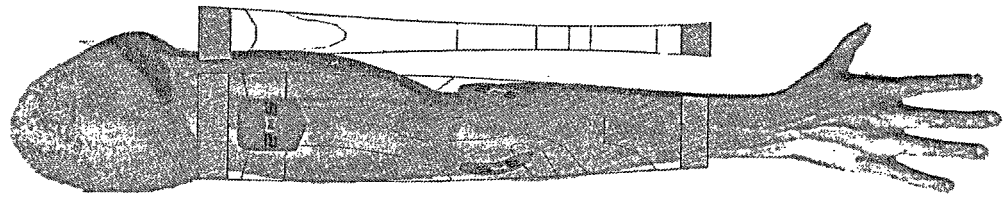
Figure 34W:
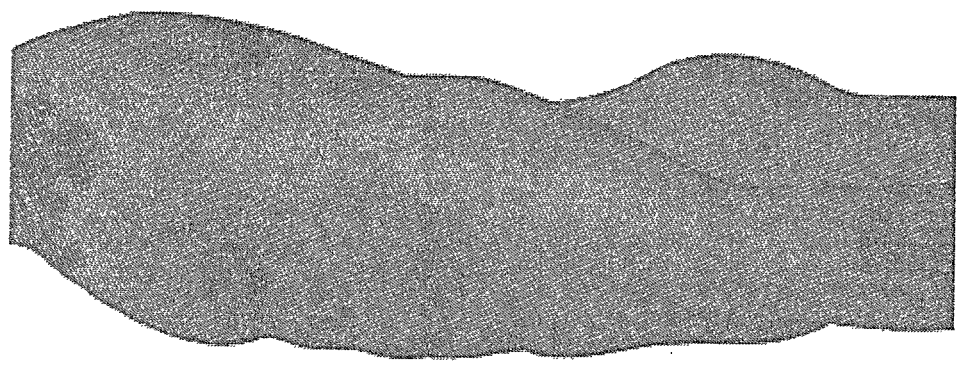
Figure 34Z:
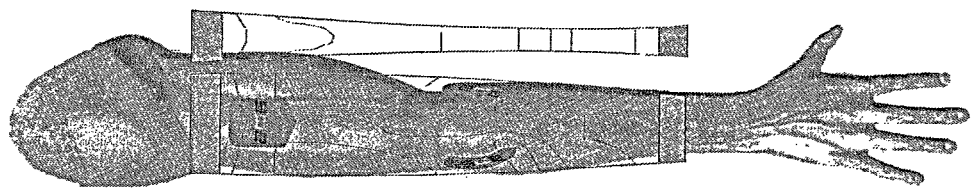
Figure 34Y:
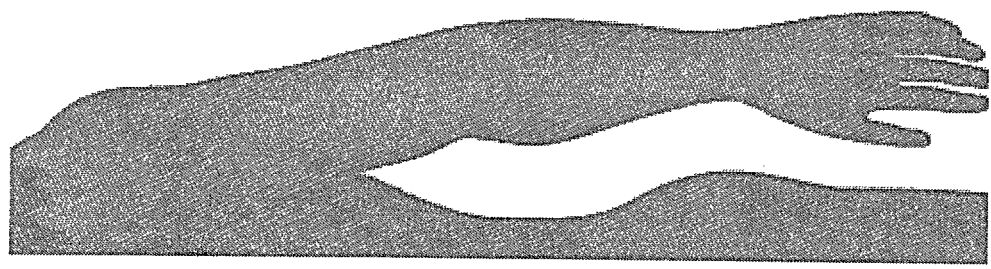

FIG. 34Oi illustrates a flat pattern for a full arm compression configured to generally treat middle age to older individuals whose muscle pain may also involve connective tissue, being formed the same as the compression of FIG. 34O, but which includes one additional pocket to receive an additional heat/cold pack in the sleeve;

FIG. 34P is an image showing the region of the arm (distal biceps and triceps) that may be supported to prevent traction overload injury for a middle age to older person;

FIG. 34Q shows the flat pattern of the therapeutic arm compression of FIG. 34O overlaid on an arm to illustrate support being provided to distal biceps and triceps to prevent traction overload injury for a middle age to older person;

FIG. 34R is an image showing the region of the arm (medial/lateral forearm muscle groups) that may be supported to decrease Varus and Valgus stress for a middle age to older person;

FIG. 34S shows the flat pattern of the therapeutic arm compression of FIG. 34O overlaid on an arm to illustrate support being provided to medial/lateral forearm muscle groups to decrease Varus and Valgus stress for a middle age to older person;

FIG. 34T is an image showing the region of the arm (flexor tendons) that may be supported to prevent bowstringing during sports for a middle age to older person;

FIG. 34U shows the flat pattern of the therapeutic arm compression of FIG. 34O overlaid on an arm to illustrate support being provided to flexor tendons to prevent bowstringing during sports for a middle age to older person;

FIG. 34V illustrates a flat pattern for a full arm compression configured to generally treat younger to middle age individuals with a muscle injury or strain to the upper and lower arm and elbow regions, being focused on the larger tendon and muscle groups of the arm;

FIG. 34W is an image showing the region of the arm (distal biceps and triceps) that may be supported to prevent traction overload injury for a younger to middle aged person;

FIG. 34X shows the flat pattern of the therapeutic arm compression of FIG. 34V overlaid on an arm to illustrate support being provided to distal biceps and triceps to prevent traction overload injury for a younger to middle aged person;

FIG. 34Y is an image showing the region of the arm (medial/lateral forearm muscle groups) that may be supported to decrease Varus and Valgus stress for a younger to middle aged person;

FIG. 34Z shows the flat pattern of the therapeutic arm compression of FIG. 34V overlaid on an arm to illustrate support being provided to medial/lateral forearm muscle groups to decrease Varus and Valgus stress for a younger to middle aged person;

FIG. 34ZZ is an image showing the region of the arm (flexor tendons) that may be supported to prevent bowstringing during sports for a younger to middle aged person;

FIG. 34ZZZ shows the flat pattern of the therapeutic arm compression of FIG. 34V overlaid on an arm to illustrate support being provided to flexor tendons to prevent bowstringing during sports for a younger to middle aged person;

FIG. 35 is a front view of a compression garment configured as short-length pants for a younger wearer, with openings formed to receive heat/cold packs into pockets therein to apply heat and/or cold therapy under compression to treat younger people with hip-related and leg-related muscle issues, shown after being donned by a wearer;

FIG. 36 is a rear view of a compression garment configured as short-length pants shown in FIG. 35;

FIG. 37 is a first view of a flat pattern usable to make the front side of the compression garment as shown in FIG. 35, showing the openings;

FIG. 38 is a first view of a flat pattern usable to make the rear side of the compression garment as shown in FIG. 36, showing the openings;

FIG. 39 is a second view of the flat pattern usable to make the front side of the compression garment as shown in FIG. 35, showing the locations of the high compression material, prior to forming the openings;

FIG. 40 is a second view of the flat pattern usable to make the rear side of the compression garment as shown in FIG.

Figure 43:
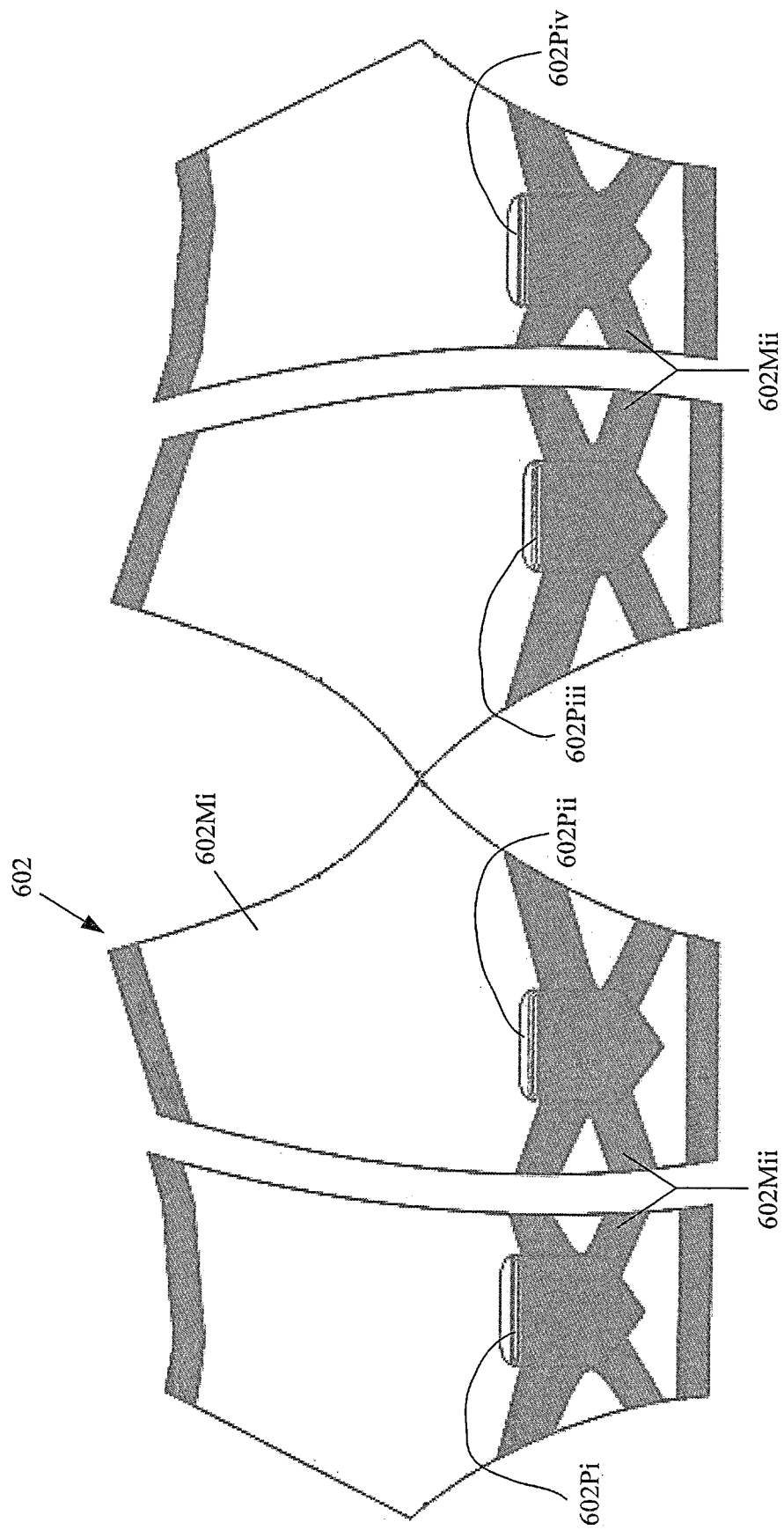
Figure 43A:
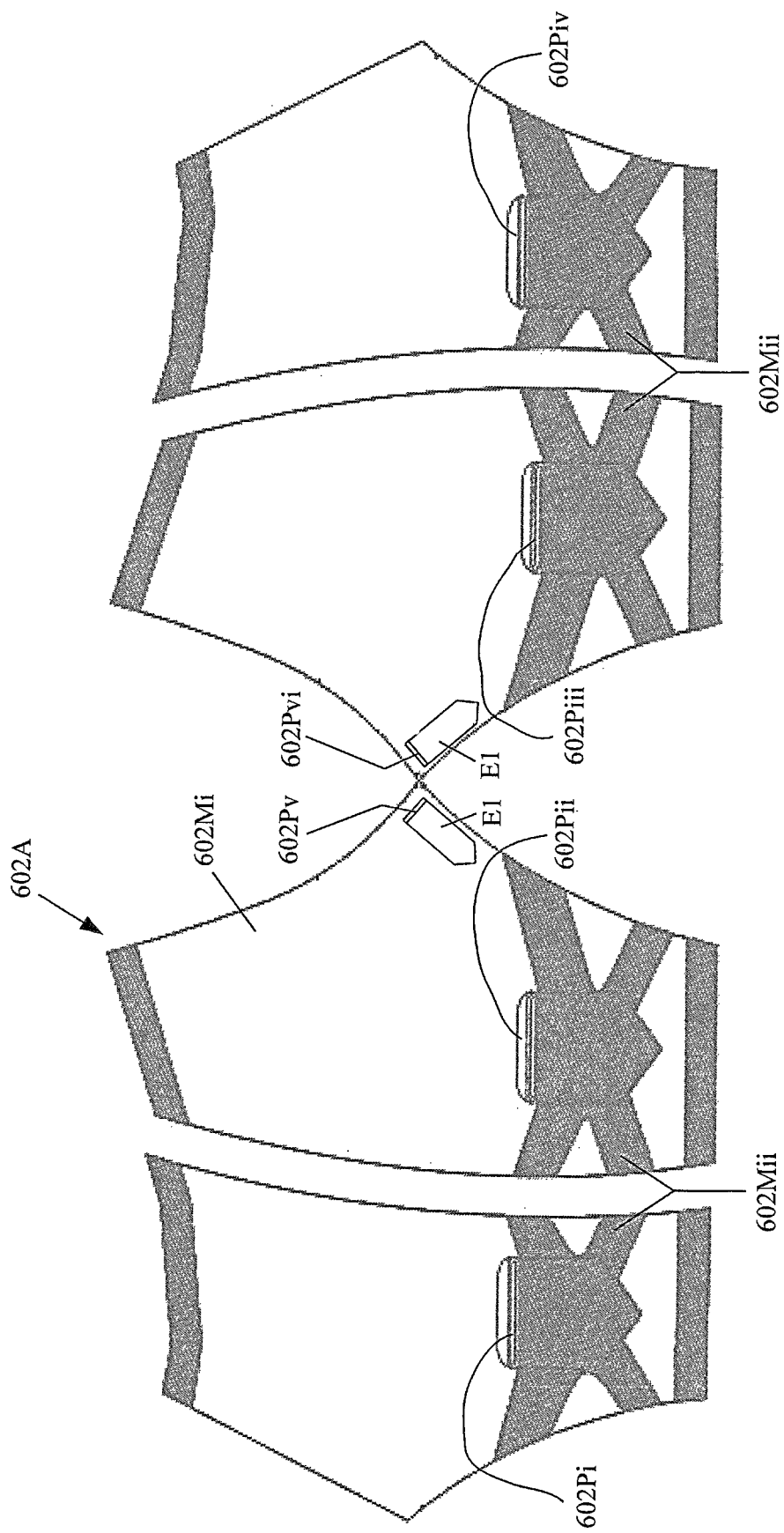
Figure 43E:
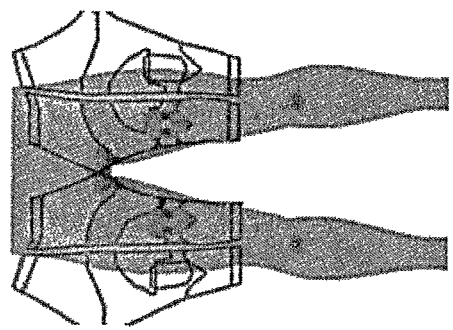
Figure 43D:
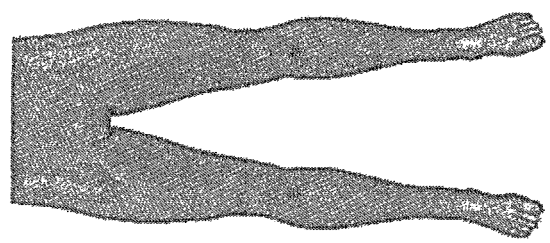
Figure 43C:
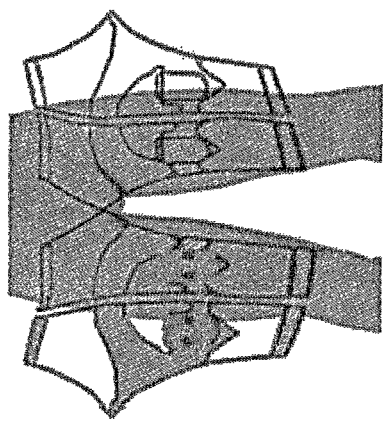
Figure 43B:
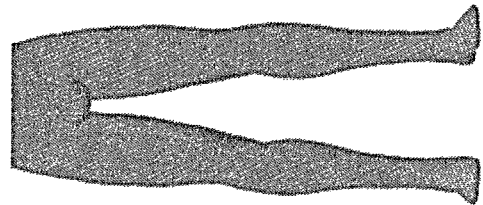
Figure 43G:
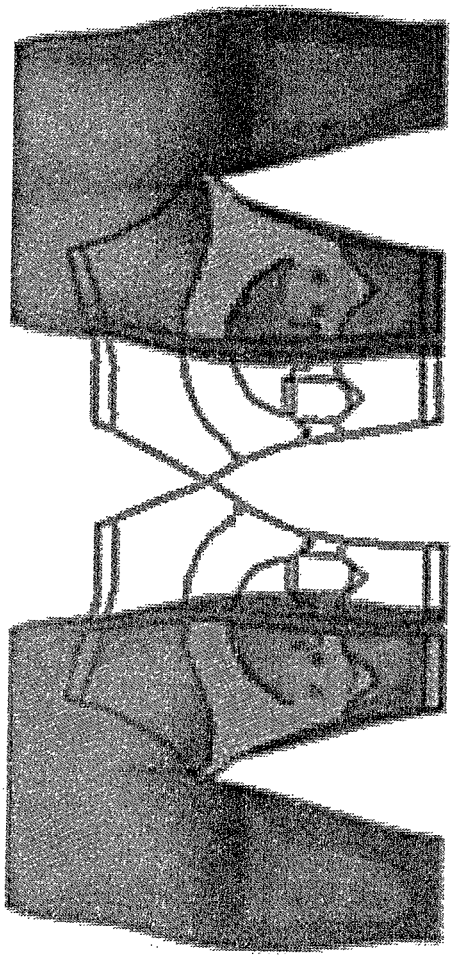
Figure 43F:
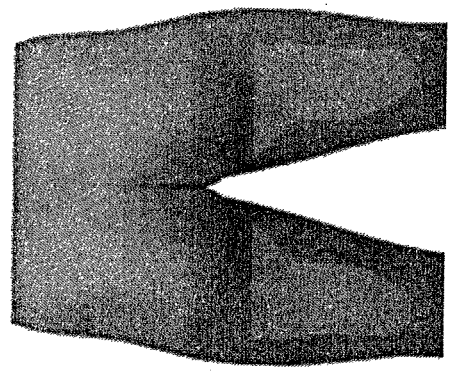
Figure 50:
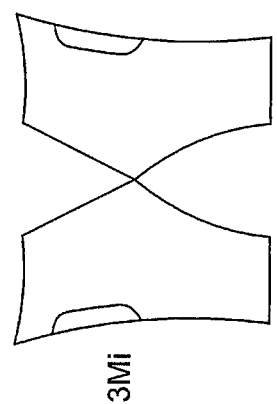
Figure 51:
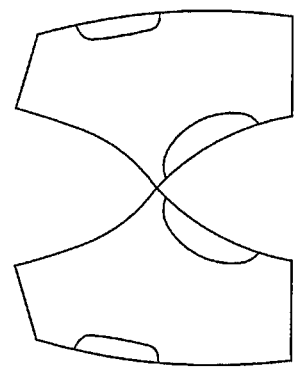
Figure 48:
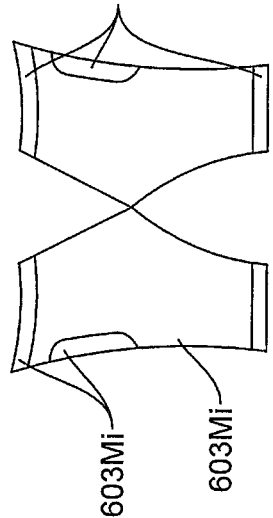
Figure 49:
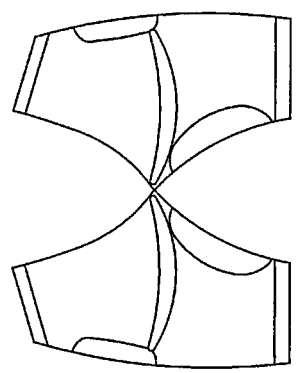
Figure 46:
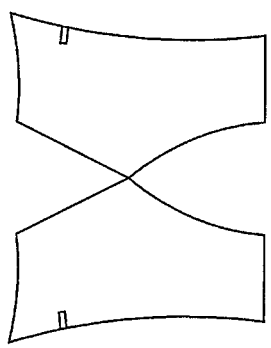
Figure 47:
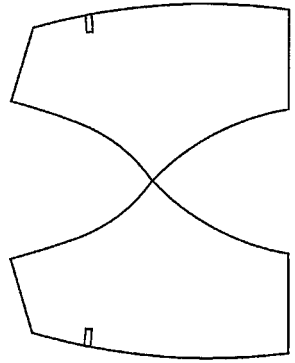
Figure 44:
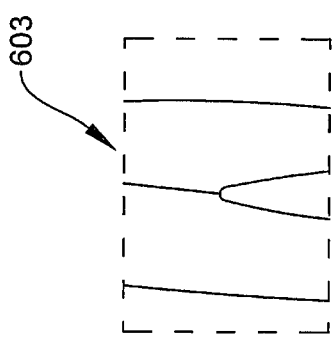
Figure 45:
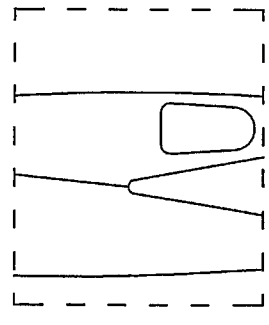
Figure 52:
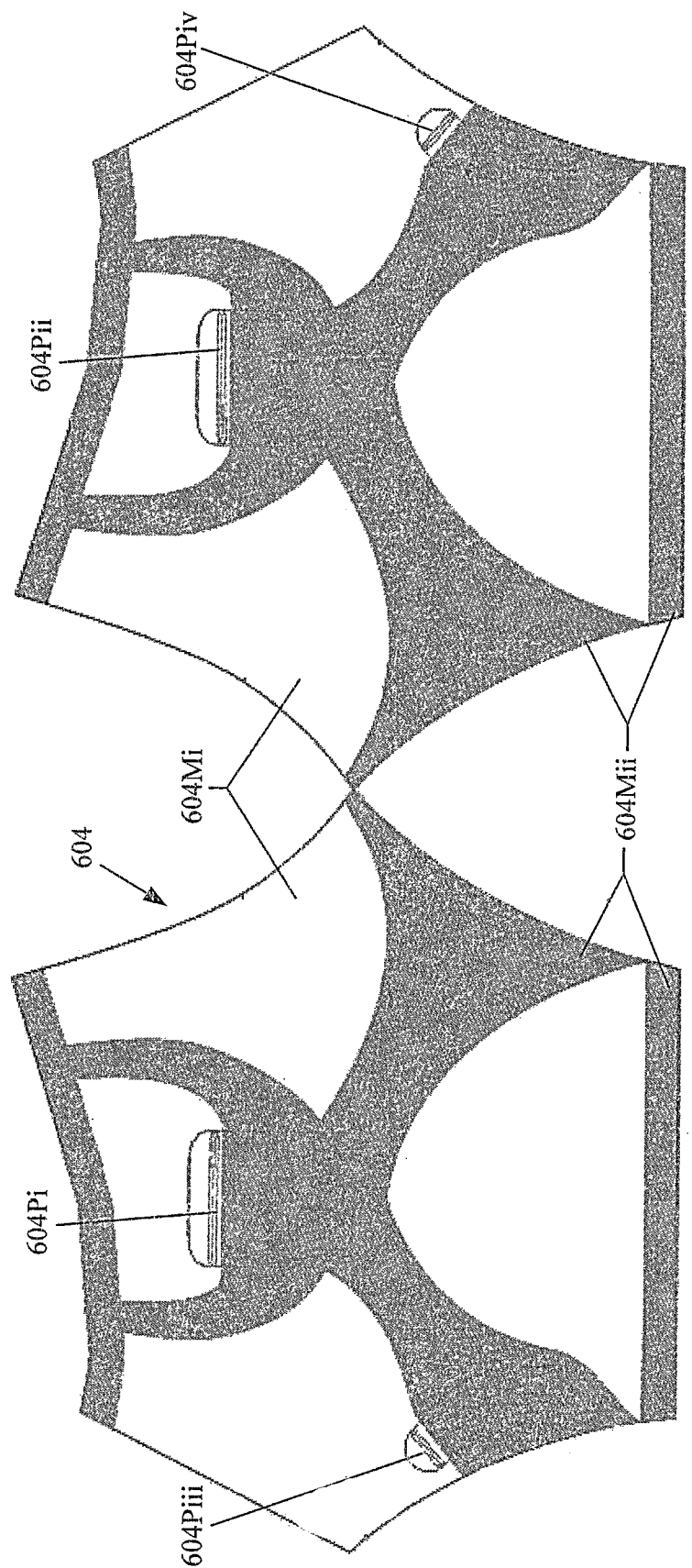
Figure 52A:
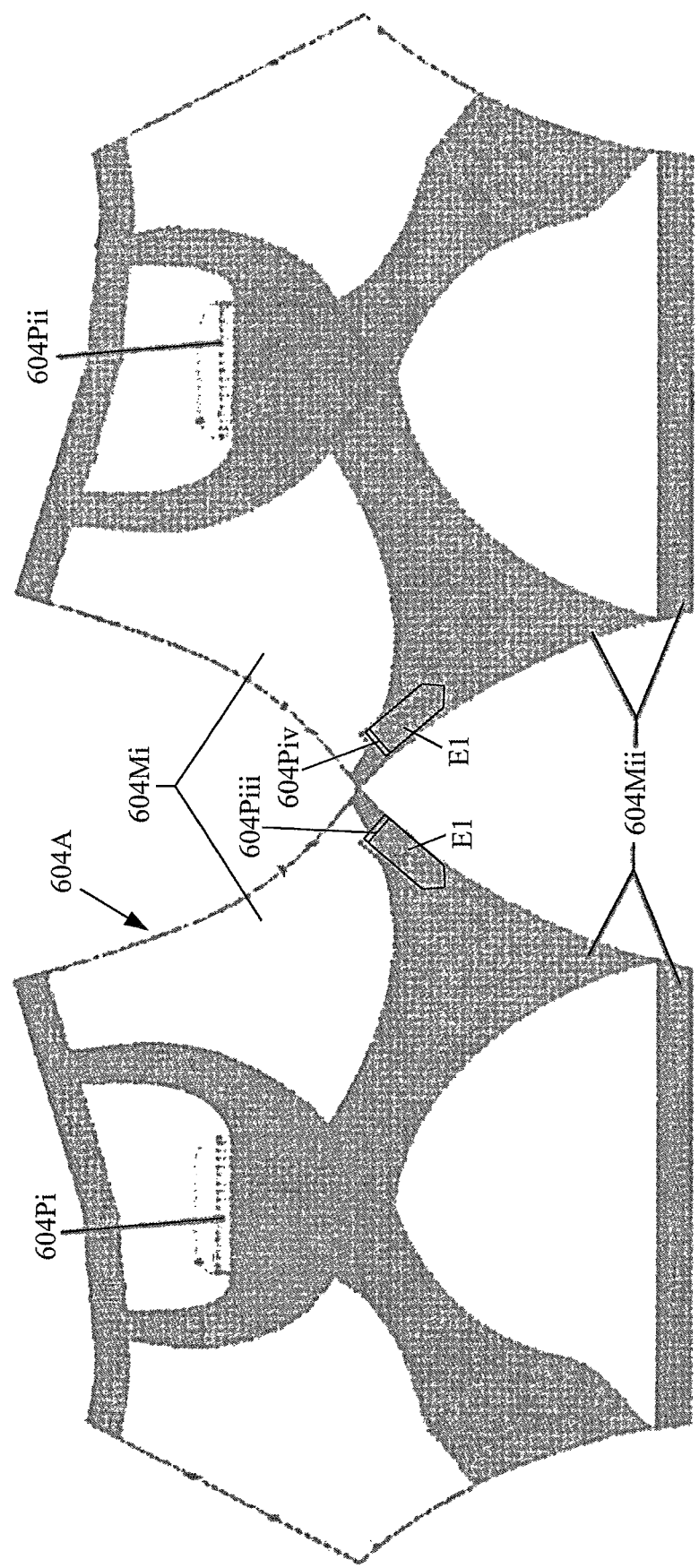
Figure 52E:
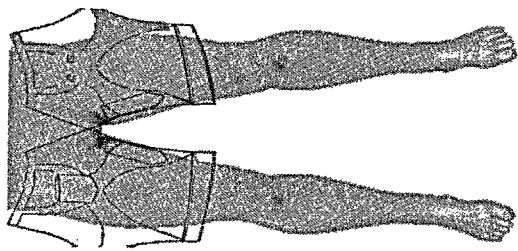
Figure 52D:
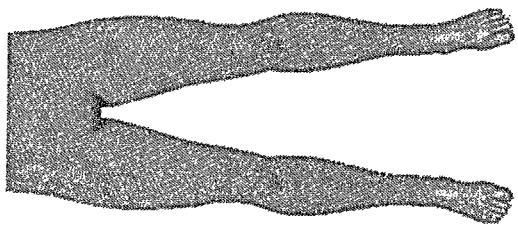
Figure 52C:
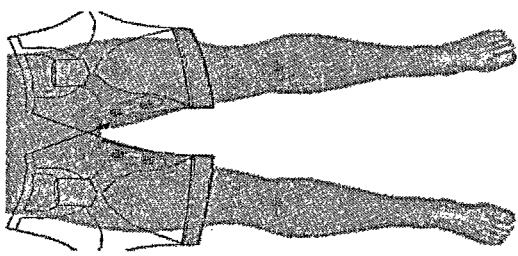
Figure 52B:
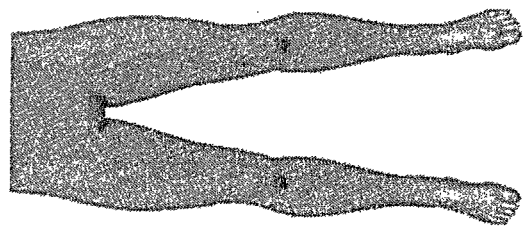
Figure 53:
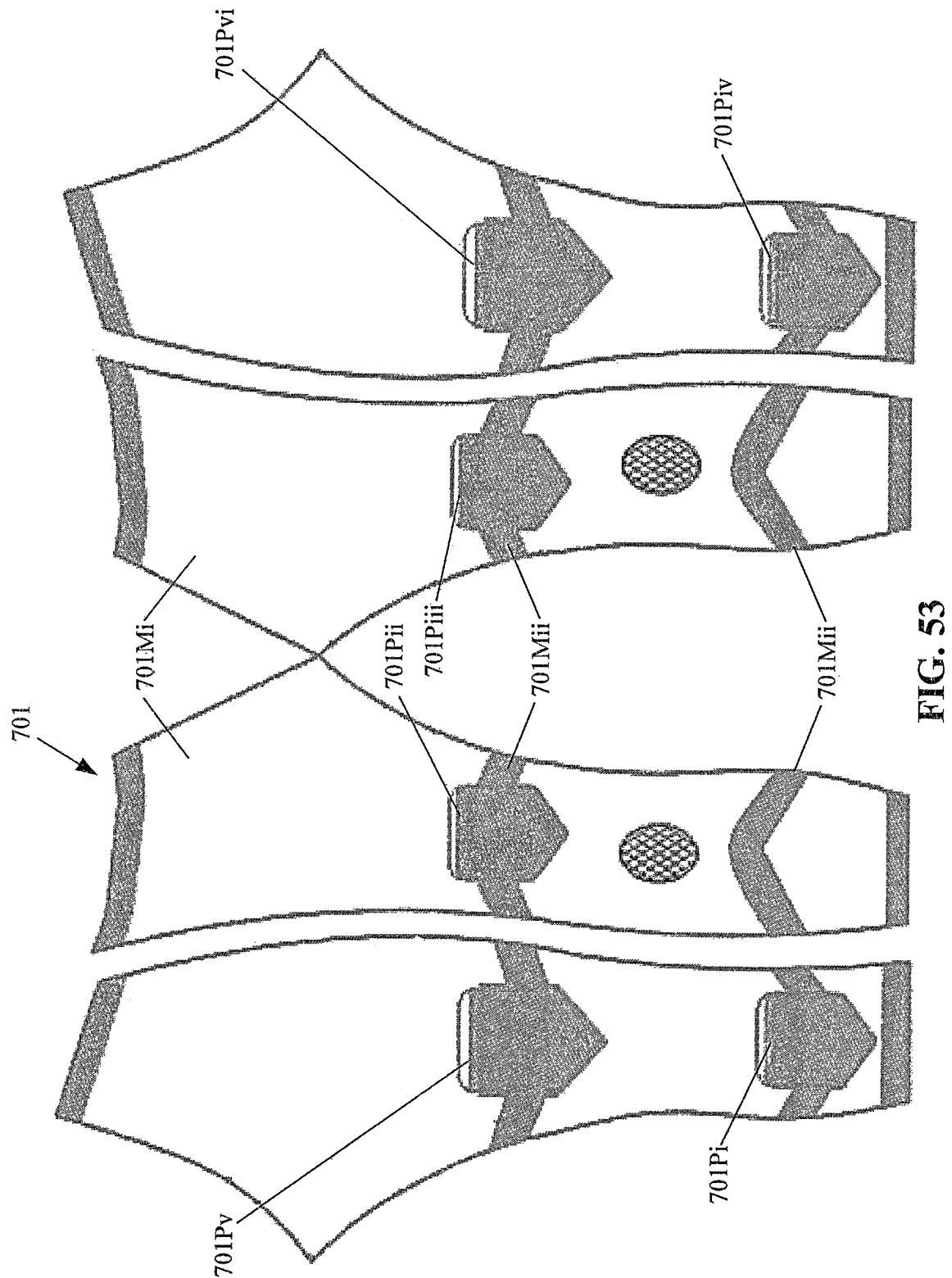
Figure 53A:
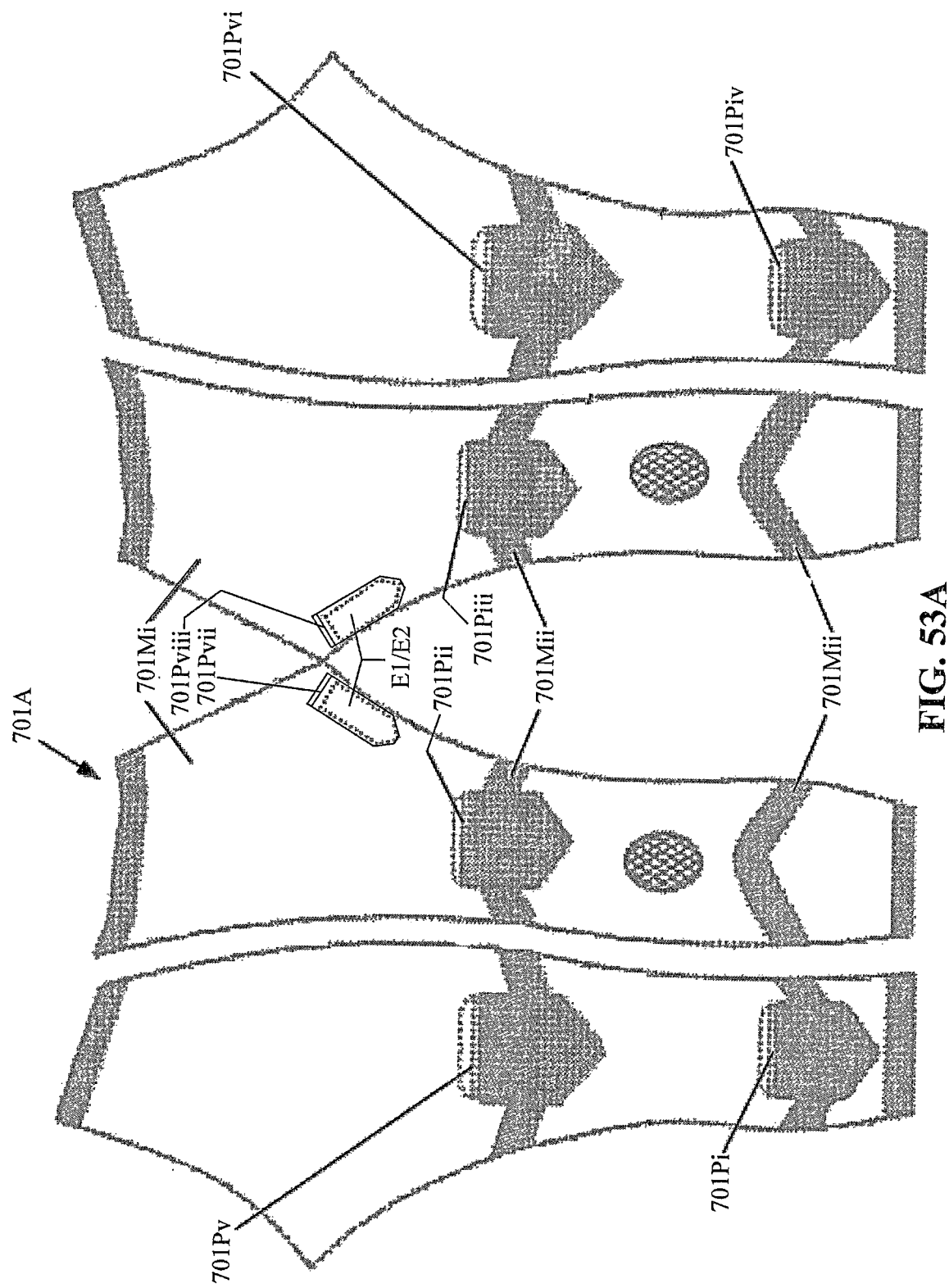
Figure 53B:
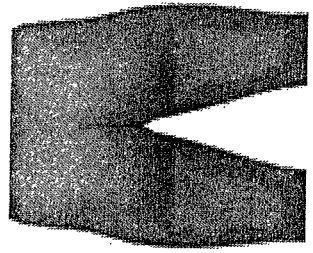
Figure 53C:
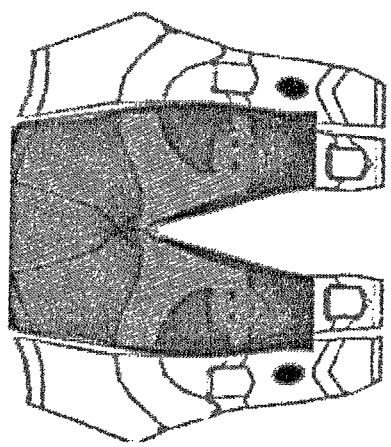
Figure 53D:
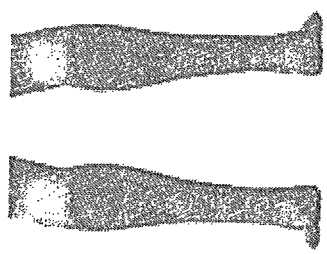
Figure 53E:
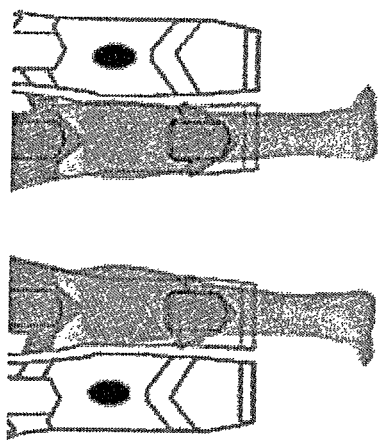
Figure 53I:
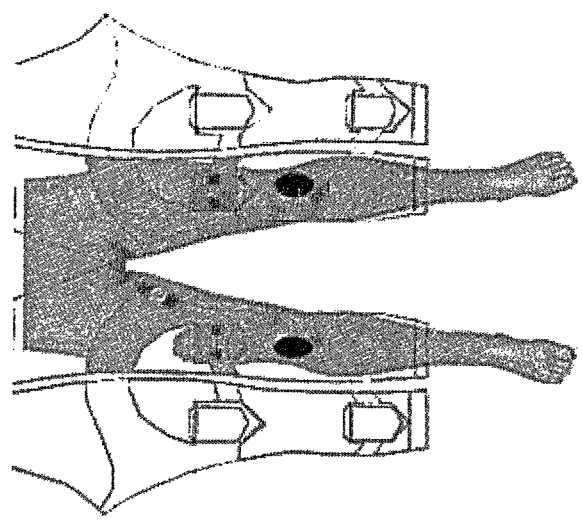
Figure 53H:
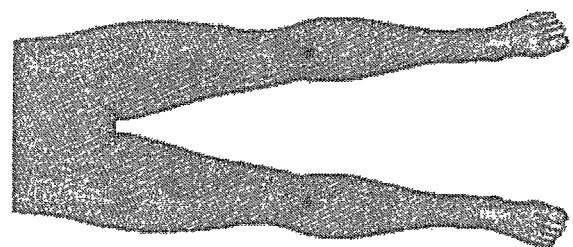
Figure 53G:
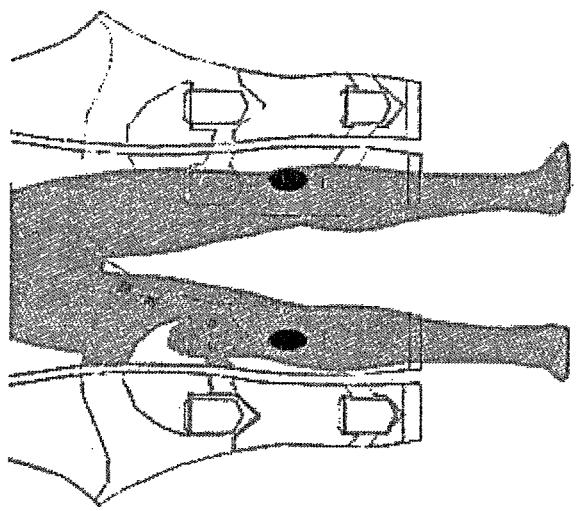
Figure 53F:
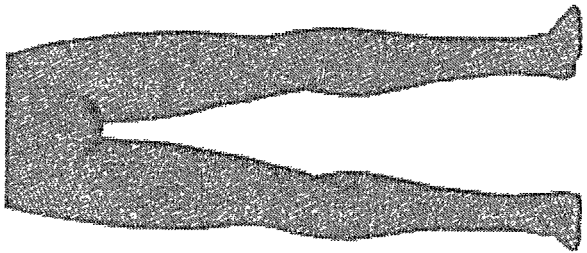
Figure 54:
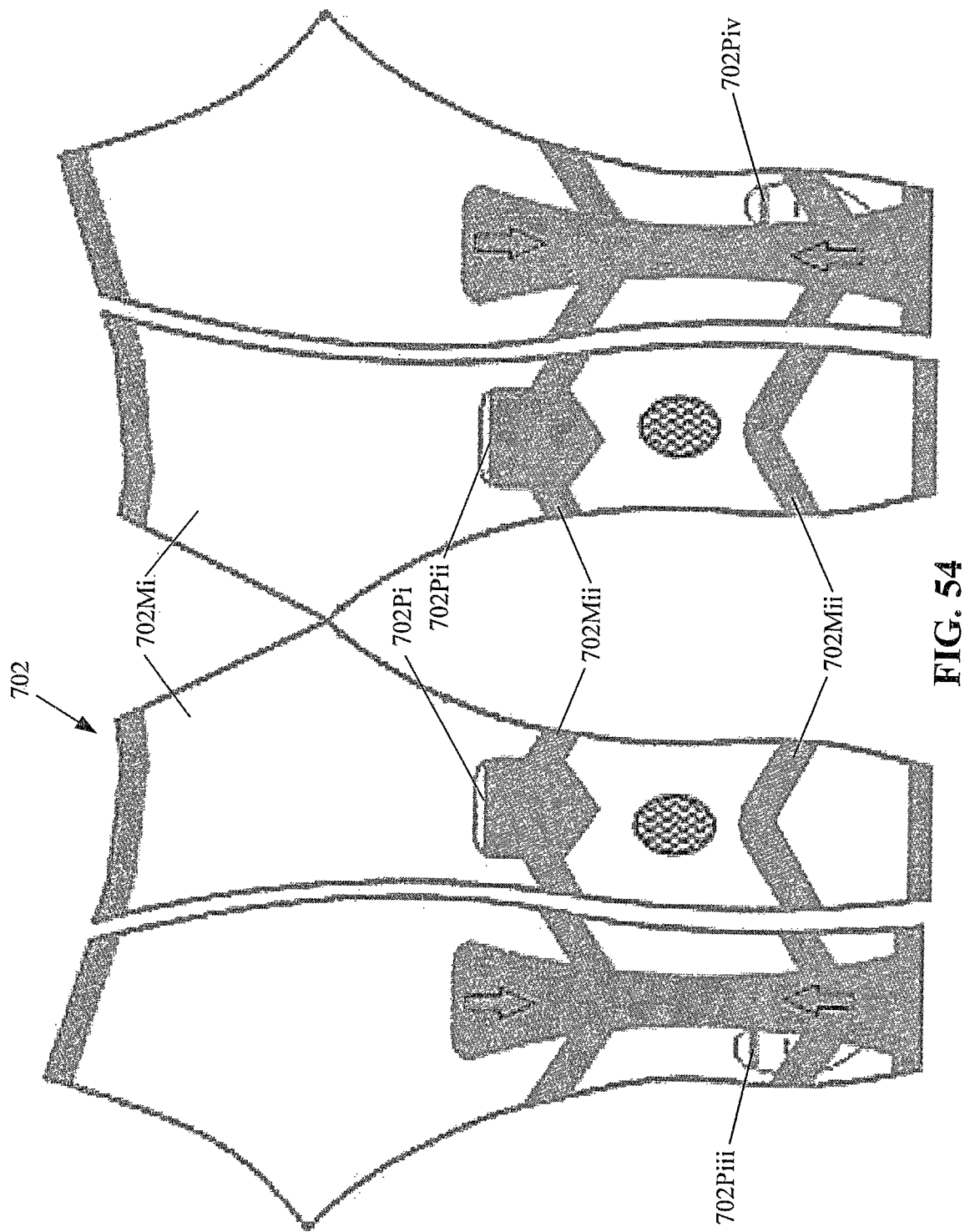
Figure 54A:
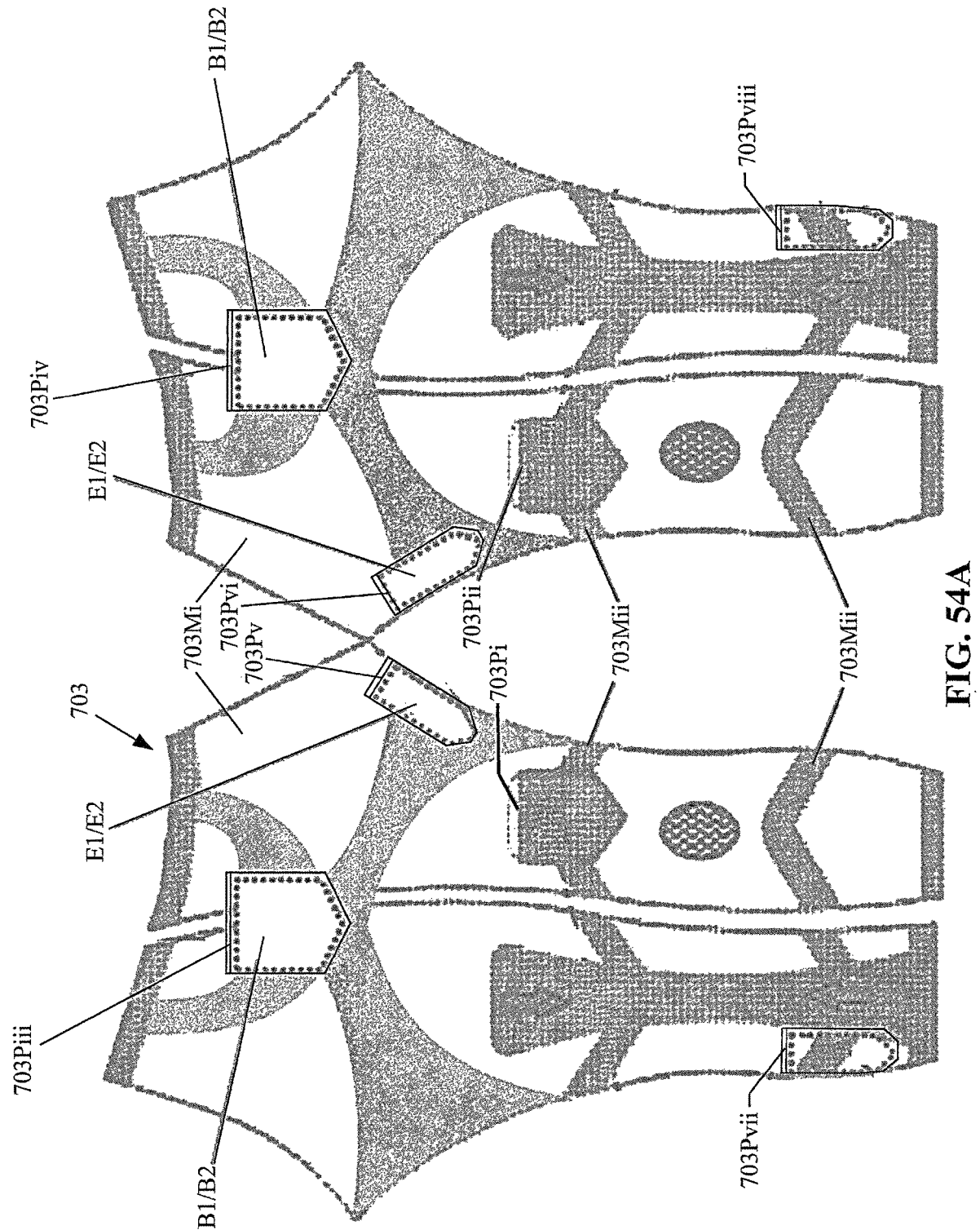
Figure 54C:
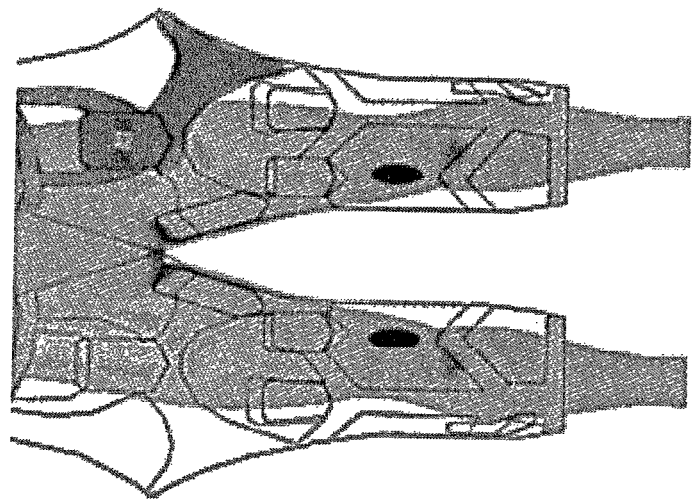
Figure 54B:
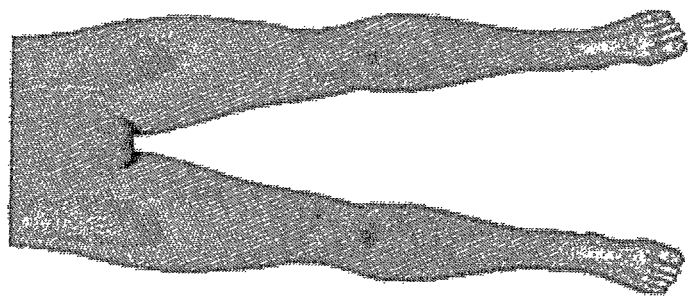
Figure 54G:
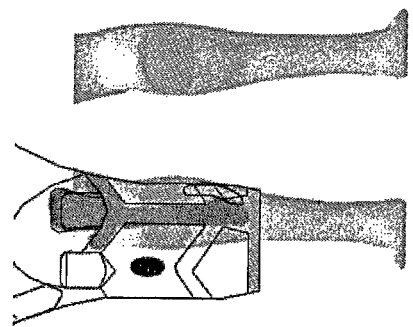
Figure 54F:
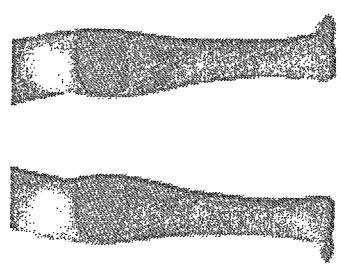
Figure 54E:
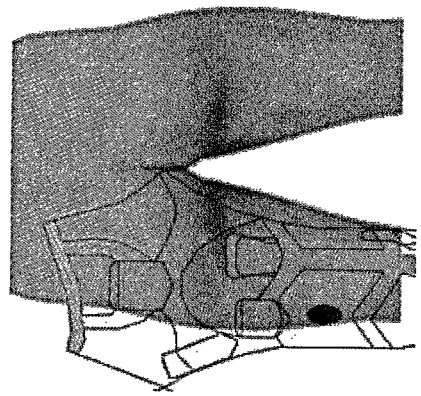
Figure 54D:
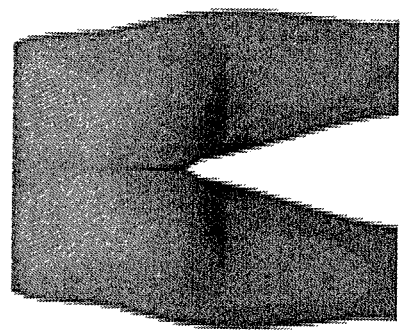
Figure 54K:
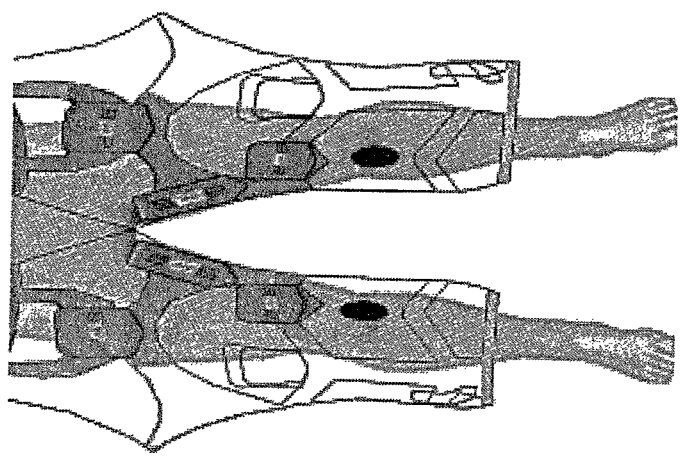
Figure 54J:
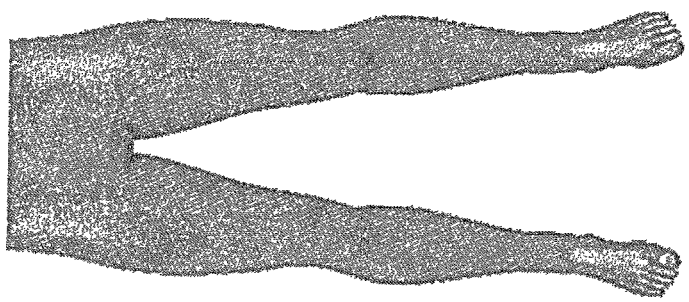
Figure 54I:
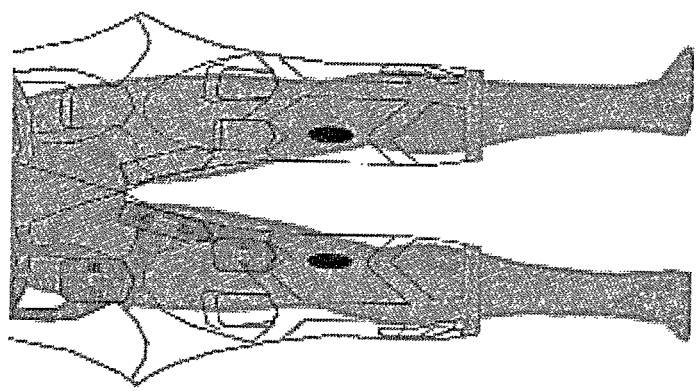
Figure 54H:
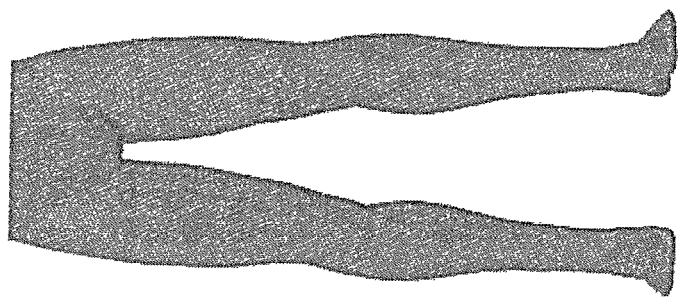
Figure 55:
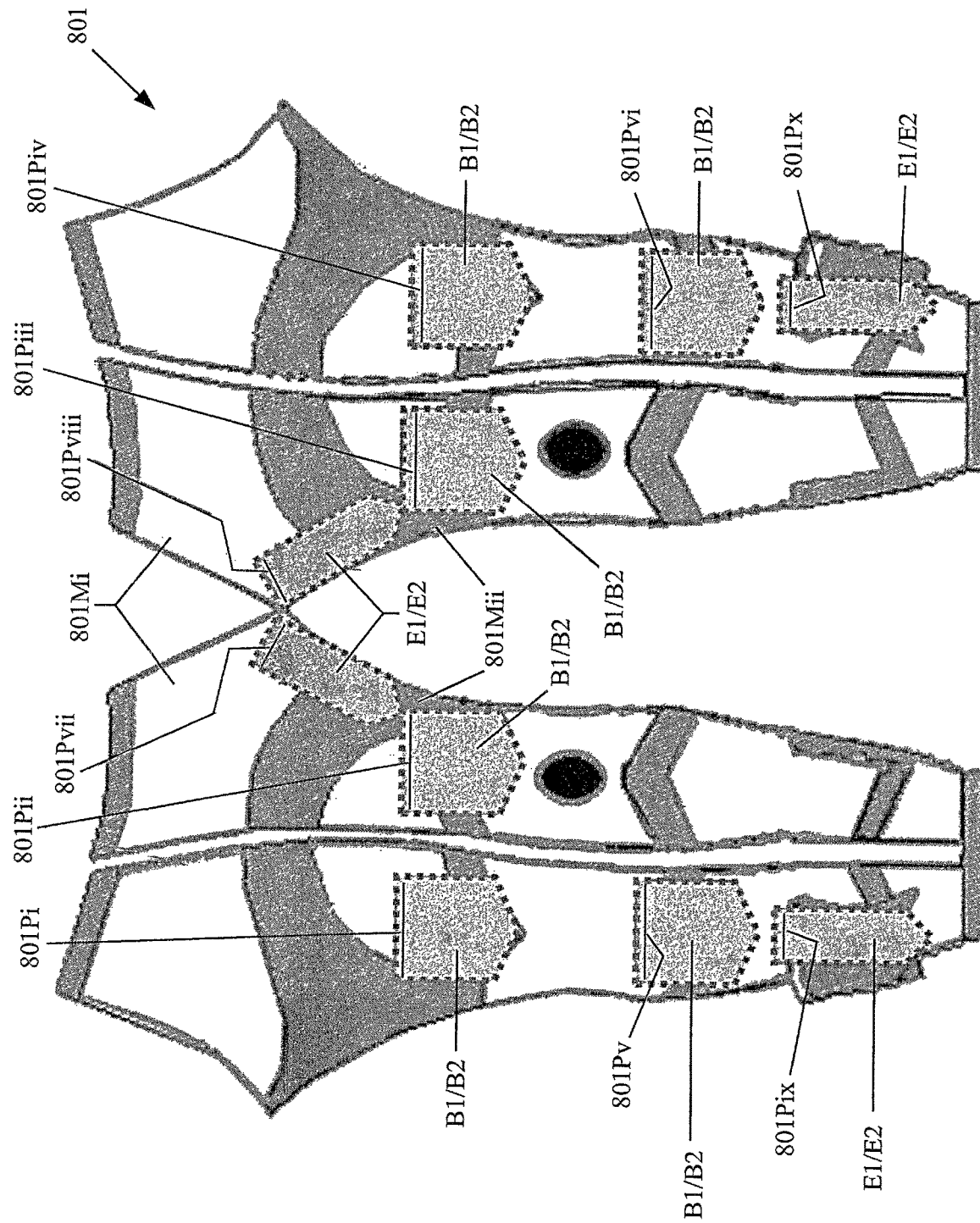
Figure 55H:
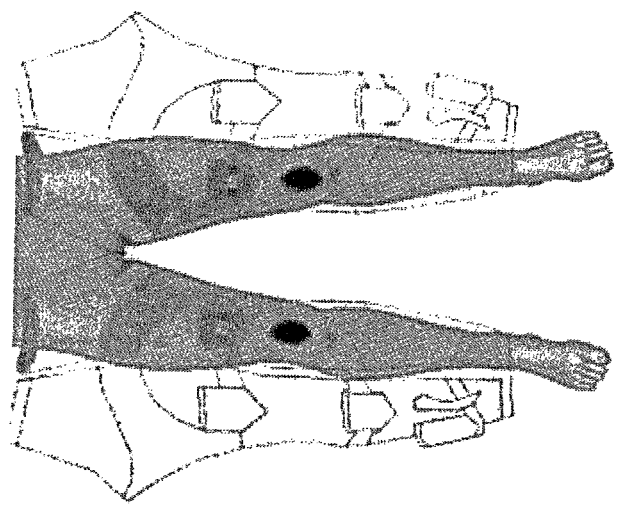
Figure 55G:
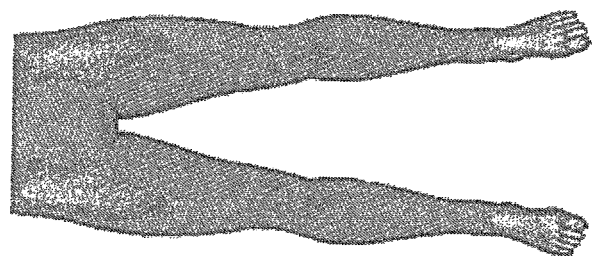
Figure 55F:
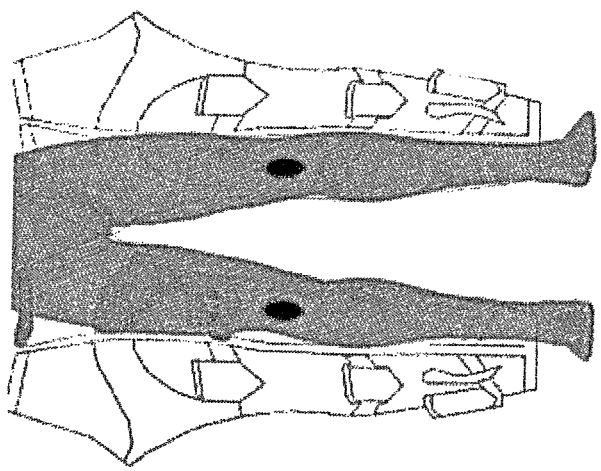
Figure 55E:
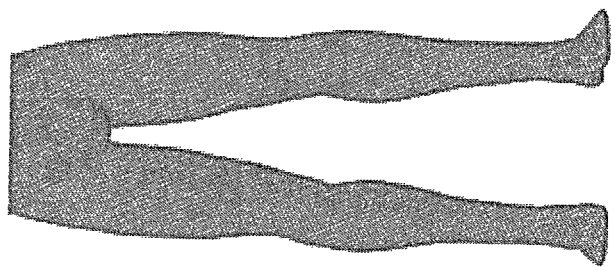
Figure 55J:
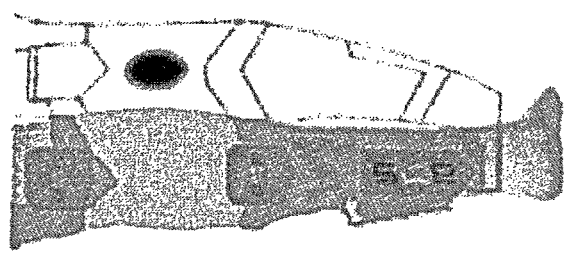
Figure 55I:
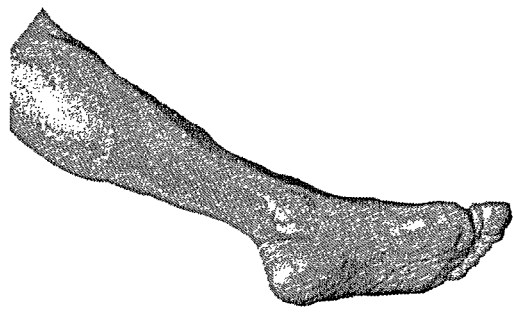
Figure 56:
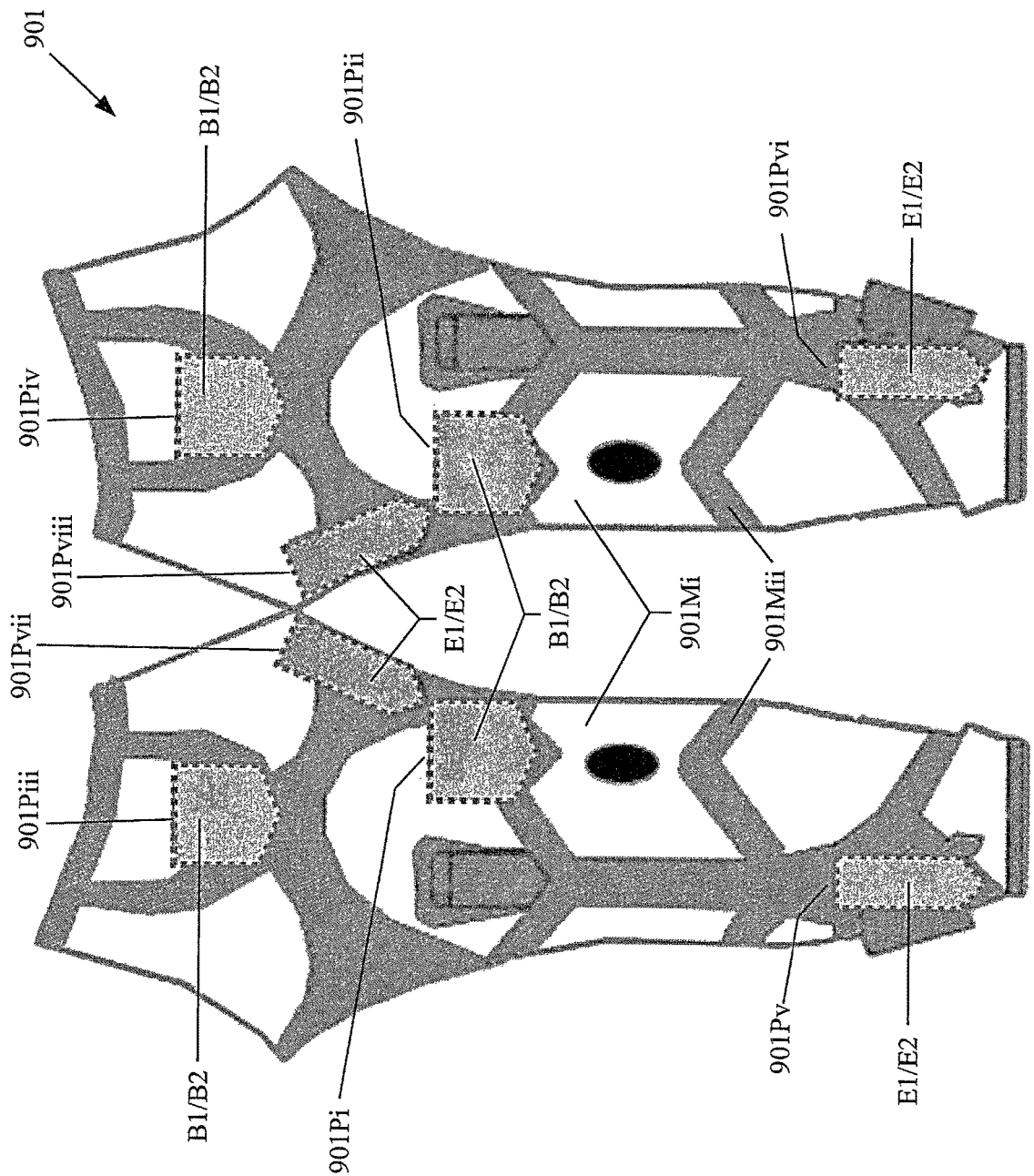
Figure 56B:
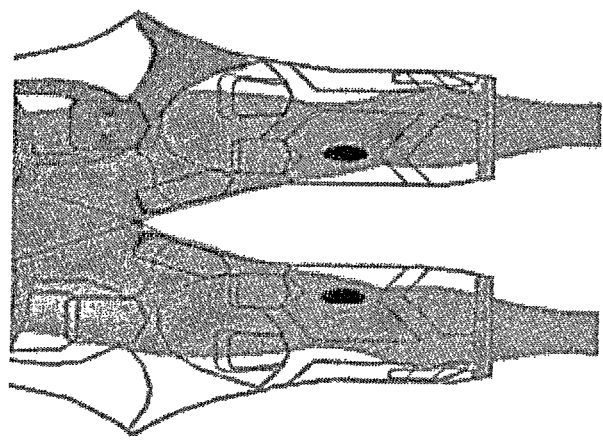
Figure 56A:
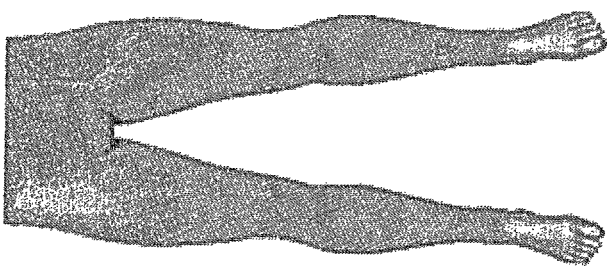
Figure 56F:
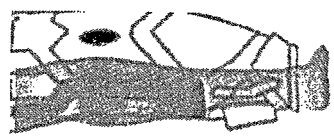
Figure 56E:
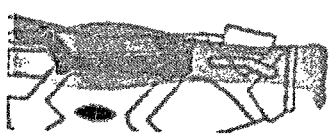
Figure 56D:
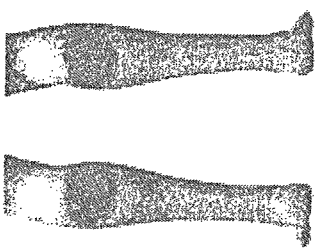
Figure 56C:
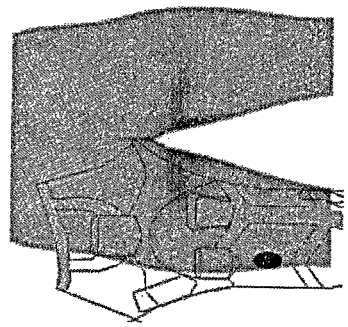
Figure 56J:
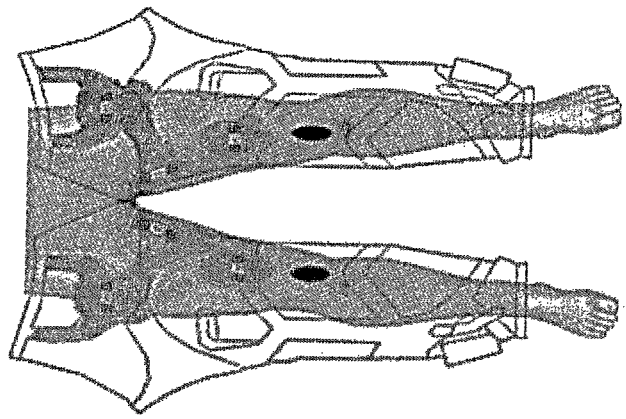
Figure 56I:
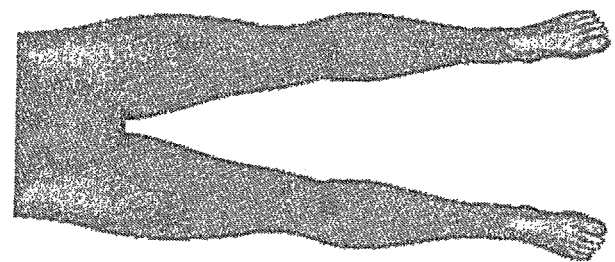
Figure 56H:
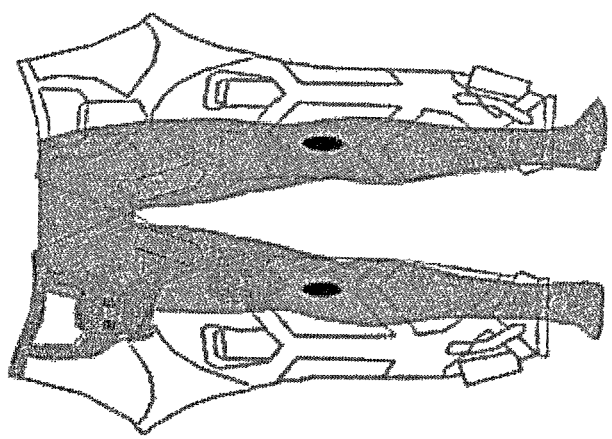
Figure 56G:
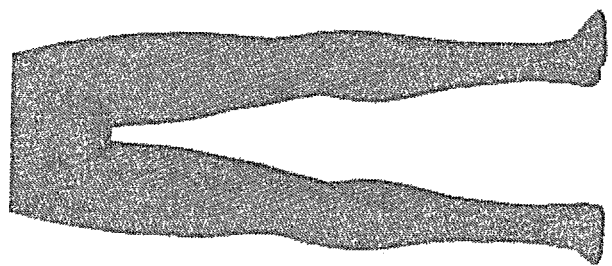
Figure 56L:
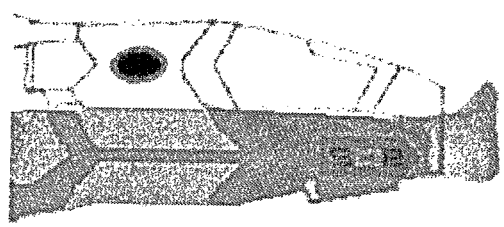
Figure 56K:
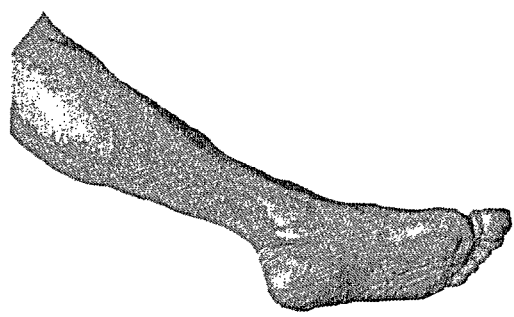
Figure 57:
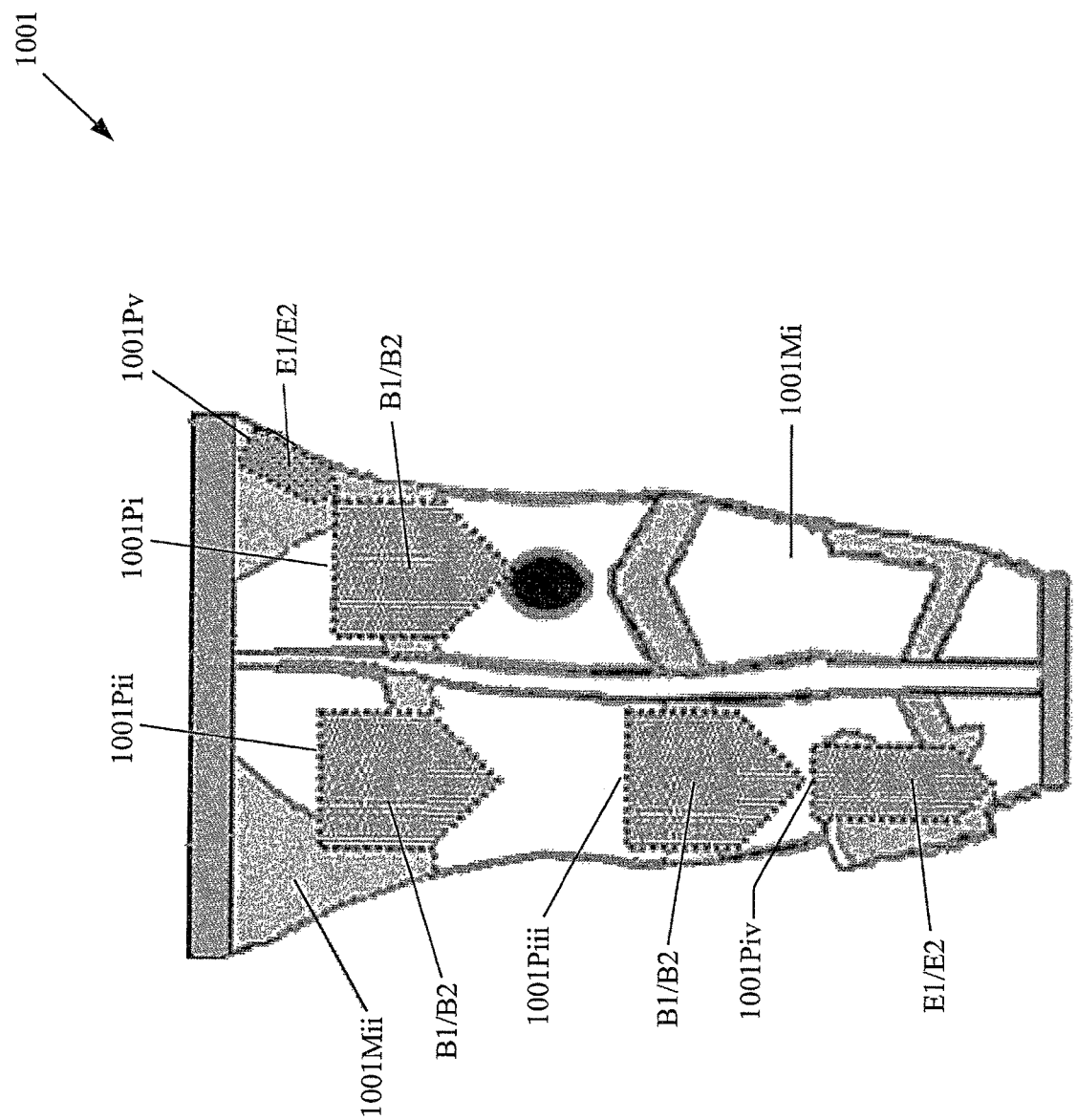
Figure 57D:
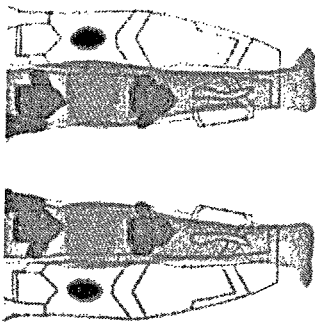
Figure 57C:
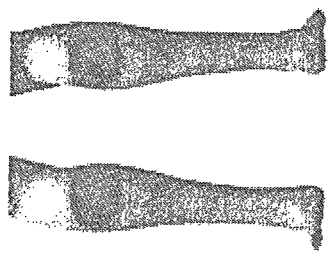
Figure 57B:
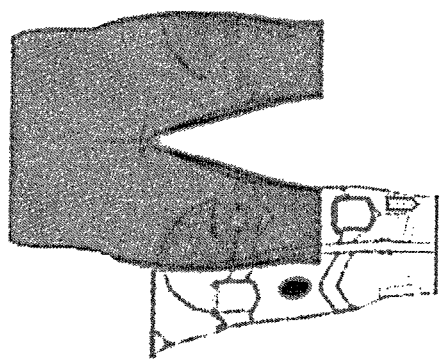
Figure 57A:
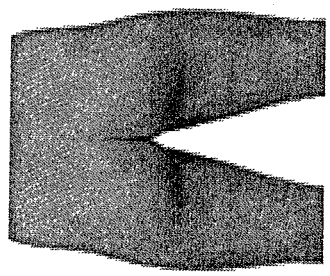
Figure 57H:
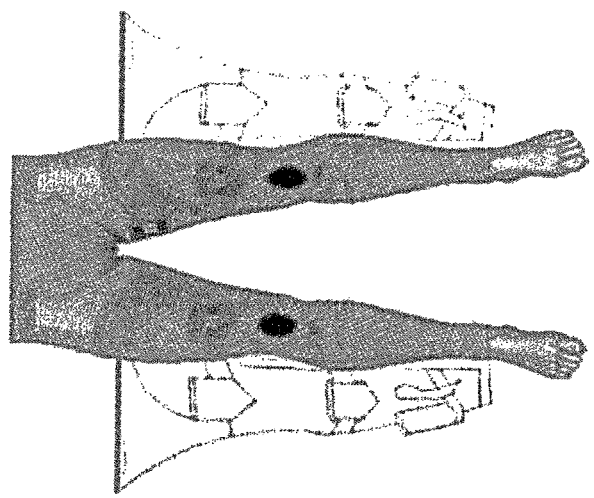
Figure 57G:
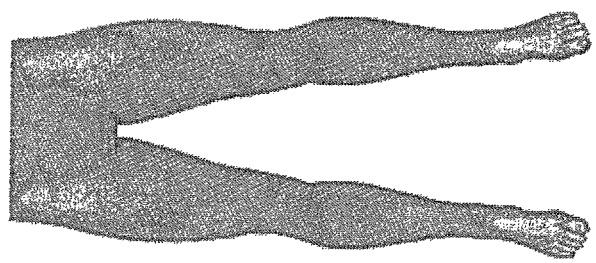
Figure 57F:
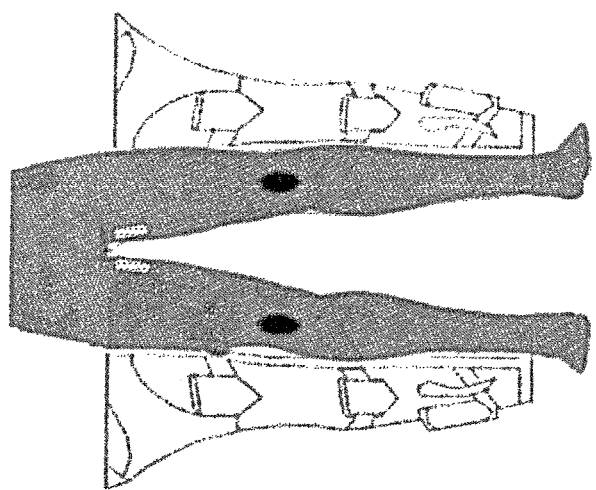
Figure 57E:
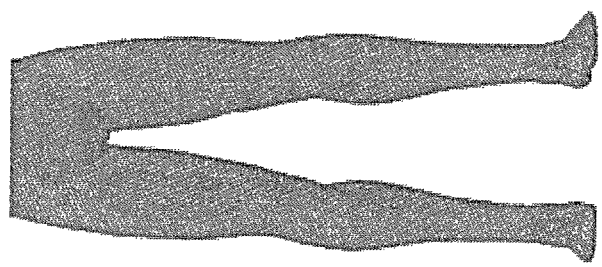
Figure 57J:
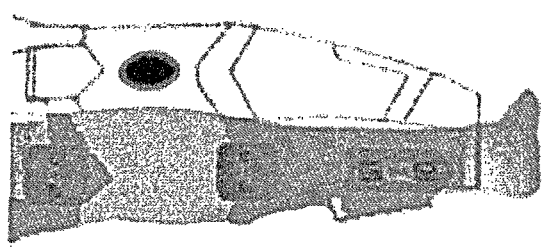
Figure 57I:
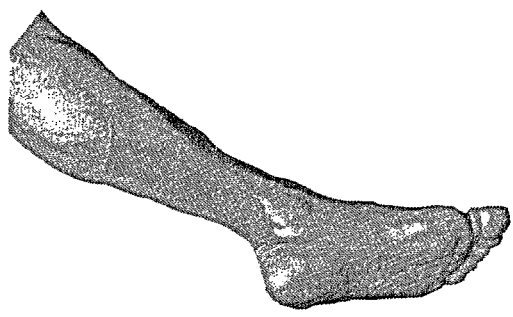
Figure 58:
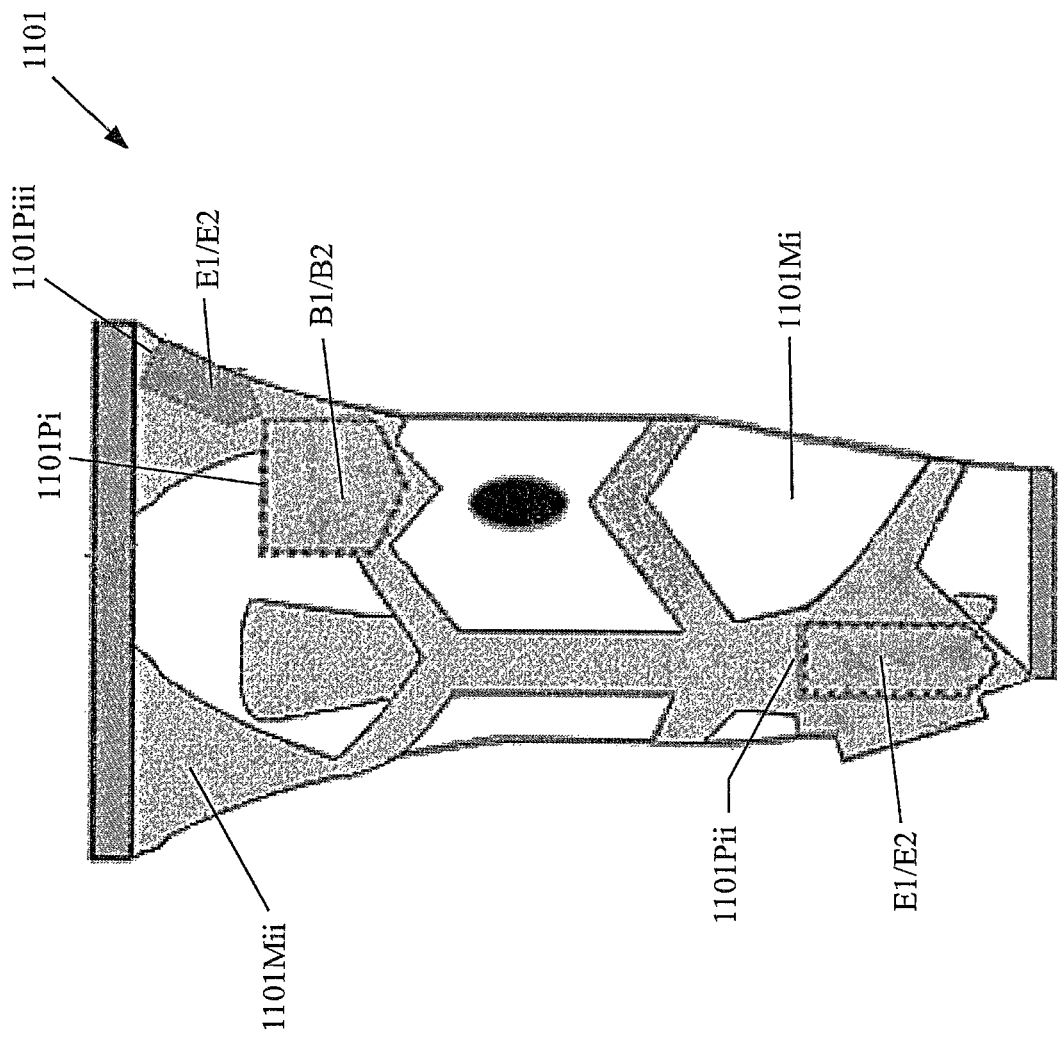
Figure 58D:
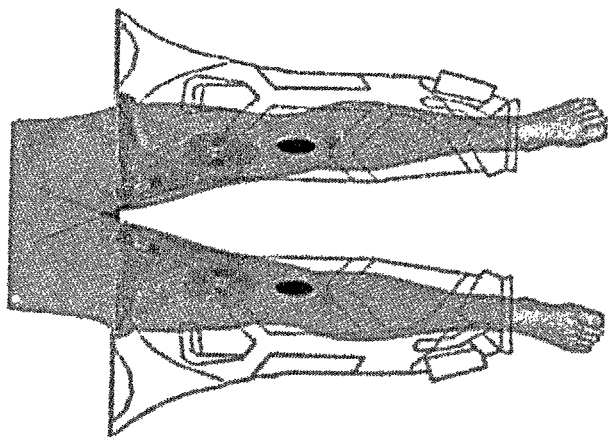
Figure 58C:
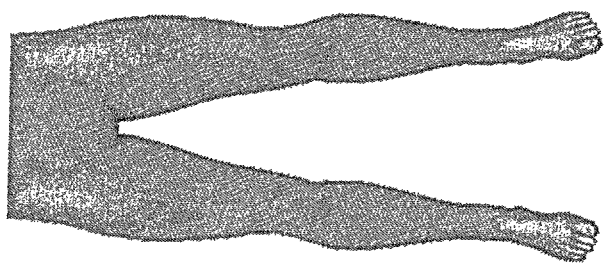
Figure 58B:
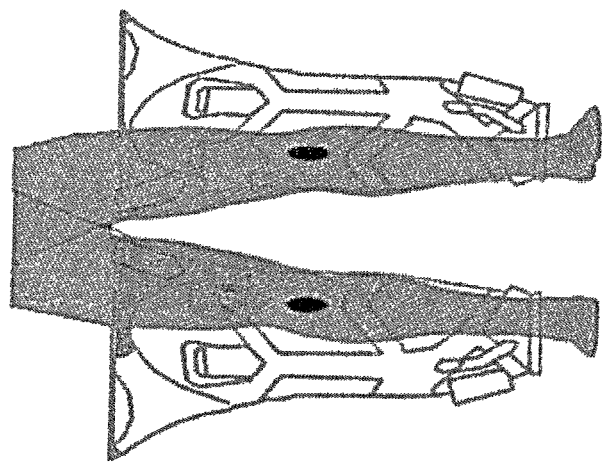
Figure 58A:
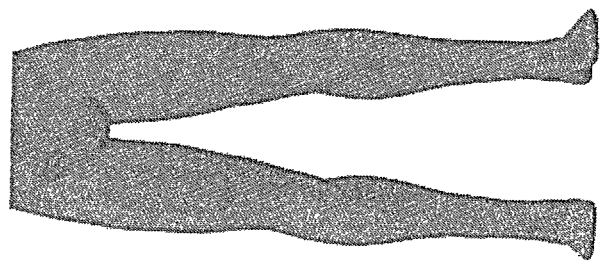
Figure 58F:
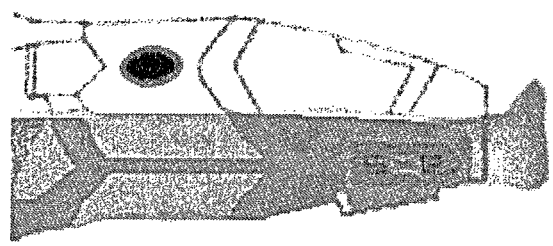
Figure 58E:
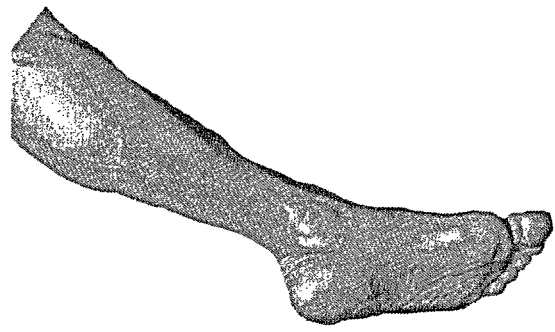
Figure 58J:
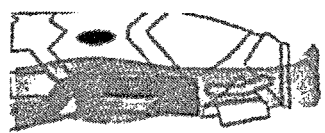
Figure 58I:
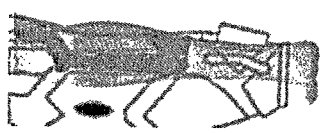
Figure 58H:
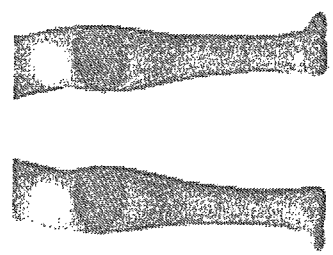
Figure 58G:
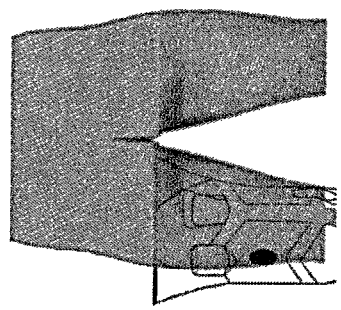
Figure 59:
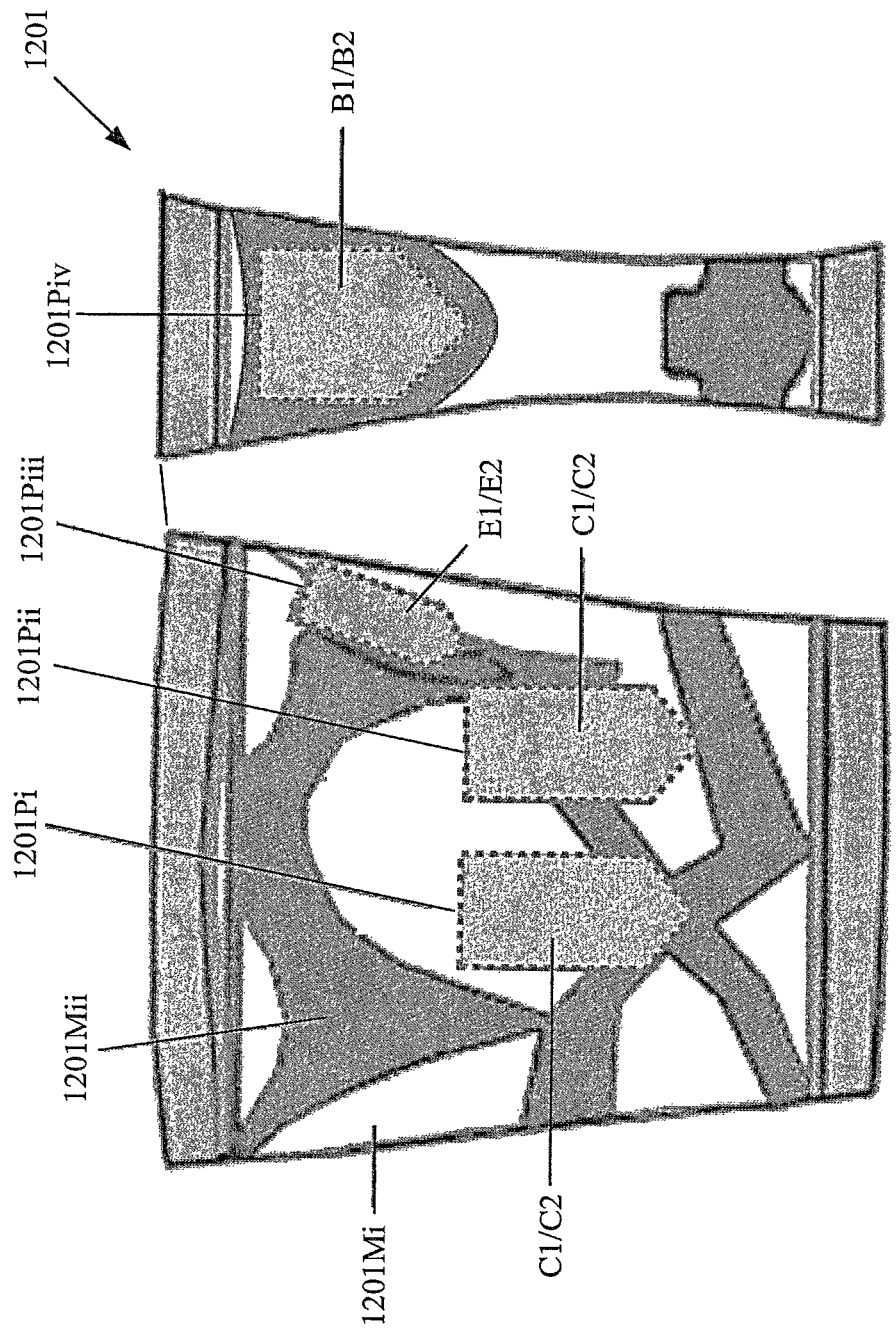
Figure 59D:
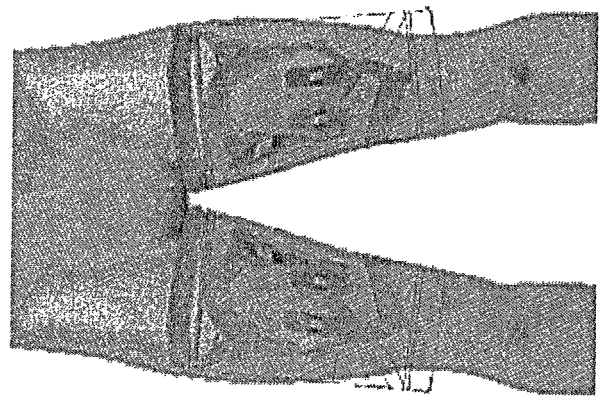
Figure 59C:
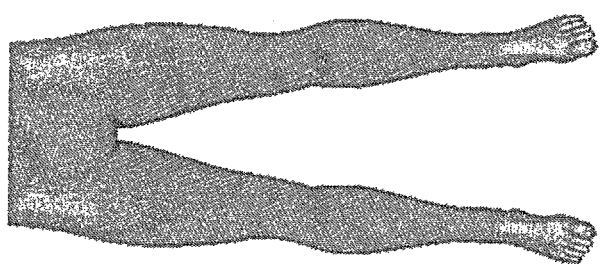
Figure 59B:
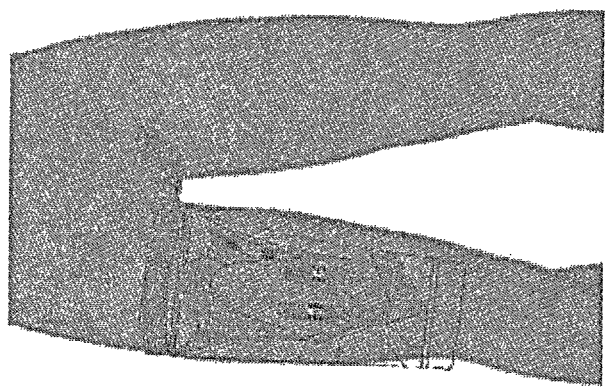
Figure 59A:
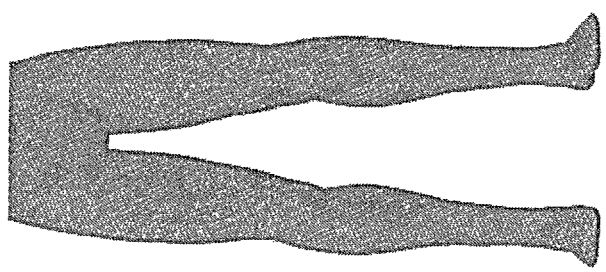
Figure 59F:
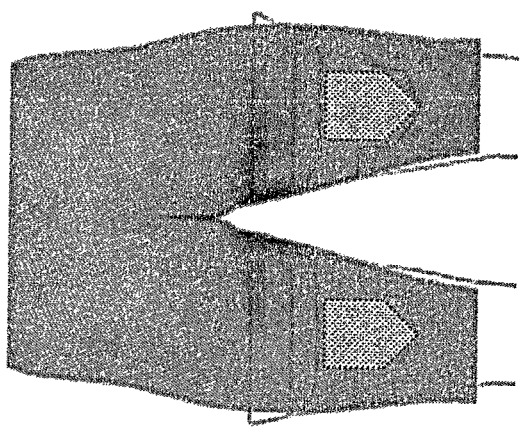
Figure 59E:
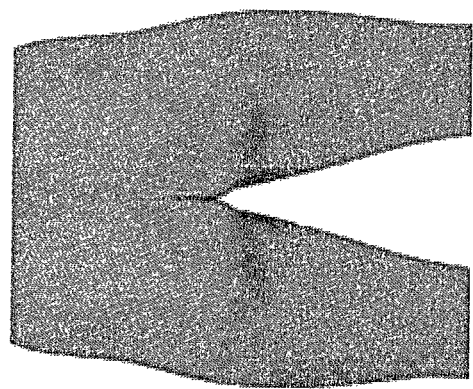
Figure 60:
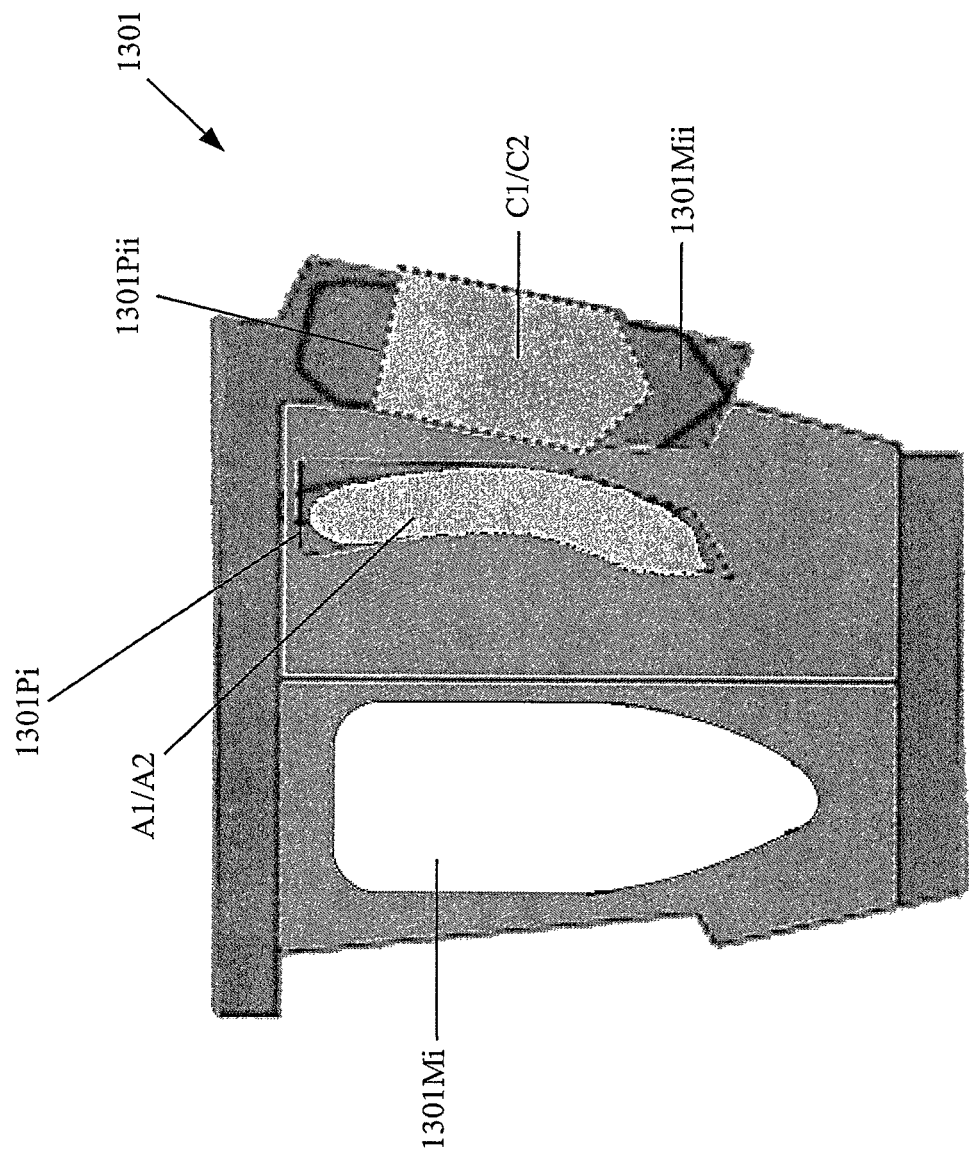
Figure 60B:
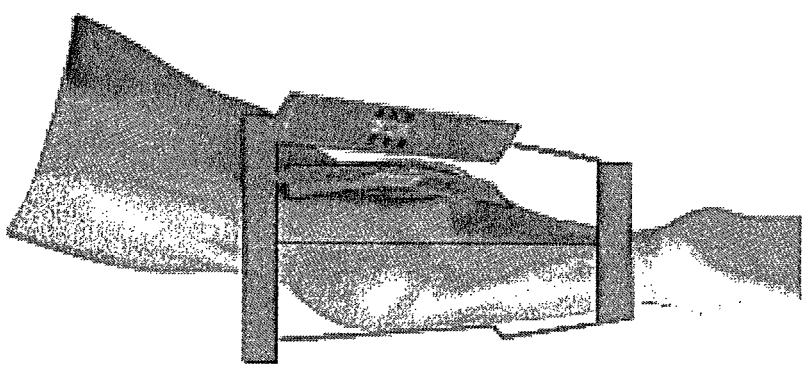
Figure 60A:
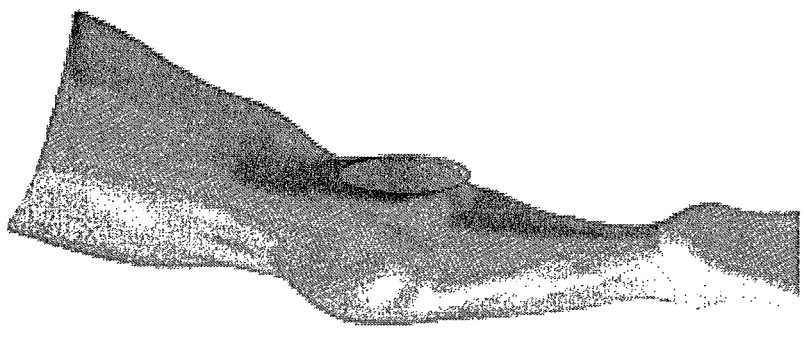

36, showing the locations of the high compression material, prior to forming the openings;

FIG. 41 is the flat pattern of FIG. 39, showing the pocket locations that are configured to receive heat/cold packs;

FIG. 42 is the flat pattern of FIG. 40, showing the pocket locations that are configured to receive heat/cold packs;

FIG. 43 is a flat pattern of another embodiment of a compression garment configured as short-length pants for a younger wearer, with openings formed to receive heat/cold packs into pockets therein to apply heat and/or cold therapy under compression to treat younger people;

FIG. 43A is a flat pattern of another embodiment of a compression garment configured as short-length pants for a younger wearer, being formed the same as the flat pattern in FIG. 43, but which has two additional pockets located at the groin area;

FIG. 43B is an image showing the front high quad/hip and flexor/pointer regions that may be treated using the short-length pants compression of FIG. 43A;

FIG. 43C shows the flat pattern of the short pants compression of FIG. 43A overlaid on a portion of a wearer's body, illustrating thermal treatment being provided to quad and hamstring muscles of the wearer's right leg, and the application of compression;

FIG. 43D is an image showing the front high adductor muscles that may be treated using the short-length pants compression of FIG. 43A;

FIG. 43E shows the flat pattern of the short pants compression of FIG. 43A overlaid on portions of a wearer's body, illustrating thermal treatment being provided to the quad muscles of both legs, and the application of compression;

FIG. 43F is an image showing the back high hamstring muscles that may be treated using the short-length pants compression of FIG. 43A;

FIG. 43G shows the flat pattern of the short pants compression of FIG. 43A overlaid on a portions of a wearer's body, illustrating thermal treatment being provided to the hamstring muscles of the left and right legs, and the application of compression;

FIG. 44 is a front view of a compression garment configured as short-length pants for an older wearer, with openings formed to receive heat/cold packs into pockets therein to apply heat and/or cold therapy under compression to treat older people with hip-related and leg-related muscle issues, shown after being donned by a wearer;

FIG. 45 is a rear view of a compression garment configured as short-length pants shown in FIG. 44;

FIG. 46 is a first view of a flat pattern usable to make the front side of the compression garment as shown in FIG. 44, showing the openings;

FIG. 47 is a first view of a flat pattern usable to make the rear side of the compression garment as shown in FIG. 45, showing the openings;

FIG. 48 is a second view of the flat pattern usable to make the front side of the compression garment as shown in FIG. 44, showing the locations of the high compression material, prior to forming the openings;

FIG. 49 is a second view of the flat pattern usable to make the rear side of the compression garment as shown in FIG. 45, showing the locations of the high compression material, prior to forming the openings;

FIG. 50 is the flat pattern of FIG. 48, showing the pocket locations that are configured to receive heat/cold packs;

FIG. 51 is the flat pattern of FIG. 49, showing the pocket locations that are configured to receive heat/cold packs;

FIG. 52 is a flat pattern of another embodiment of a compression garment configured as short-length pants for an older wearer, with openings formed to receive heat/cold packs into pockets therein to apply heat and/or cold therapy under compression to treat older people;

FIG. 52A is a flat pattern of another embodiment of a compression garment configured as short-length pants for an older wearer, being formed similar to the flat pattern in FIG. 52, having the same two pockets for heat packs for the left and right hips, and with two other pockets located at the left and right groin areas;

FIG. 52B is an image showing the Adductor Magnus muscle and Longus (groin) Muscle Groups that may be treated using the short-length pants compression of FIG. 52A;

FIG. 52C shows the flat pattern of the short pants compression of FIG. 52A overlaid on a portion of a wearer's body, illustrating thermal treatment being provided to the Longus (groin) muscles, and the application of compression;

FIG. 52D is an image showing that treatment of the Gluteus Medius muscles and treatment of Greater Trochanteric Bursitis/ITB Snapping may be accomplished using the short-length pants compression of FIG. 52A;

FIG. 52E shows the flat pattern of the short pants compression of FIG. 52A overlaid on a portion of a wearer's body, illustrating thermal treatment being provided to the left hip of the wearer, and the application of compression;

FIG. 53 is a flat pattern of another embodiment of a compression garment configured as mid-length pants for a younger wearer, with openings formed to receive heat/cold packs into pockets therein to apply heat and/or cold therapy under compression to treat younger people;

FIG. 53A is a flat pattern of another embodiment of a compression garment configured as mid-length pants for a younger wearer, being formed the same as the flat pattern in FIG. 53, but with two additional pockets located at the left and right groin areas;

FIG. 53B is an image showing hamstring muscle belly that may be treated using the mid-length pants compression of FIG. 53A;

FIG. 53C shows the flat pattern of the mid-length pants compression of FIG. 53A overlaid on a portion of a wearer's body, illustrating thermal treatment being provided to the left and right hamstring muscles, and the application of compression;

FIG. 53D is an image showing that Gastrocnemius (Tennis Leg) may be treated using the mid-length pants compression of FIG. 43A;

FIG. 53E shows the flat pattern of the mid-length pants compression of FIG. 53A overlaid on a portion of a wearer's body, illustrating the application of compression for treatment of Gastrocnemius (Tennis Leg);

FIG. 53F is an image showing that the front high quad/hip and flexor/pointer regions may be treated using the mid-length pants compression of FIG. 53A;

FIG. 53G shows the flat pattern of the mid-length pants compression of FIG. 53A overlaid on a portion of a wearer's body, illustrating thermal treatment being provided to quad and groin muscles on the right side of the wearer, and the application of compression;

FIG. 53H is an image showing that the Adductor Magnus and Longus (groin) Muscle Groups may be treated using the mid-length pants compression of FIG. 52A;

FIG. 53I shows the flat pattern of the mid-length pants compression of FIG. 53A overlaid on a portion of a wearer's body, illustrating thermal treatment being provided to quad and groin muscles on the right side of the wearer, and to the quad muscles on the left side of the wearer, and the application of compression;

FIG. 54 is a flat pattern of another embodiment of a compression garment configured as mid-length pants for an older wearer, with openings formed to receive heat/cold packs into pockets therein to apply heat and/or cold therapy under compression to treat older people;

FIG. 54A is a flat pattern of another mid-length pants compression garment configured as for an older wearer, being formed similar to the flat pattern in FIG. 54, having two pockets for heat packs for the left and right quads, different shaped pockets and heat packs located at each calf area, and with two additional pockets for heat packs for the left and right hips, and two additional pockets located at the left and right groin areas;

FIG. 54B is an image showing that treatment of the Gluteus Medius muscles and treatment of Greater Trochanteric Bursitis/ITB Snapping may be accomplished using the mid-length pants compression of FIG. 54A;

FIG. 54C shows the flat pattern of the mid-length pants compression of FIG. 54A overlaid on a portion of a wearer's body, illustrating thermal treatment being provided to the left hip and the application of compression;

FIG. 54D is an image showing hamstring muscle belly that may be treated using the mid-length pants compression of FIG. 54A;

FIG. 54E shows the flat pattern of the mid-length pants compression of FIG. 54A overlaid on a portion of a wearer's body, illustrating the application of compression for treating hamstring muscle belly;

FIG. 54F is an image showing that Gastrocnemius (Tennis Leg) may be treated using the mid-length pants compression of FIG. 54A;

FIG. 54G shows the flat pattern of the mid-length pants compression of FIG. 54A overlaid on a portion of a wearer's body, illustrating the application of compression for treating Gastrocnemius (Tennis Leg);

FIG. 54H is an image showing the front high quad/hip and flexor/pointer regions that may be treated using the mid-length pants compression of FIG. 54A;

FIG. 54I shows the flat pattern of the mid-length pants compression of FIG. 54A overlaid on a portion of a wearer's body, illustrating thermal treatment being provided to the quad, groin, and hip muscles on the right side of the wearer, and the application of compression;

FIG. 54J is an image showing that the Adductor Magnus muscle and Longus (groin) Muscle Groups may be treated using the mid-length pants compression of FIG. 54A;

FIG. 54K shows the flat pattern of the mid-length pants compression of FIG. 54A overlaid on a portion of a wearer's body, illustrating thermal treatment being provided to quad, groin, and hip muscles on the left and right sides of the wearer, and the application of compression;

FIG. 55 is a flat pattern of another compression garment configured as full-length pants for use by a younger wearer, with openings formed to receive heat/cold packs into pockets therein to apply heat and/or cold therapy under compression;

FIG. 55A is an image showing hamstring muscle belly that may be treated using the full-length pants compression of FIG. 55;

FIG. 55B shows the flat pattern of the full-length pants compression of FIG. 55 overlaid on a portion of a wearer's body, illustrating thermal treatment being provided to the left and right quad muscles, and the application of compression for treating hamstring muscle belly;

FIG. 55C is an image showing that Gastrocnemius (Tennis Leg) may be treated using the full-length pants compression of FIG. 55;

FIG. 55D shows the flat pattern of the full-length pants compression of FIG. 55 overlaid on a portion of a wearer's body, illustrating the application of compression for treating Gastrocnemius (Tennis Leg);

FIG. 55E is an image showing the front high quad/hip and flexor/pointer regions that may be treated using the full-length pants compression of FIG. 55;

FIG. 55F shows the flat pattern of the full-length pants compression of FIG. 55 overlaid on a portion of a wearer's body, illustrating thermal treatment being provided to quad muscles on the right side of the wearer, and the application of compression;

FIG. 55G is an image showing that the Adductor Magnus muscle and Longus (groin) Muscle Groups may be treated using the full-length pants compression of FIG. 55;

FIG. 55H shows the flat pattern of the full-length pants compression of FIG. 55 overlaid on a portion of a wearer's body, illustrating thermal treatment being provided to quad muscles on the left and right sides of the wearer, and the application of compression;

FIG. 55I is an image showing that Achilles sprain or pain may be treated using the full-length pants compression of FIG. 55;

FIG. 55J shows the flat pattern of the full-length pants compression of FIG. 55 overlaid on a portion of a wearer's body, illustrating thermal treatment being provided to the hamstring and calf muscles and Achilles tendon on one leg of the wearer, and the application of compression;

FIG. 56 is a flat pattern of another compression garment configured as full-length pants for use by an older wearer, with openings formed to receive heat/cold packs into pockets therein to apply heat and/or cold therapy under compression;

FIG. 56A is an image showing that treatment of tendinitis of the Gluteus Medius muscles and treatment of Greater Trochanteric Bursitis/ITB Snapping may be accomplished using the full-length pants compression of FIG. 56;

FIG. 56B shows the flat pattern of the full-length pants compression of FIG. 56 overlaid on a portion of a wearer's body, illustrating thermal treatment being provided to the left hip and the application of compression;

FIG. 56C is an image showing that hamstring muscle belly may be treated using the full-length pants compression of FIG. 56;

FIG. 56D shows the flat pattern of the full-length pants compression of FIG. 56 overlaid on a portion of a wearer's body, illustrating the application of compression for treating hamstring muscle belly;

FIG. 56E is an image showing that Gastrocnemius (Tennis Leg) may be treated using the full-length pants compression of FIG. 56;

FIG. 56F shows the flat pattern of the full-length pants compression of FIG. 56 overlaid on a portion of a wearer's body, illustrating the application of compression for treating Gastrocnemius (Tennis Leg);

FIG. 56G is an image showing the front high quad/hip and flexor/pointer regions that may be treated using the full-length pants compression of FIG. 56;

FIG. 56H shows the flat pattern of the full-length pants compression of FIG. 56 overlaid on a portion of a wearer's body, illustrating thermal treatment being provided to the quad and hip muscles on the right side of the wearer, and the application of compression;

FIG. 56I is an image showing that the Adductor Magnus muscle and Longus (groin) Muscle Groups may be treated using the full-length pants compression of FIG. 56;

FIG. 56J shows the flat pattern of the full-length pants compression of FIG. 56 overlaid on a portion of a wearer's body, illustrating thermal treatment being provided to the quad, groin, and hip muscles on the left and right sides of the wearer, and the application of compression;

FIG. 56K is an image showing that Achilles sprain or pain may be treated using the full-length pants compression of FIG. 56;

FIG. 56L shows the flat pattern of the full-length pants compression of FIG. 56 overlaid on a portion of a wearer's body, illustrating thermal treatment being provided to the Achilles tendon on one leg of the wearer, and the application of compression;

FIG. 57 is a flat pattern of a full-leg compression garment configured for use by a younger wearer, with openings formed to receive heat/cold packs into pockets therein to apply heat and/or cold therapy under compression;

FIG. 57A is an image showing that hamstring muscle belly may be treated using the full-leg compression of FIG. 57;

FIG. 57B shows the flat pattern of the full-leg compression of FIG. 57 overlaid on a portion of a wearer's body, illustrating thermal treatment being provided to the left quad muscle and the application of compression for treating hamstring muscle belly;

FIG. 57C is an image showing that Gastrocnemius (Tennis Leg) may be treated using the full-leg compression of FIG. 57;

FIG. 57D shows the flat pattern of the full-leg compression of FIG. 57 overlaid on a left leg of a wearer's body and also the flat pattern of the full-leg compression of FIG. 57 overlaid on a right leg of a wearer's body, illustrating the application of compression for treating Gastrocnemius (Tennis Leg) on both legs;

FIG. 57E is an image showing the front high quad/hip and flexor/pointer regions that may be treated using the full-leg compression of FIG. 57;

FIG. 57F shows the flat pattern of the full-leg compression of FIG. 57 overlaid on a left leg of a wearer's body and also the flat pattern of the full-leg compression of FIG. 57 overlaid on a right leg of a wearer's body, illustrating thermal treatment being provided to the quad muscle on the right leg of the wearer, and the application of compression;

FIG. 57G is an image showing that the Adductor Magnus muscle and Longus (groin) Muscle Groups may be treated using the full-leg compression of FIG. 57;

FIG. 57H shows the flat pattern of the full-leg compression of FIG. 57 overlaid on a left leg of a wearer's body and also the flat pattern of the full-leg compression of FIG. 57 overlaid on a right leg of a wearer's body, illustrating thermal treatment being provided to the quad muscle on the left and right legs of the wearer, thermal treatment being provided to the left groin, and the application of compression;

FIG. 57I is an image showing that Achilles sprain or pain may be treated using the full-leg compression of FIG. 57;

FIG. 57J shows the flat pattern of the full-leg compression of FIG. 57 overlaid on a leg of a wearer's body, illustrating thermal treatment being provided to the hamstring and calf muscles and Achilles tendon, and the application of compression;

FIG. 58 is a flat pattern of a full-leg compression garment configured for use by an older wearer, with openings formed to receive heat/cold packs into pockets therein to apply heat and/or cold therapy under compression;

FIG. 58A is an image showing the front high quad/hip and flexor/pointer regions that may be treated using the full-leg compression of FIG. 58;

FIG. 58B shows the flat pattern of the full-leg compression of FIG. 58 overlaid on a left leg of a wearer's body and also the flat pattern of the full-leg compression of FIG. 58 overlaid on a right leg of a wearer's body, illustrating thermal treatment being provided to the quad muscle on the right leg of the wearer, and the application of compression;

FIG. 58C is an image showing that the Adductor Magnus muscle and Longus (groin) Muscle Groups may be treated using the full-leg compression of FIG. 58;

FIG. 58D shows the flat pattern of the full-leg compression of FIG. 58 overlaid on a left leg of a wearer's body and also the flat pattern of the full-leg compression of FIG. 58 overlaid on a right leg of a wearer's body, illustrating thermal treatment being provided to the quad muscle on the left and right legs of the wearer, thermal treatment being provided to the left and right groin muscles, and the application of compression;

FIG. 58E is an image showing that Achilles sprain or pain may be treated using the full-leg compression of FIG. 58;

FIG. 58F shows the flat pattern of the full-leg compression of FIG. 58 overlaid on a leg of a wearer's body, illustrating thermal treatment being provided to the Achilles tendon, and the application of compression;

FIG. 58G is an image showing that hamstring muscle belly may be treated using the full-leg compression of FIG. 58;

FIG. 58H shows the flat pattern of the full-leg compression of FIG. 58 overlaid on a portion of a wearer's body, illustrating the application of compression for treating hamstring muscle belly;

FIG. 58I is an image showing that Gastrocnemius (Tennis Leg) may be treated using the full-leg compression of FIG. 58;

FIG. 58J shows the flat pattern of the full-leg compression of FIG. 58 overlaid on a left leg of a wearer's body and also the flat pattern of the full-leg compression of FIG. 58 overlaid on a right leg of a wearer's body, illustrating the application of compression for treating Gastrocnemius (Tennis Leg) on both legs;

FIG. 59 is a flat pattern of a thigh compression garment, with openings formed to receive heat/cold packs into pockets therein to apply heat and/or cold therapy under compression;

FIG. 59A is an image showing the front high quad/hip region that may be treated using the thigh compression of FIG. 59;

FIG. 59B shows the flat pattern of the thigh compression of FIG. 59 overlaid on a right leg of a wearer's body, illustrating thermal treatment being provided to multiple different locations of the quad muscle, and the application of compression;

FIG. 59C is an image showing that the front high Adductor muscles may be treated using the thigh compression of FIG. 59;

FIG. 59D shows the flat pattern of the thigh compression of FIG. 59 overlaid on a right leg of a wearer's body and another overlaid on the left leg of the wearer, illustrating thermal treatment being provided to multiple different locations of the left and right quad muscles, and the application of compression;

FIG. 59E is an image showing that hamstring muscle belly may be treated using the thigh compression of FIG. 59;

FIG. 59F shows the flat pattern of the thigh compression of FIG. 59 on a right leg of a wearer's body and another overlaid on the left leg of the wearer, illustrating thermal treatment of the left and right hamstring muscles, and the application of compression for treating hamstring muscle belly;

FIG. 60 is a flat pattern of a calf compression sleeve, with openings formed to receive heat/cold packs into pockets therein to apply heat and/or cold therapy under compression;

FIG. 60A is an image showing that may Calf strain/Tennis Leg—Medial Gastrocnemius Strain be treated using the calf compression sleeve of FIG. 60; and FIG. 60B shows the flat pattern of the calf compression sleeve of FIG. 60 on a leg of a wearer's body, illustrating thermal treatment to different regions of the calf muscle, and the application of compression for treating Calf strain/Tennis Leg—Medial Gastrocnemius Strain.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment of the disclosed braces, an ankle brace may include: a sleeve with a first particularly positioned/shaped pocket and at least a second particularly positioned/shaped pocket. The sleeve may be formed of a primary layer being an elastic material configured to apply a first level of compression. The sleeve may be formed to fit on a leg of a wearer to cover the ankle, and to extend a first distance above the ankle on the lower leg of the wearer to a first end, and to extend a second distance away from the ankle onto at least a portion of the foot of the wearer to a second end. The first pocket formed in the sleeve may be substantially straight in the elongated direction (i.e., the substantially vertical direction while being worn and while standing up), being formed to overlie the Achilles tendon, and which may receive a corresponding thermal pack (i.e., heat pack or cold pack). The second pocket formed in the sleeve may be a curved pocket formed to encircle a portion of the ankle of the leg, to overlie at least a portion of one or more ligaments of the foot when the ankle brace is worn (e.g., to overlie the medial ligaments, or to overlie the lateral ligaments), and which pocket also receives a corresponding thermal pack. Alternatively, second and third pockets may both be formed in the sleeve to receive thermal packs that respectively overlie the medial ligaments and lateral ligaments.

The ends of the sleeve may be reinforced in any suitable manner, including by using a band of one or more layers of high compression material that encircle a portion of the lower leg of the wearer at the upper end of the sleeve, and a band of one or more layers of high compression material that encircle the foot of the wearer at the opposite end of the sleeve The sleeve may also be formed with one or more particularly shaped layers of high compression material configured to apply a second level of compression that is greater than the first level of compression, and which overlie certain portions of the foot, including over the pockets. A first portion of the particularly shaped layers of high compression material may extend from the upper end of the ankle brace to overlie the first pocket and the Achilles tendon of the leg, and to extend further to encircle the heel bone, when the ankle brace is worn. A second portion of the particularly shaped layers of high compression material may extend from the first portion to overlie the pocket at the medial ligaments of the foot, and to overlie the pocket at the lateral ligaments of the foot, and to circle around the bottom of the foot, when the ankle brace is worn.

DETAILED DESCRIPTION OF THE INVENTION

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipedia.org/wiki/Engineering_fit; and "Three General Types of Fit," available at www.mm-to.org/dclark/Reports/Encoder%20Upgrade/fittolerences%20%5BRead-Only%5D.pdf.

It is further noted that any use herein of relative terms such as "top," "bottom," "upper," "lower," "vertical," and "horizontal" are merely intended to be descriptive for the reader, and may be based on the depiction of those features within the figures for one particular position of the apparatus, and such terms are not intended to limit the orientation with which the disclosed apparatus may be utilized.

Also, the description herein for a compression garment for a "young" wearer refers to compression designs focused on treatment of specific areas of muscle tissue with strategic placement of compression intensity in combination with applications of heat/cold for a person who may be under the age of 40 years old in certain embodiments, or under the age of 25 years old in other embodiments. A description herein for a compression garment for an "older" wearer refers to compression designs focused on specific areas of joint and connective tissue and strategic placement of compression intensity in combination with applications of heat/cold for a person who may be over the age of 40 years old in certain embodiments, or over the age of 25 years old in other embodiments.

Figure 1:
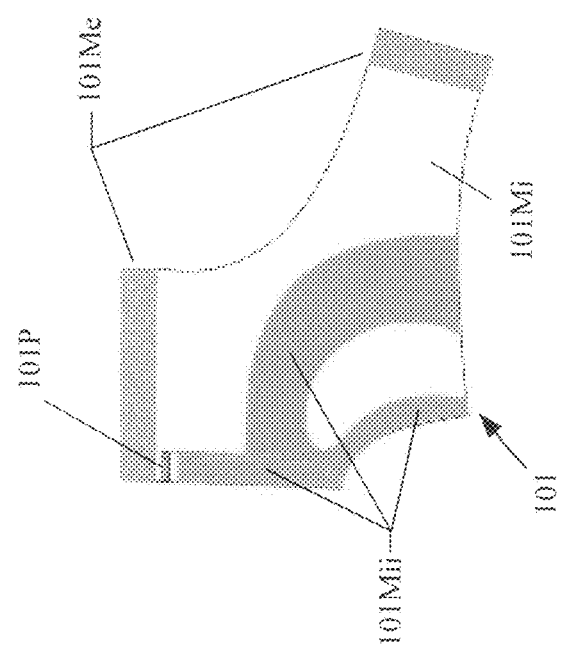
FIG. 1 is a side view of a first embodiment of a therapeutic compression garment for an ankle, with an opening formed into a pocket to receive a thermal pack (heat/cold) therein to apply heat and/or cold therapy under compression to that region of an ankle, i.e., the Achilles tendon.

FIG. 1 is an ankle compression garment 101 for applying compression and thermal treatments (heating or cooling) to a wearer's ankle that may include a primary layer of material 101Mi, which may be elastic, a liner that creates a particularly shaped pocket proximate to the Achilles tendon to receive a custom heat/cold pack through an opening 101P, and a particularly located layer or layers of higher compression material 101Mii (shown shaded in FIG. 1 and figures of the other garments) that overlie the pocket(s) and may overlie other areas as well.

Figure 2:
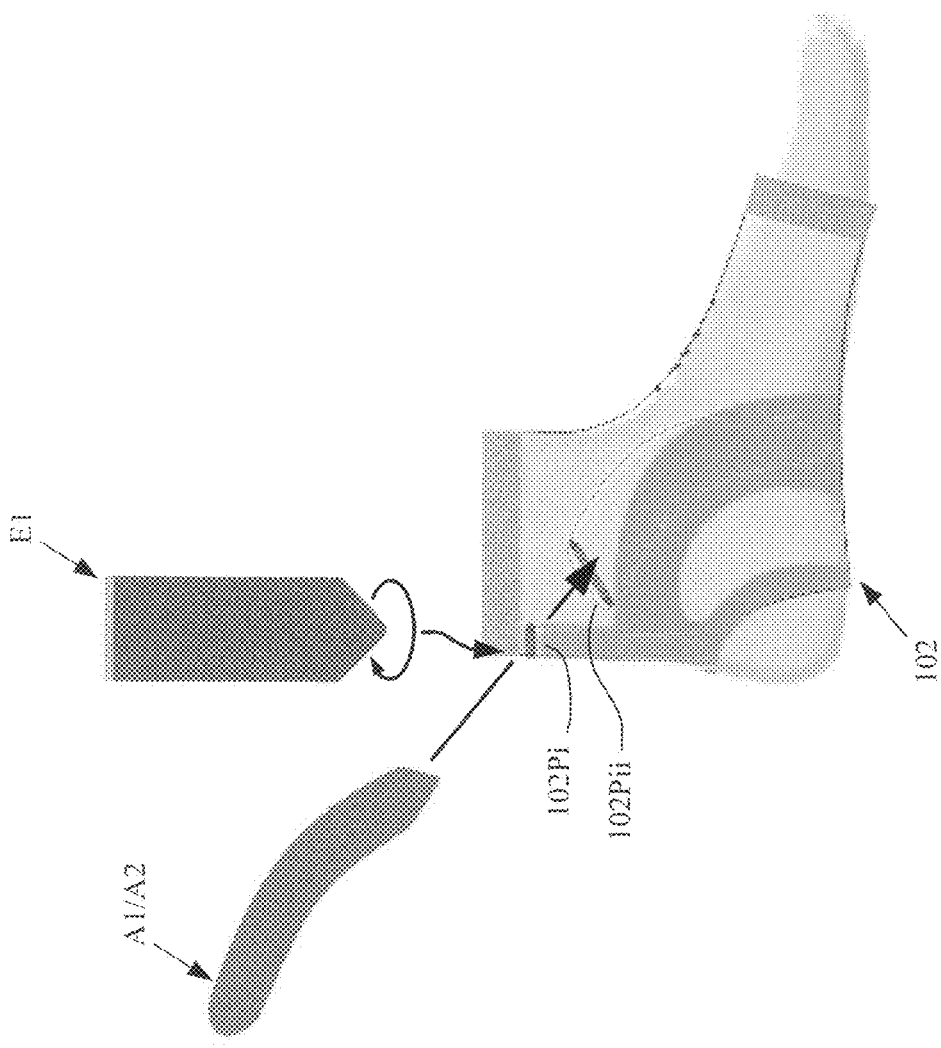
FIG. 2 is a side view of a second embodiment of a therapeutic compression garment for an ankle, shown after the therapeutic compression garment is placed on the foot of a wearer, and which includes particularly shaped heat/cold packs received in different pockets that overlie the Achilles tendon and one or both of the medical and lateral ligaments (left and/or right sides) of the foot.

The primary layer may envelop a portion of the wearer's body (i.e., the leg above and below the ankle as shown in FIG. 2), and which enveloped portion of the wearer's body includes the one or more regions to be treated thermally with the heat/cold packs. The primary layer of material 101Mi may be an elastic material that may include, but is not limited to, a spandex, a stretch vinyl, polyester, bamboo, any blends of those materials, and any other suitable fabrics known in the art. The primary layer of material 101Mi being so formed may thus be configured for an interior surface to apply a first level of compression to those enveloped portions of the wearer's body. In one embodiment the elastic of the primary layer of material 101Mi may exhibit a compression pressure in the range of 2 mm Hg to 5 mm Hg, and in another embodiment the elastic material may exhibit a compression pressure in the range of 5 mm Hg to 8 mm Hg, and in yet another embodiment the elastic material may exhibit a compression pressure in the range of 8 mm Hg to 11 mm Hg, and in another embodiment the elastic material may exhibit a compression pressure in the range of 11 mm Hg to 16 mm Hg, and in other embodiments other ranges or a combinations of those ranges may instead be used.

It is noted that to achieve the proper compression pressures, the garment must be very closely sized/fitted to the size of the corresponding features of the wearer, because a garment (e.g., an arm brace) that applies the proper compression pressure on a large person, would otherwise merely hang on a much smaller person. Therefore, the garments disclosed herein are described in terms of more than one size (e.g., a small size and a large size, with correspondingly sized heat packs), with the understanding that there may be a substantial plurality of different sized garments to accommodate various sized people to achieve those proper compression pressures.

The areas to be treated using the higher compression material 101Mii may use one or more layers of a second material. In one embodiment, only one layer of the material may be used at a thermal treatment region, and in another embodiment two layers of the material may be used at a treatment region, and in yet another embodiment three layers of the material may be used at a treatment region, while other numbers of layers may be used in other embodiments.

The one or more layers of the second material may be a higher compression material that may include, but is not limited to: a thermoplastic elastomer (TPE) material, a polyurethane, and any other suitable material known in the art.

Where three layers of the compression material are used, an innermost compression layer may be the closest of those layers to the skin of the wearer, an outermost layer may be the farthest away from the skin of the three layers, and the middle layer may be positioned between the other two layers. One or more of those layers may be a mesh, and where three layers are used, the middle layer may preferably be a mesh.

Figure 12B:
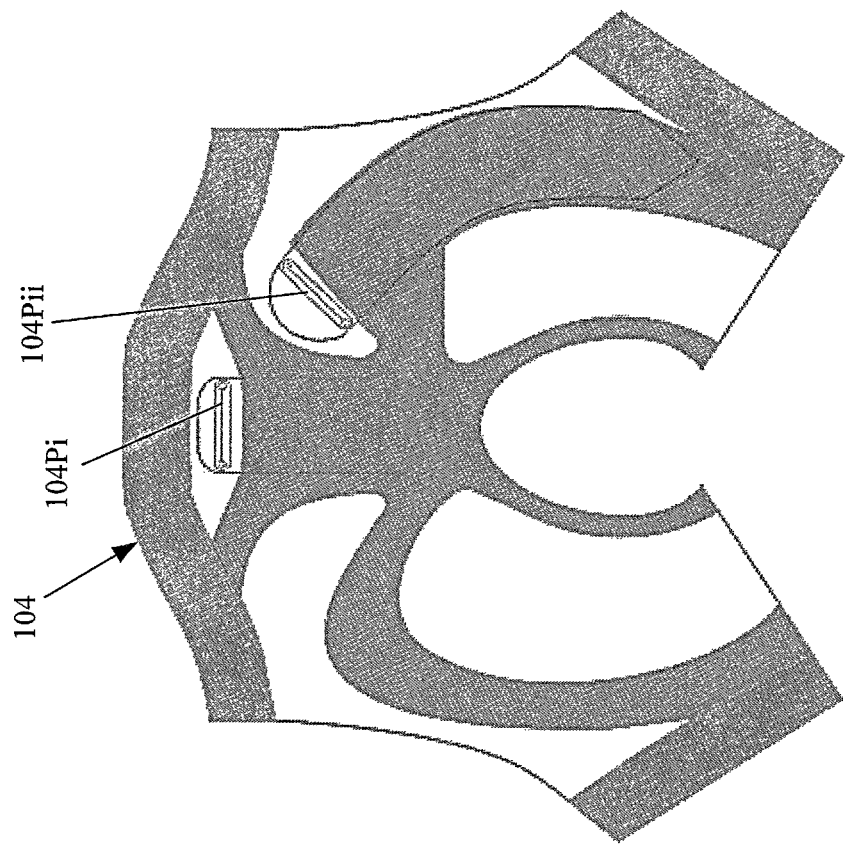
FIGS. 12A-12B are flat patterns for another embodiment of an ankle compression, having heat/cold packs therein that are respectively sized for different sized wearers.

The layer or the layers of the higher compression material 101Mii at each treatment region, which layers may be stacked, may in one embodiment replace the primary layer of material 101Mi (see e.g., FIG. 12E), or may in another embodiment be fixedly secured to the primary layer of material 101Mi on its interior surface (see e.g., FIG. 12D) in any suitable manner (e.g., by stitching), and each may be shaped to overlay and extend beyond the treatment region of the wearer's body. The second material of the one or more layers may be a compression material configured to apply a second level of compression being greater than the first level of compression applied by the elastic material of the primary layer of material 101Mi. In one embodiment this higher compression material may be formed to exhibit a compression pressure in the range of 20 mm Hg to 35 mm Hg, and in another embodiment the high compression material may exhibit a compression pressure in the range of 35 mm Hg to 50 mm Hg, and in yet another embodiment the high compression material may exhibit a compression pressure in the range of 50 mm Hg to 65 mm Hg, and in another embodiment the high compression material may exhibit a compression pressure in the range of 65 mm Hg to 88 mm Hg, and in other embodiments other ranges or a combinations of those ranges may instead be used.

Each of the ends of the ankle compression garment 101 may include a reinforcement region 101Me that may reinforce the ends against overstretching and deterioration from repeated use. The reinforcement region 101Me may just be the elastic material of the primary layer of material 101Mi being doubled over upon itself and stitched together, or the reinforcement region 101Me may be a higher compression material and/or any other suitable material that may be added thereto to accomplish such reinforcement. The use of such reinforced ends may be utilized on any of the compression garments disclosed herein.

FIGS. 5-10A show different sized and shaped custom heat/cold packs (B1, B2, C1, C2, D1, D2, E1, and E2) that may be used in the compression garments disclosed herein, each of which may be generally shaped like a gonfalon flag, having a square or an elongated rectangular body that transitions into a triangular shape with a tip of the triangular shape that may be centrally positioned, and which tip may be pointed or may be slightly rounded. FIGS. 3-4A and 11-11A show similarly shaped custom heat/cold packs (A1, A2, F1, and F2), which also have a triangular-shaped tip, but rather than being straight they are curved to accommodate placement in proximity to a curved feature of the person's anatomy (e.g., proximate to the ankle, the patella, etc.). It is noted that each shape may be configured and used as either a cold pack or a heat pack to apply either thermal treatment type. The tip of the gonfalon shaped heat/cold packs may first be inserted into a pocket designed to receive it, to establish some clearance between the liner and the high compression layers, prior to the entirety of the width of its heat/cold pack body being slowly inserted through the opening. The tip of the gonfalon shape of the heat/cold packs may ultimately be positioned at a bottom of the pocket, which pocket may be correspondingly shaped. Each of the corners of the heat/cold packs may also be rounded. Each compression garment disclosed herein is designed to provide therapy and/or relief by using anatomically specific compression levels in combination with targeted heat/cold therapy, such that the heat/cold therapy is applied directly to the treatment area using pockets in the compression garment that are configured to completely enclose the particularly designed/shaped heat/cold packs, despite the opening into the pocket (i.e., the compression material seals off the opening after the heat/cold pack has been inserted).

Heat and cold packs are generally known in the art, as shown for example by the following U.S. Pat. No. 2,907,173 to Robbins; U.S. Pat. No. 3,175,558 to Caillouette; U.S. Pat. No. 3,342,324 to Piazze; U.S. Pat. No. 3,542,032 to Spencer; U.S. Pat. No. 3,804,077 to Williams; U.S. Pat. No. 4,462,224 to Dunshee; U.S. Pat. No. 5,792,213 to Bowen; U.S. Pat. No. 3,889,684 to Lebold; U.S. Pat. No. 4,462,224 to Dunshee; U.S. Pat. No. 4,700,706 to Munch; U.S. Pat. No. 5,190,033 to Johnson; and U.S. Pat. No. 5,843,145 to Brink.

In one embodiment the heat/cold packs A1, A2, B1, B2, C1, C2, D1, D2, E1, E2, F1, and F2 may have the dimensions and general characteristics respectively shown in FIGS. 3-11A, which are summarized below:

| A1 | A2 | D1 | D2 | F1 | F2 |
|---|---|---|---|---|---|
| 38 mm-W | 38 mm-W | 38 mm-W | 38 mm-W | 32 mm-W | 32 mm-W |
| 150 mm-H | 180 mm-H | 200 mm-H | 240 mm-H | 80 mm-H | 100 mm-H |
| 9 mm-D | 10 mm-D | 9 mm-D | 12 mm-D | 9 mm-D | 9.5 mm-D |
| 75 mm-90 mm R | 108 mm-121 mm R | | | 46 mm-61 mm R | 46 mm-61 mm R |
| (3.0"-3.5" R) | (4.25"-4.75" R) | | | (1.8"-2.4" R) | (1.8"-2.4" R) |
| (curvature) | (curvature) | | | (curvature) | (curvature) |
| 26 grams | 32 grams | 28 grams | 34 grams | 12 grams | |
| C1 | C2 | B1 | B2 | E1 | E2 |
| 40 mm-W | 50 mm-W | 90 mm-W | 100 mm-W | 38 mm-W | 50 mm-W |
| 70 mm-H | 80 mm-H | 100 mm-H | 120 mm-H | 100 mm-H | 110 mm-H |
| 9 mm-D | 10 mm-D | 11.5 mm-D | 15 mm-D | 11 mm-D | 11 mm-D |
| 6 grams | 20 grams | 66 grams | 106 grams | 12 grams | 11 grams |

Figure 3:
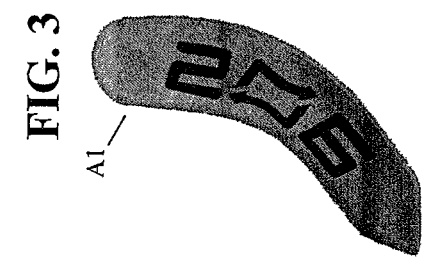
FIG. 3 is a front view of a first curved heat/cold pack shape, usable with different compression garments disclosed herein.
Figure 3A:
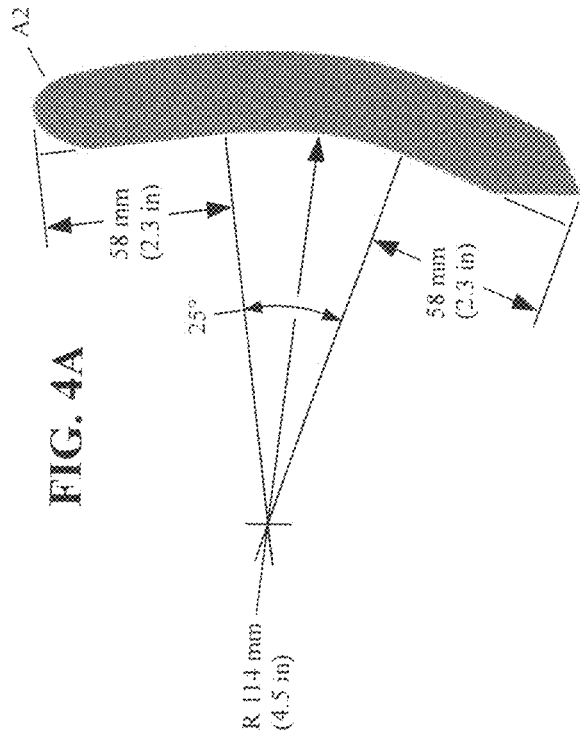
FIG. 3A is the front view of the curved heat/cold pack of FIG. 3 shown enlarged and dimensioned.
Figure 4A:
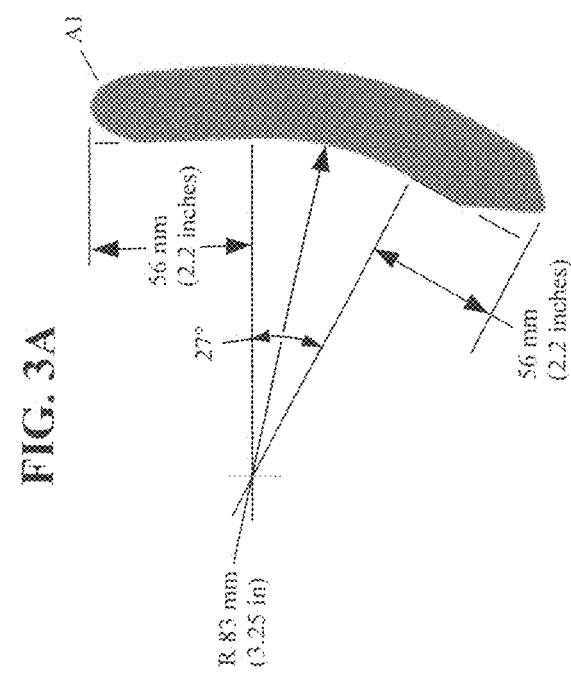
FIG. 4A is the front view of the curved heat/cold pack of FIG. 4 shown enlarged and dimensioned.
Figure 11B:
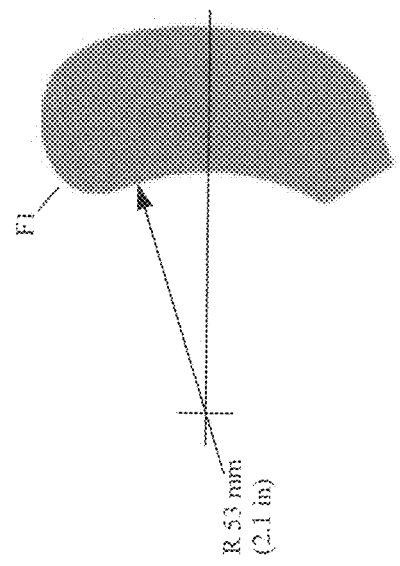
FIG. 11B is the front view of the curved heat/cold pack of FIG. 11 shown enlarged and dimensioned.

(Note that the radius of curvature for the curved heat/cold packs A1, A2, and F1 and F2 identifies the inner radius of its curved portion; the outer radius of curvature only requires adding of the width thereto). As seen in FIGS. 3A and 4A, the A1 and A2 heat/cold packs may have a radiused portion, from which two straight portions may respectively extend tangentially from its ends, although those thermal packs are referred to hereinafter more simply as "curved" heat/cold packs.

FIG. 2 is an ankle compression garment 102 formed substantially the same as ankle compression garment 101 in FIG. 1, except that it may also have, in addition to an opening 102Pi into a pocket proximate to the Achilles tendon that warps around that tendon, a second opening 102Pii that receives a cold pack on one side of the foot in proximity to either the lateral ligaments or the medial ligaments. Alternatively, there may be a pocket formed on each of side of the brace that receive a respective curved heat/cold pack therein for thermal treatment of both the medial and the lateral ligaments. In FIG. 2, the ankle compression garment 102 is shown after being placed on the foot of a wearer, but prior to insertion of the particularly shaped heat/cold packs (e.g., A1/A2) that are designed for the two pocket types. (Note the A1 heat/cold pack may accommodate a range of smaller wearers, while the larger A2 heat/cold pack and corresponding pocket(s) may accommodate a range of larger wearers; however, other intermediate sizes or larger/smaller sized packs and pockets may also be used for a better fit). The layer or layers of high compression material of each garment (e.g., garment 101/102 are configured to completely enclose the particularly designed/shaped thermal pack after being positioned fully into the pocket. The ankle compressions 101 and 102 may have high compression material located as illustrated in FIG. 2, i.e., encircling a portion of the lower leg of the wearer at the upper end; encircling a portion of the foot of the wearer at the opposite end; a first portion extending from the upper end to overlie the Achilles tendon and extend further to encircle the heel bone; and a second portion extending from the first portion to overlie the lateral and medial ligaments of the leg and to encircle the bottom of the foot.

The thermal treatments provided by these ankle brace embodiments may serve to reduce swelling and treat tendons and sprained ligament, and may also treat retrocalcaneal bursitis, bunions, flat feet, and high arch feet. The ankle compressions 101 and 102 may also serve to stabilize the heel and ankle, and reduce the chances of spraining a healthy ankle.

Figure 2B:
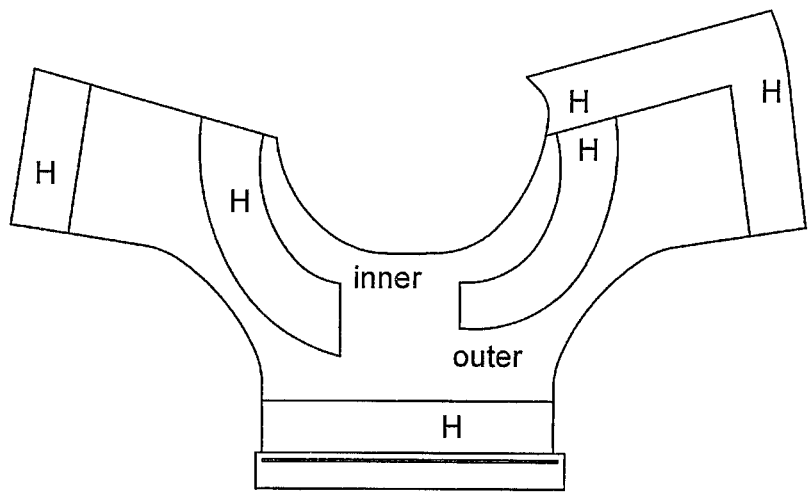
FIG. 2B is a view of a flat pattern that may be used to make the compression garment of FIG. 2.
Figure 2A:
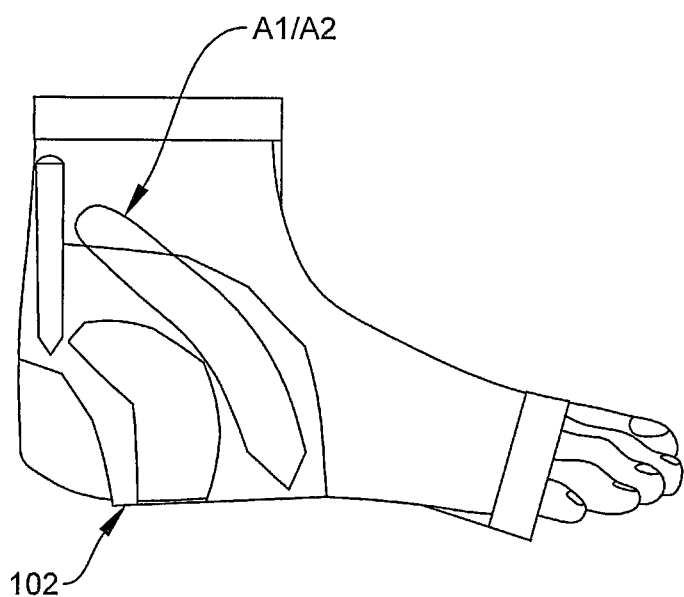
FIG. 2A is the side view of FIG. 2, shown after insertion of one of the particularly shaped heat/cold packs into the different pockets.
Figure 11:
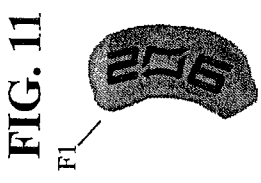
FIG. 11 is a front view of a third curved heat/cold pack shape, being smaller than the first and second curved heat/cold packs of FIG. 3 and FIG. 4.
Figure 9:
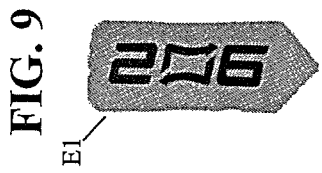
FIG. 9 is a front view of a third rectangular gonfalon-shaped heat/cold pack, being longer and narrower than the heat/cold pack of FIG. 8.
Figure 10:
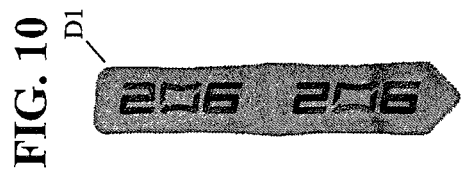
FIG. 10 is a front view of a fifth rectangular gonfalon-shaped heat/cold pack, being longer and narrower than the heat/cold pack of FIG. 9.
Figure 7:
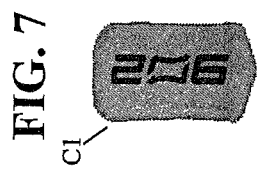
FIG. 7 is a front view of a first rectangular gonfalon-shaped heat/cold pack, usable with different compression garments disclosed herein.
Figure 5:
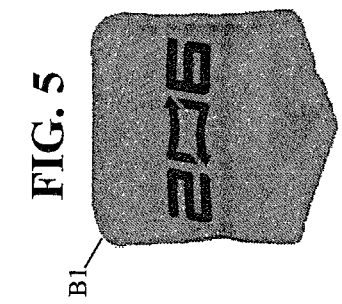
FIG. 5 is a front view of a first square gonfalon-shaped heat/cold pack, usable with different compression garments disclosed herein.
Figure 11A:
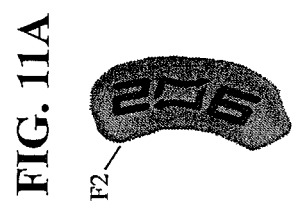
FIG. 11A is a front view of a fourth curved heat/cold pack shape, being smaller than the first and second curved heat/cold packs of FIG. 3 and FIG. 4, and larger than the heat/cold pack of FIG. 11.
Figure 9A:
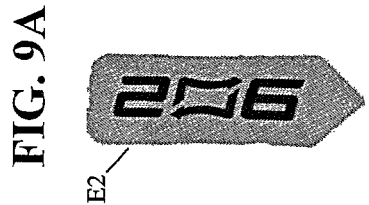
FIG. 9A is a front view of a fourth rectangular gonfalon-shaped heat/cold pack, being longer than the heat/cold packs of FIG. 8 and FIG. 9.
Figure 10A:
FIG. 10A is a front view of a sixth rectangular gonfalon-shaped heat/cold pack, being longer and narrower than the heat/cold pack of FIG. 10.
Figure 8:
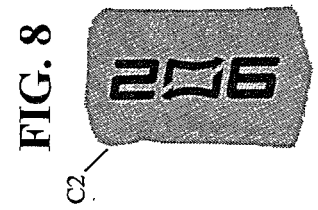
FIG. 8 is a front view of a second rectangular gonfalon-shaped heat/cold pack, being larger than the heat/cold pack of FIG. 7.
Figure 6:
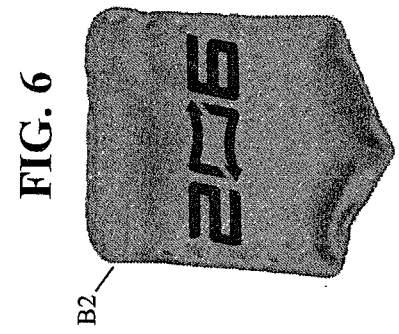
FIG. 6 is a front view of a second square gonfalon-shaped heat/cold pack, being larger than the heat/cold pack of FIG. 5.
Figure 4:
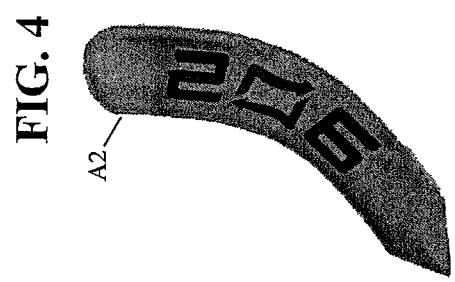
FIG. 4 is a front view of a second curved heat/cold pack shape, being larger than the first curved heat/cold pack of FIG. 3.
Figure 12A:
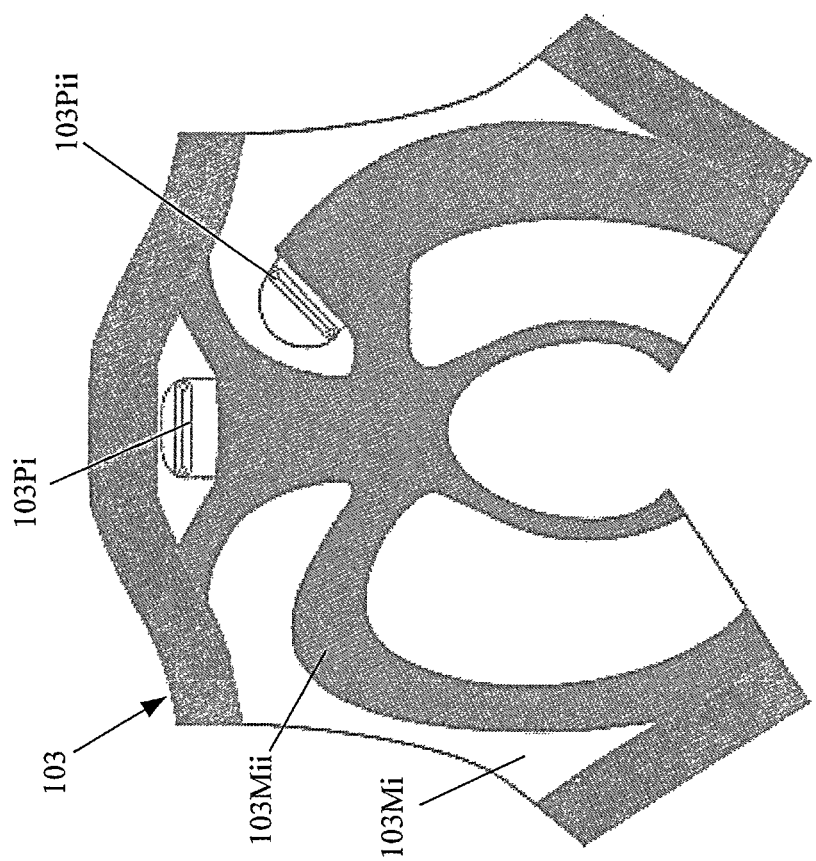

FIG. 12A is a flat pattern for an ankle compression garment 103 that may be formed similar to the ankle compression 102, but may accommodate receiving the heat/cold packs in the respective pocket to be entirely beneath the high compression materials 103Mii and not beneath the elastic material 103Mi. (Note that in other embodiments, the heat/cold pack used may be longer such that a portion of the pack being nearest the openings 103Pi/103Pii may extend beyond the high compression material and even beyond the opening, which may make it easier for the wearer to remove it and insert a fresh heat/cold pack—See FIG. 2A).

The flat pattern of the ankle compression garment 103 in FIG. 12A may be proportionally formed to accommodate smaller wearers (e.g., an extra-small, a small, and a medium size foot) and may receive one C1 heat/cold pack into the pocket through opening 103Pi and one A1 heat pack into the pocket (or pockets where formed on both sides of the foot) through opening 103Pii. The flat pattern of the ankle compression garment 104 in FIG. 12B is proportionally formed to accommodate larger wearers (e.g., a large, extra-large, and a double extra-large size foot) and may receive one E1 heat/cold pack into a pocket through opening 104Pi and one or two A2 heat packs into a pocket through opening(s) 104Pii.

In one embodiment the opening at each treatment region may be positioned so as to also be formed in the one or more layers of the high compression material (see FIG. 18), and in another embodiment the opening may be formed just beyond the end of the one or more layers of the high compression material (see FIGS. 12A/12B), and with the opening being sized to admit the width of either a heat pack or a cold pack therethrough, which heat packs and cold packs may be the same or similarly sized.

Figure 12C:
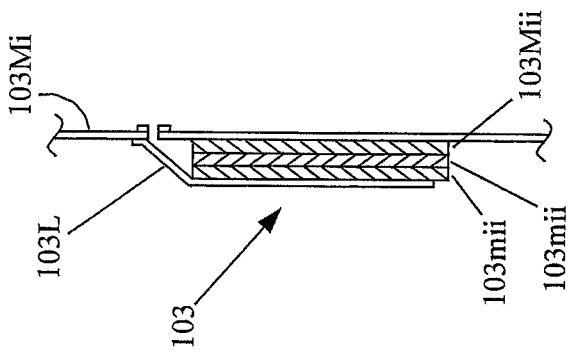
FIG. 12C is a cross-sectional view through the pockets of the ankle compression of FIG. 12A that is configured to be located proximate to the wearer's Achilles heel, shown prior to inserting of a heat/cold pack therein.
Figure 12D:
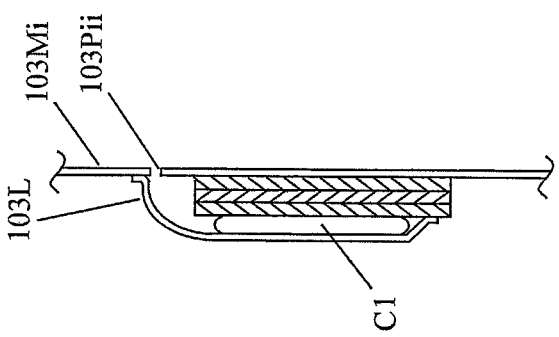
FIG. 12D is the cross-sectional view of FIG. 12C, shown after inserting of a heat/cold pack into the pocket.
Figure 12E:
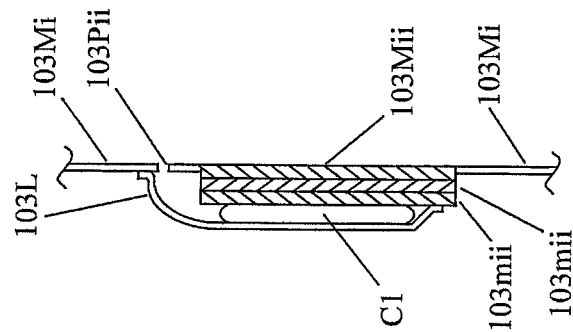
FIG. 12E is the cross-sectional view of FIG. 12D, but is shown for the embodiment where the high compression materials are joined substantially end to end or slightly overlapped with the elastic material, rather than having its entire periphery secured thereto.

FIG. 12C shows a section cut through one embodiment that may be used for forming, in general, the pocket(s) of the compression garments disclosed herein, showing the use of three layers of high compression material 103Mii and a liner 103L to form a pocket beneath the high compression materials. FIG. 12D shows the cross-sectional view of FIG. 12C after insertion of a C1 heat/cold pack into the pocket. The liner 103L may be fixedly secured to the arrangement to create a selectively shaped pocket. A first (upper) portion of a periphery of the liner 103L may be fixedly secured to the interior surface of the elastic material 103Mi such that it may extend over the opening 103Pii, and a second portion of a periphery of the liner may extend over only a portion of a periphery of the one or more layers of the high compression material, and be secured to the one or more layers to form the pocket (i.e., so that the layers of high compression material overlie the bottom and sides of the pocket). The interior of the pocket may thereby be selectively shaped to receive the correspondingly shaped heat/cold pack therein. In one embodiment, the upper portion of the liner 103L may be coterminous with the extent of the left and right sides and the opening 103Pii, and the liner may be secured (e.g., stitched) thereto. In another embodiment, the upper portion of the liner 103L may be slightly wider than the extent of the left and right sides of the opening 103Pii, and may also extend above the top of the opening 103Pii, and may be secured thereat.

Positioning the opening 103Pii only in the elastic material 103Mi and not in the high compression material layer(s) 103Mii makes it easier to initiate installing of the heat/cold packs into the pocket from the outside of the garment while it is being worn. In addition, to further accommodate ease of installing of the heat/cold packs 80H/80C into the pocket, in one embodiment the liner 103L may be made of the same elastic material used for the elastic material 103Mi of the primary layer. Since the liner 103L should preferably be very conducive to transmitting heat/cold therethrough, in another embodiment the liner 103L is preferably made of a thinner elastic material than the elastic material 103Mi, and may be only a slightly elastic material (e.g., it may exhibit a compression pressure in the range of 1 mm Hg to 5 mm Hg). In another embodiment the liner 103L may be made of a light to medium weight cotton fabric that may be slightly oversized for holding the heat/cold packs, or instead of being oversized, cotton blends thereof may be used that may include blends with elastic fibers.

To permit further ease of installing the heat/cold packs into the opening 103Pii and beneath the high compression layer(s) 103Mii, the heat/cold packs may have the pointed gonfalon flag shape described hereinabove. With the custom sized/shaped heat/cold packs being positioned beneath the high compression layer or layers, the compressive force of those layers force the heat/cold packs into contact with the wearer's skin surface above the region to be treated, making them more effective, permitting the use of smaller (e.g., thinner) heat/cold packs.

FIG. 13 is a flat pattern for an ankle compression garment 105 that may be similarly formed, and which may include a "sticky" (i.e., a stay-in-place) material 105S on the inside around the circumference of the reinforced ends of the sleeve, both at the end above the ankle and the end near the toes (see FIG. 13A). The stay-in-place material at each end of the sleeve may ensure that the compression stays in the proper position while being worn. The ends of the compression sleeve may be rolled up to position the stay-in-place material away from the body for ease in putting the compression on the affected body region and for preventing overstretching of the circumference of the brace during application and removal, and the ends may be rolled down after being properly positioned on the body region to position the stay-in-place material against the wearer's skin. The "sticky" material may be any suitable material, including, but not limited to, a rubber material. The stay-in-place material may have any suitable width and in one embodiment may be formed of a plurality of narrow bands, and in another embodiment may be formed of a single band that may have a width between 0.02 inches and 0.05 inches, and in another embodiment may have a width between 0.05 inches and 0.12 inches, and in yet another embodiment may have a width between 0.12 inches and 1.0 inches, and in other embodiments, any combination of those ranges or other suitable ranges for the width may be used instead. The stay-in-place material may be used at the ends of any of the compression garments disclosed herein. It is noted that a gap may be provided between the reinforced ends of any of the sleeves disclosed herein and the higher compression materials used therein, to make folding over of the reinforced ends easier.

Figure 14A:
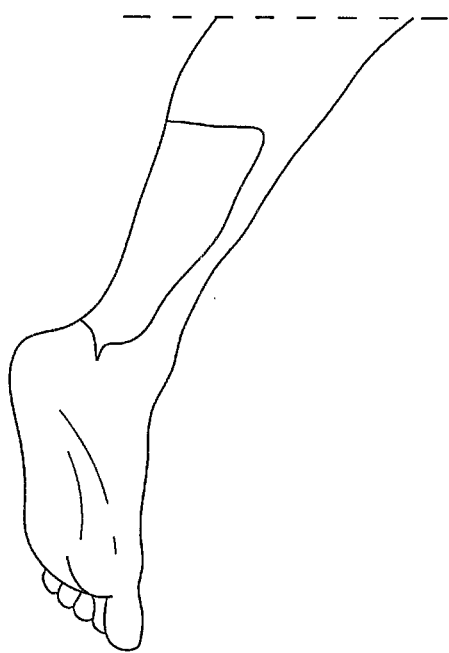
FIG. 14A is an image showing the region of the foot that may be affected by an Achilles sprain or pain.
Figure 14B:
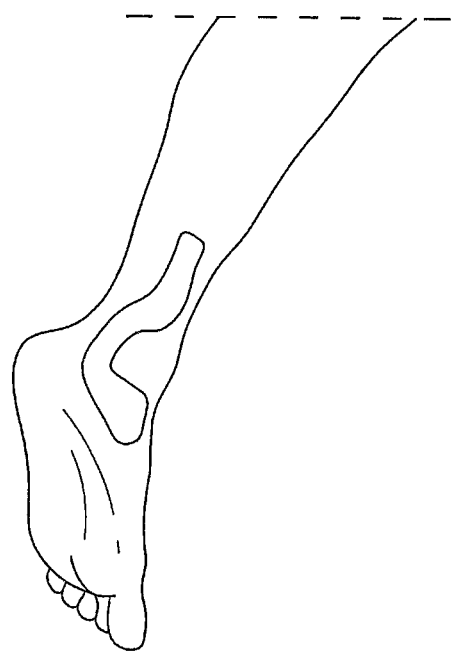
FIG. 14B is an image showing the region of the foot that may be affected by retrocalcaneal bursitis.
Figure 14C:
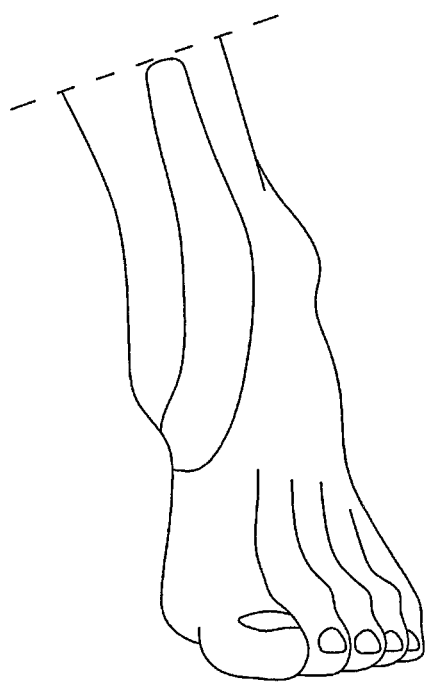
FIG. 14C is an image showing the region of the foot that may be affected by an injury to the anterior tibial tendon.
Figure 14D:
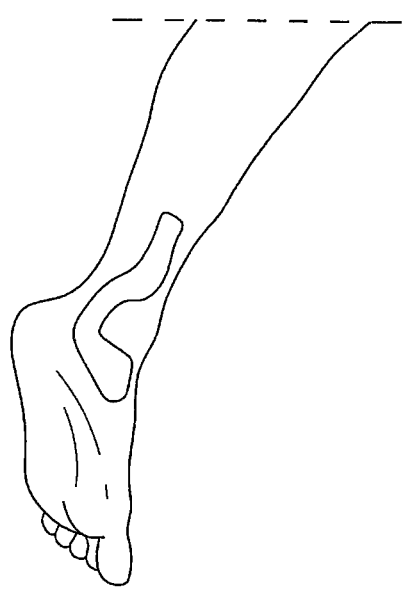
FIG. 14D is an image showing the region of the foot that may be affected by an injury to posterior tibial tendon.
Figure 14F:
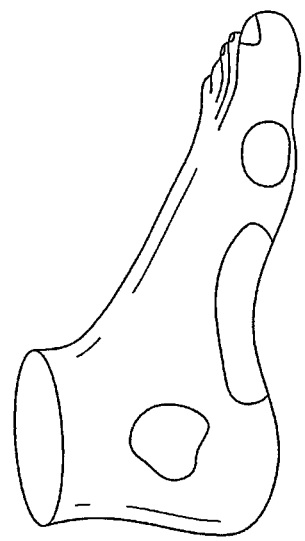
FIG. 14F is an image showing the region of the foot that may be affected by bunions, flat feet, and/or high arch feet.
Figure 14E:
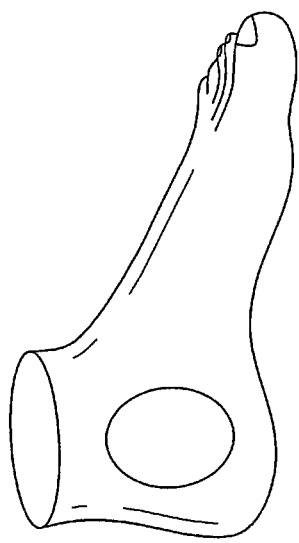
FIG. 14E is an image showing the region of the foot that may be affected by a ligament sprain.

The target user for each of the ankle compression garments 101/102/103/104/105 may be anyone at any age that may be suffering a sprain, strain or other injury to the tendons or ligaments of the foot and ankle areas, or anyone suffering from chronic issues from flat feet, high arches, bunions or Achilles heel pain. The use of heat or "ice" (i.e., a heat pack or a cold pack) may be injury and/or location specific as follows (see FIGS. 14A, 14B, 14C, 14D, 14E, and 14F):

FIG. 14A—Achilles Sprain or Pain: The anterior tibial tendon lies on the inner-front of the ankle. The muscle and tendon work together to flex the foot upwards. This condition occurs when the tendon is inflamed from overuse or traumatic ankle injury:
  Use Compression to reduce pain and swelling;
  Use ICE ONLY on the back of the ankle as needed to control pain and swelling;
  Optional: Use ICE on the side inserts of the compression to help control pain or swelling.
FIG. 14B—Retrocalcaneal Bursitis (ICE only) is inflammation of the bursa (a small, cushioning sac located where tendons pass over areas of bone around the joints), which lies over your heel (calcaneum) where your Achilles tendon inserts; Compression in combination with ICE can relieve symptoms.
  Use Compression to reduce pain and swelling;
  Use ICE ONLY on the back of the ankle as needed to control pain and swelling;
  Optional: Use ICE on the side inserts of the compression to help control pain or swelling.
FIG. 14C—Anterior Tibial Tendon. (HEAT or ICE) The anterior tibial tendon lies on the inner-front of the ankle. The muscle and tendon work together to flex the foot upwards. This condition occurs when the tendon is inflamed from overuse or traumatic ankle injury;
  Use Compression to reduce pain and swelling;
  Use HEAT or ICE as needed to control pain and swelling.
FIG. 14D—Posterior Tibial Tendons—The tibialis posterior muscle originates on the inner posterior borders of the tibia and fibula. As well as being a key muscle and tendon for stabilization, the tibialis posterior also contracts to produce inversions and assists in the plantar flexion of the front at the ankle. The tibialis posterior has a major role in supporting the medial arch of the foot;
  Use Compression to reduce pain and swelling;
  Use HEAT or ICE as needed to control pain and swelling.
FIG. 14E—Ligament+Sprain—The anterior tibial tendon lies on the inner-front of the ankle. The muscle and tendon work together to flex the foot upwards.
  This condition occurs when the tendon is inflamed from overuse or traumatic ankle injury;
  Use Compression to reduce pain and swelling;
  Use HEAT or ICE as needed to control pain and swelling.
FIG. 14F—Bunions * Flat Feet * High arch feet—
  Compressions with heat or ice can alleviate the symptoms of bunions, flat feet or high arches.
  Use Compression to reduce pain and swelling;
  Use HEAT or ICE as needed to control pain.
Medial/Lateral Ligaments (ICE); and
Achilles tendon (Heat or ICE).
FIG. 15A shows a flat pattern for an arm compression sleeve 201 for applying compression and thermal treatments (heating or cooling) to a wearer's wrist that may include a primary layer of material 201Mi, which may be elastic, a liner that creates particularly positioned and shaped pockets that receive a custom heat/cold pack through openings 201Pi and 201Pii, and a particularly located layer or layers of higher compression material 201Mii that forms a band that overlies the pocket(s), in a central region of the brace, and in other regions forms bands at the two opposite ends of the sleeve (e.g., for reinforcement). As noted above, each pocket of the compression garment 201 is designed to completely enclose the particularly designed (i.e., sized/shaped) thermal pack after having been fully inserted into the pocket, through the opening (i.e., the layers of high compression material will seal the opening after the heat pack has been fully inserted). An opening 201T may be provided to receive the wearer's thumb therethrough. The opening 201Pi may be into a pocket located proximate to the anterior side of the wrist, as seen in FIG. 15A, such that the associated and particularly sized heat/cold pack received therein may overlie and extend slightly beyond the tendons of the third, (fourth,) and fifth compartments (see FIG. 15Ci). The opening 201Pii is into the pocket shown located proximate to the base of the thumb to apply heat/cold thereat for the associated and particularly sized heat/cold pack to overlie and extend slightly beyond the tendons of the first and second dorsal compartments—see FIG. 15Ci, which makes the arm compression sleeve 201 specific for the left and right sides. The compression sleeve 201 may be used to treat Carpal Tunnel Syndrome and may use cold packs to do so, and may also use a compression material at the lower end of the above noted pressure range (e.g., exhibiting a compression pressure closer to 20 mm Hg), to reduce pressure on the median nerve. The compression sleeve 201 may be used to treat De Quervain's Tenosynovitis and may use cold packs to do so, and may reduce rubbing of tendons in the first dorsal compartment (see FIG. 15Ci) and reduce the likelihood of tenosynovitis (especially for someone who is left handed). The compression sleeve 201 may also be used to treat arthritis (e.g., in the first CMC joint using heat), and may improve the mobility of joints. The compression sleeve 201 may be used to reduce inflammation of tendons using cold treatments. The compression sleeve 201 may be used to prevent "bow stringing" of tendons and reduce the force of contraction on wrist flexor tendons. The compression sleeve 201 may also be used to reduce the chances of tearing the triangular fibrocartilage complex (TFCC) in the wrist.

FIG. 15B shows a flat pattern for a compression sleeve 202 for applying compression and thermal treatments (heating or cooling) to a wearer's wrist that may be formed the same as arm compression sleeve 201, but may have an opening 202Pi into one pocket formed to receive an E1 heat/cold pack, the tip of which may extend slightly beyond the wrist to reach the palm, and may also extend beyond the high compression materials. The arm compression sleeve 202 may also have an opening 202Pii into another pocket formed to receive a C1 heat/cold pack. As noted above, each pocket of the compression garment 202 is designed to completely enclose the particularly designed (i.e., sized/shaped) thermal pack after having been fully inserted into the pocket, through the opening (i.e., the layers of high compression material will seal the opening after the heat pack has been fully inserted).

The application of high compression by compression sleeve 202 may prevent "bowstringing" of tendons and reduce the force of contraction on wrist flexor tendons. The fingers and wrist were made to flex, but not at the same time. Although the long flexor tendons possess a natural tendency to bow string, and even though the flexor retinaculum (Transverse Carpal Ligament—TCL) functions to prevent bowstringing, the mechanism becomes overused with constant finger flexion accompanied by wrist flexion. This combination feels unnatural and typically only occurs when specific job tasks require the combination to hold or assemble an object. The pressure exerted on the tendons as they glide and rub across the distal edge of the TCL results in inflammation leading to swelling. The ensuing pressure in the carpal tunnel (see FIG. 15D) entraps the median nerve yielding carpal tunnel syndrome. Additionally there is direct pressure on the median nerve as it is sandwiched between the flexor tendons and the TCL.

Figure 15E:
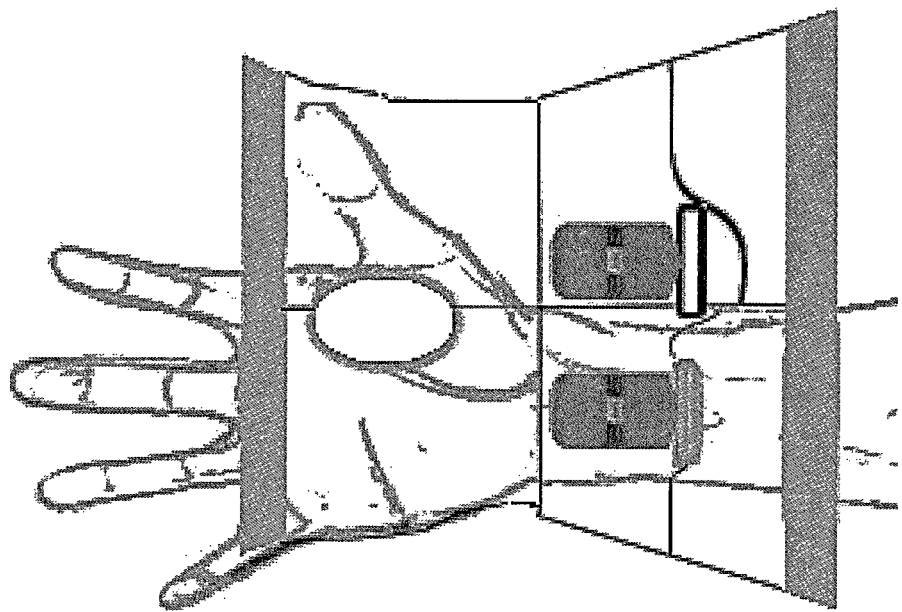
FIG. 15E shows the flat pattern of the therapeutic wrist and hand compression of FIG. 15B overlaid onto an arm to illustrate treatment provided for carpal tunnel syndrome.
Figure 15D:
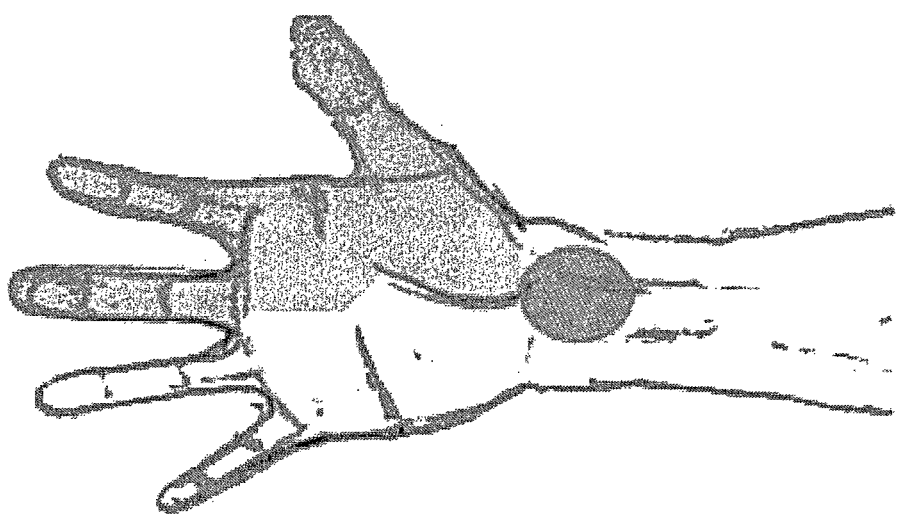
FIG. 15D is an image showing the region of the wrist and hand that may be affected by carpal tunnel syndrome.

The application of compression by compression sleeve 202 over the first dorsal compartment tendons (which includes the tendons of the abductor pollicis longus (APL) and the extensor pollicis brevis (EPB)—see FIG. 15Ci) and the use of cold packs helps to reduce the chances of becoming afflicted with tenosynovitis (especially for someone who is left-handed). Tenosynovitis is the inflammation of the fluid-filled sheath (called the synovium) that surrounds a tendon (see FIG. 15E), typically leading to joint pain, swelling, and stiffness. Tenosynovitis can be either infectious or noninfectious.

Figure 15G:
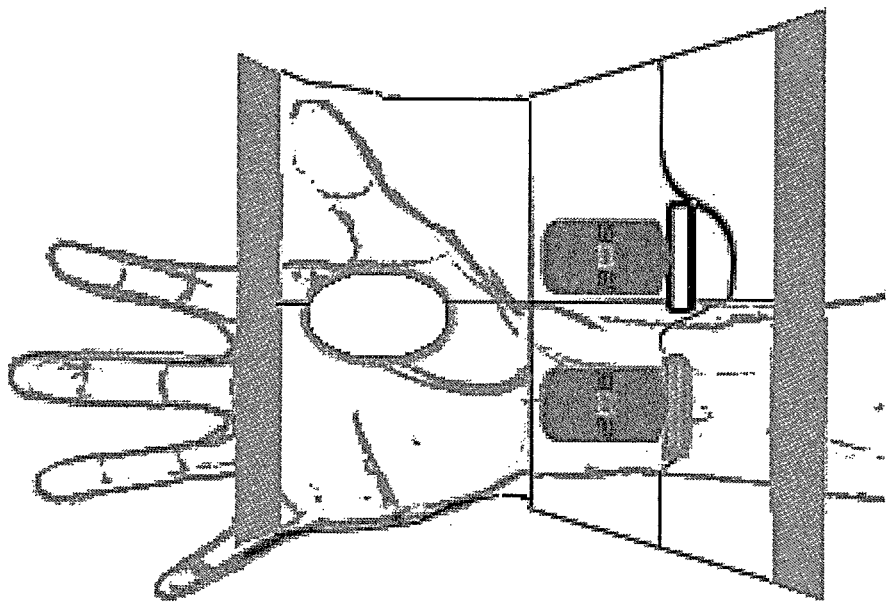
FIG. 15G shows the flat pattern of the therapeutic wrist and hand compression of FIG. 15B overlaid onto an arm to illustrate treatment provided for tenosynovitis of the first dorsal compartment tendons.
Figure 15F:
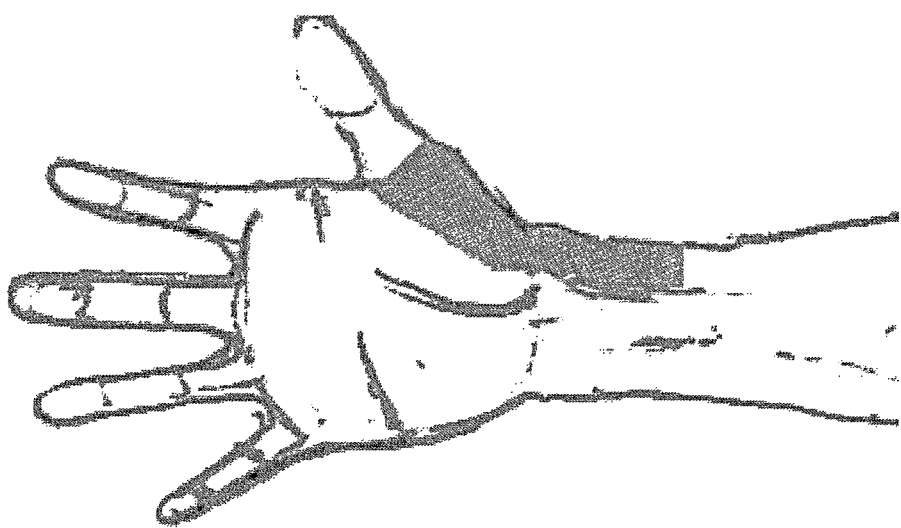
FIG. 15F is an image showing the region of the wrist and hand that may be affected by tenosynovitis of the first dorsal compartment tendons.
Figure 15I:
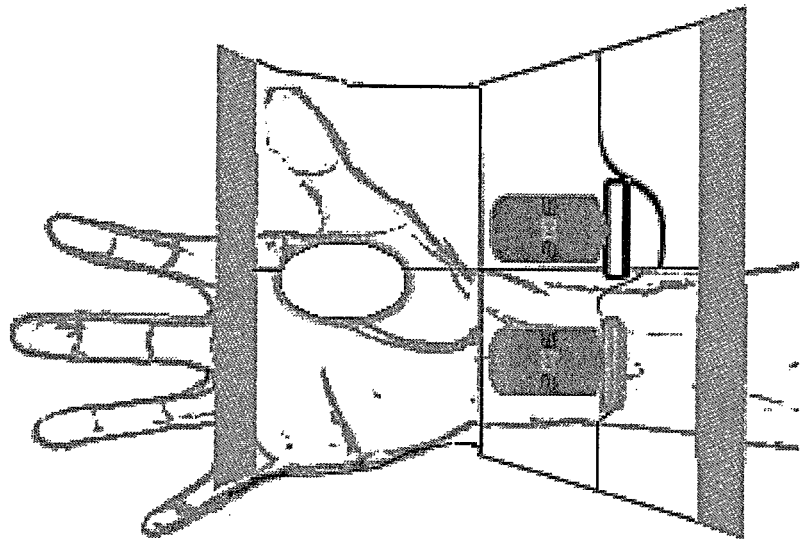
FIG. 15I shows the flat pattern of the therapeutic wrist and hand compression of FIG. 15B overlaid onto an arm to illustrate treatment provided for arthritis of the thumb carpometacarpal (CMC) joint.
Figure 15H:
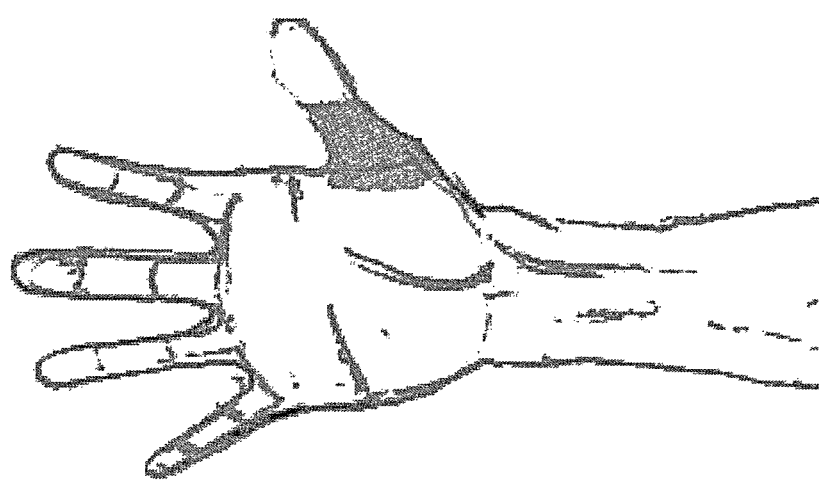
FIG. 15H is an image showing the region of the wrist and hand that may be affected by arthritis of the thumb carpometacarpal (CMC) joint.
Figure 15K:
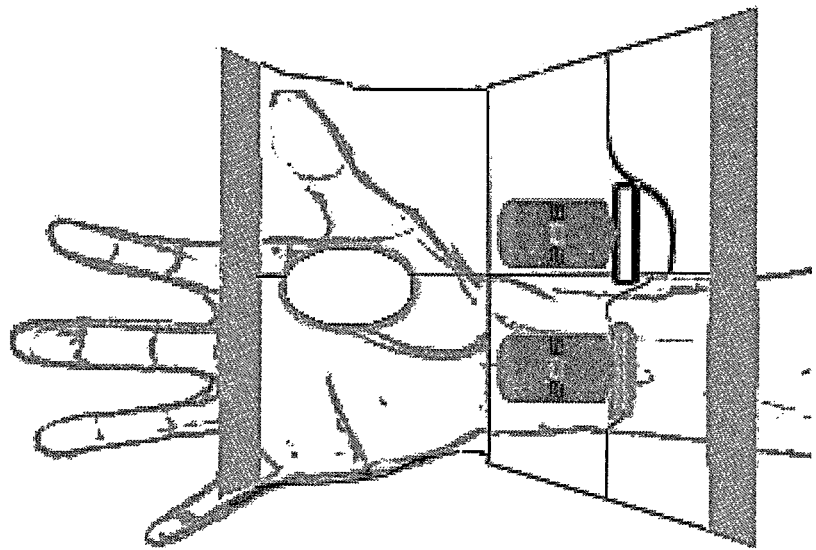
FIG. 15K shows the flat pattern of the therapeutic wrist and hand compression of FIG. 15B overlaid onto an arm to illustrate treatment provided for Stenosing Tenosynovitis (Trigger thumb)
Figure 15J:
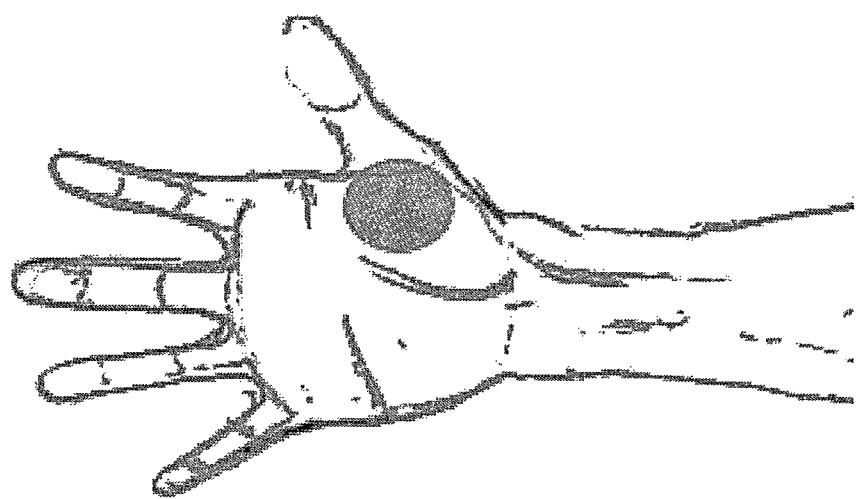
FIG. 15J is an image showing the region of the wrist and hand that may be affected by Stenosing Tenosynovitis (Trigger thumb)
Figure 15M:
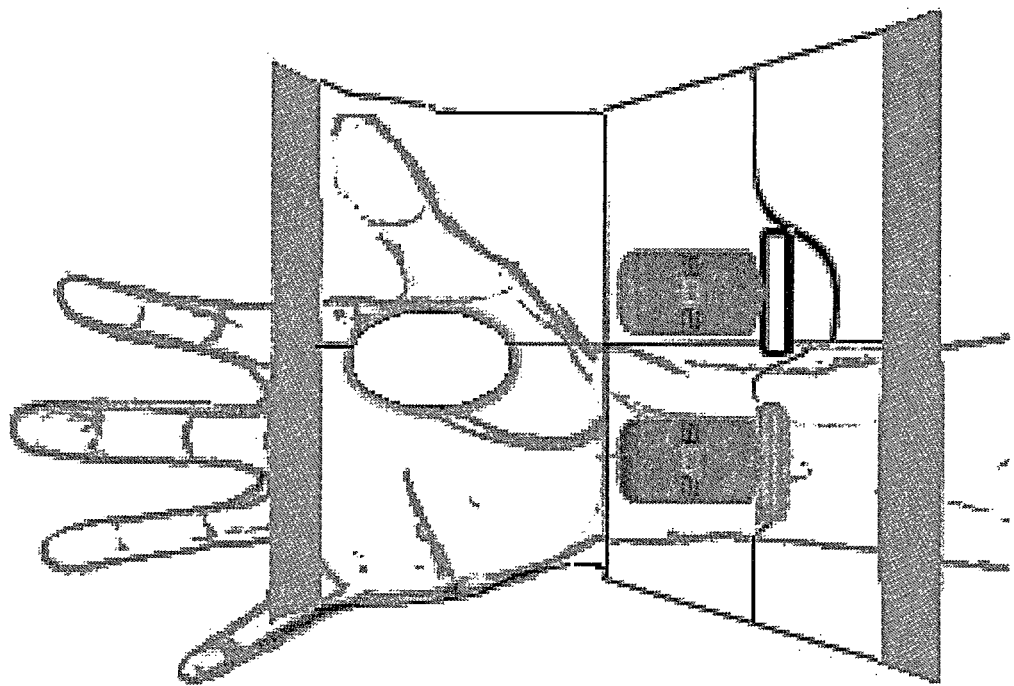
FIG. 15M shows the flat pattern of the therapeutic wrist and hand compression of FIG. 15B overlaid onto an arm to illustrate treatment provided for Triangular FibroCartilage Complex (TFCC)
Figure 15L:
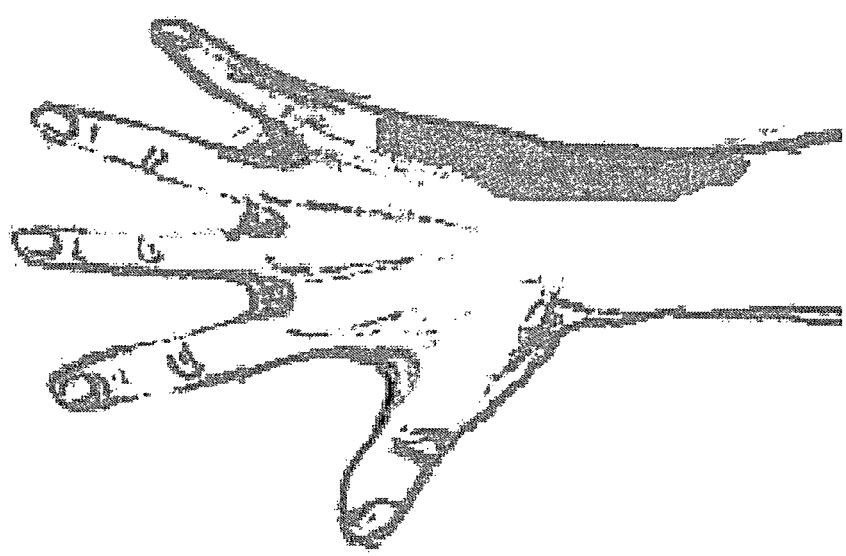
FIG. 15L is an image showing the region of the wrist and hand that may be affected by Triangular FibroCartilage Complex (TFCC)

The application of compression by compression sleeve 202 with the use of heat packs may be used for a person suffering from arthritis of the thumb carpometacarpal (CMC) joint, a biconcave-convex saddle joint, which tends to occur when the normally smooth cartilage surfaces of the wrist joints are worn away and uneven bony surfaces are exposed (see FIG. 15F). The wrist joint can become stiff, swollen, and painful. The application of compression improves mobility of joint.

The application of compression by compression sleeve 202 with the use of cold packs may be used for a person suffering from Stenosing tenosynovitis ("Trigger Thumb"), which occurs when inflammation narrows the space within the sheath that surrounds the tendon in the affected thumb (see FIG. 15G). If trigger thumb is severe, the finger may become locked in a bent position. The application of compression reduce inflammation of tendon.

The application of compression by compression sleeve 202 with the use of cold packs may be used for a person suffering from Triangular FibroCartilage Complex (TFCC), which is a cartilage structure located on the small finger side of the wrist that cushions and supports the small carpal bones in the wrist (see FIG. H). The TFCC keeps the forearm bones (radius and ulna) stable when the hand grasps or the forearm rotates. The application of compression and ice reduces the chances of tearing.

FIG. 15C is an arm compression sleeve 203 for applying compression and thermal treatments (heating or cooling) to a wearer's wrist that may be formed the same as arm compression sleeve 201, but may not extend to have the thumb be received in a hole the same as sleeve 201, and may instead be shorter in length, terminating proximate to the start of the wrist.

Figure 16A:
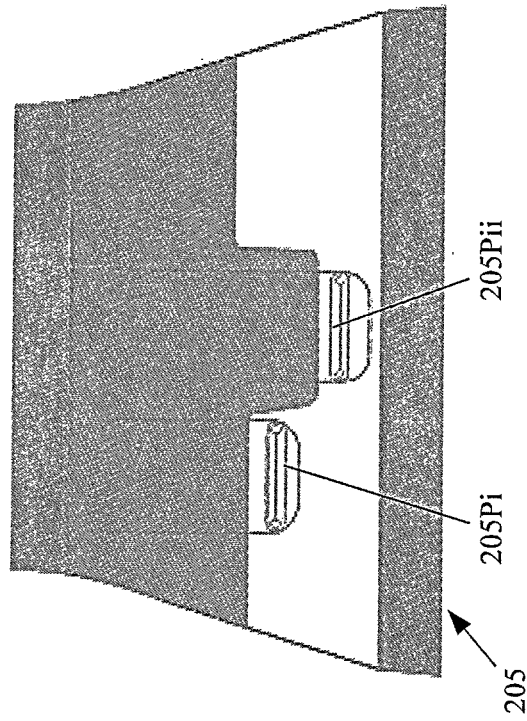
FIG. 16A is a flat pattern for another embodiment of a therapeutic compression garment for treating a wrist of the wearer.
Figure 16B:
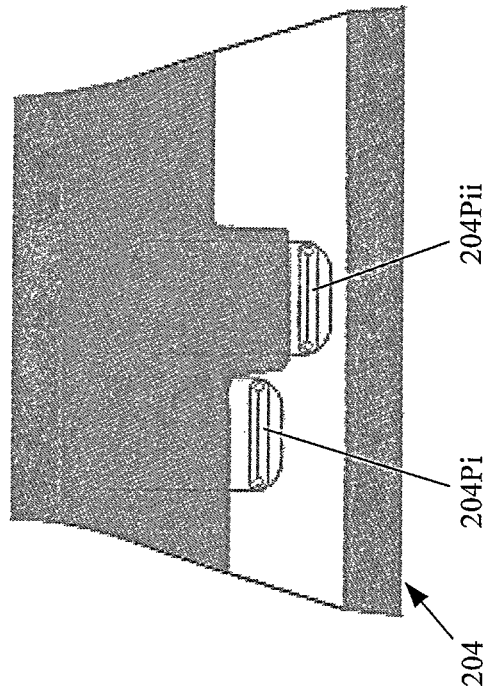
FIG. 16B is a flat pattern for yet another embodiment of a therapeutic compression garment for treating carpal tunnel syndrome at a wrist of the wearer.

FIG. 16A and FIG. 16B respectively illustrate flat patterns for an arm compression sleeve 204 and an arm compression sleeve 205 each of which may be formed similar to the arm compression sleeve 203, but where the arm compression sleeve 204 is proportionally formed to accommodate smaller wearers (i.e., an extra-small, a small, and a medium size arm) and may receive two C1 heat packs into the pocket through openings 204Pi/204Pii, and where the arm compression sleeve 205 is proportionally formed to accommodate larger wearers (i.e., a large, extra-large, and a double extra-large size arm) and may receive one C2 heat pack into a pocket though opening 205Pi and one E1 heat pack into a pocket though opening 205Pii. As noted above, each pocket of the compression garments 204/205 is designed to completely enclose the particularly designed (i.e., sized/shaped) thermal pack after having been fully inserted into the pocket, through the opening (i.e., the layers of high compression material will seal the opening after the heat pack has been fully inserted).

Figure 17B:
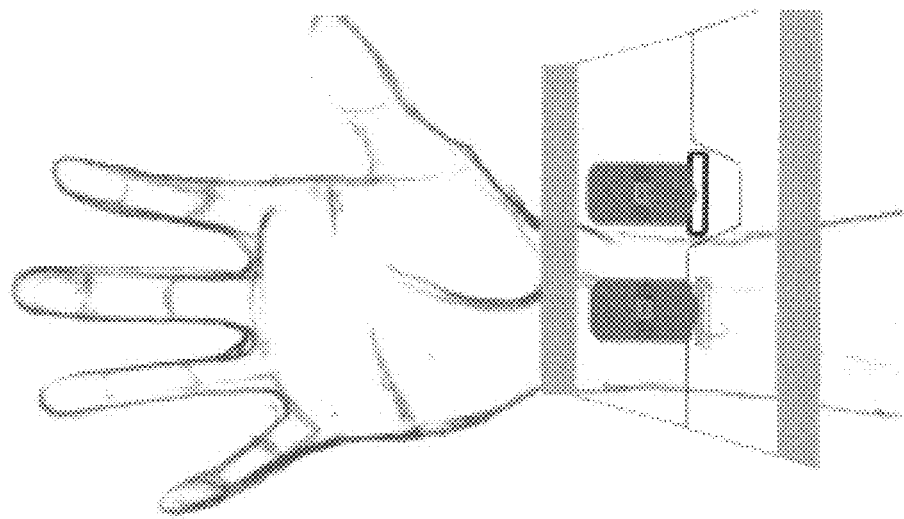
FIG. 17B shows the flat pattern of the therapeutic wrist compression of FIGS. 16C-16D overlaid onto an arm to illustrate treatment provided for carpal tunnel syndrome.
Figure 17A:
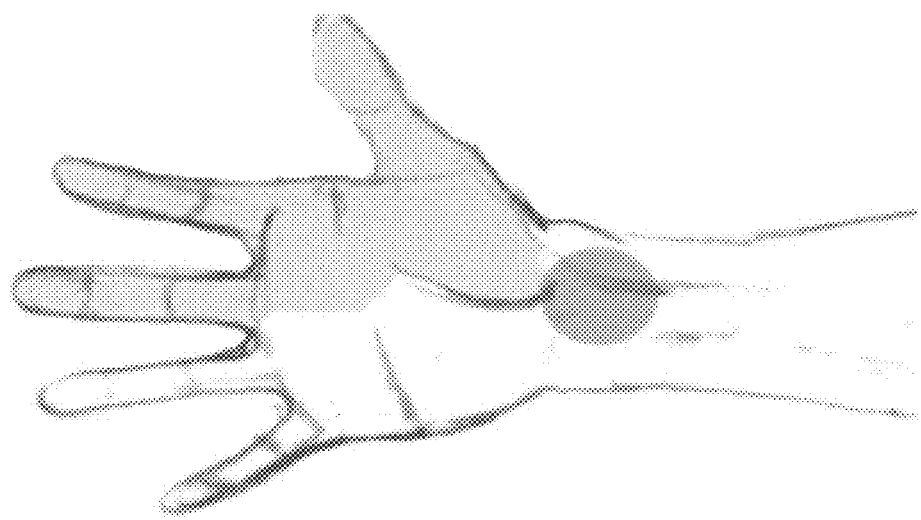
FIG. 17A is an image showing the region of the hand that may be affected by carpal tunnel syndrome.
Figure 17D:
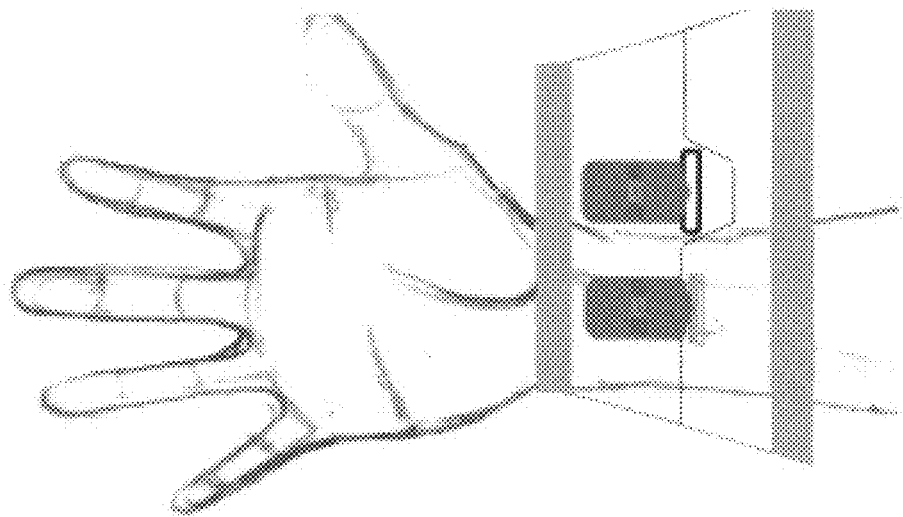
FIG. 17D shows the flat pattern of the therapeutic wrist compression of FIGS. 16C-16D overlaid onto an arm to illustrate treatment provided for De Quervain's Tenosynovitis.
Figure 17C:
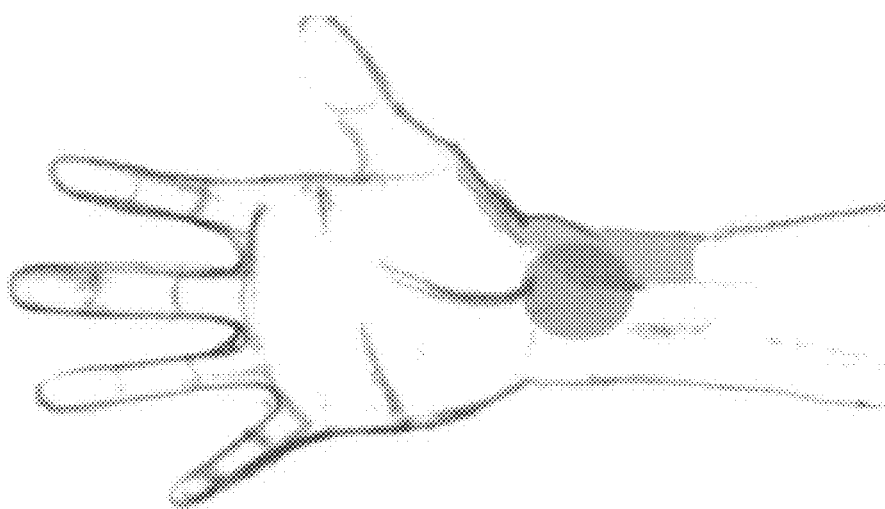
FIG. 17C is an image showing the region of the hand that may be affected by De Quervain's Tenosynovitis (DQT)

FIG. 16C is a flat pattern for a therapeutic arm compression sleeve 206 for treating carpal tunnel syndrome at a wrist of the wearer, being formed similar to the arm compression sleeve 203, except that each of the pockets may be particularly formed to hold the cold pack (e.g., C1 or C2) when inserted in the opposite direction, such that the pointed end of the gonfalon shape may be protruding out from the end of the pocket and its tip may thus be gripped by the user for removal and replacement of the pack. The deepest end of the pocket may be generally rectangular with rounded corners as shown in FIG. 16C. FIG. 16C is shown prior to inserting of the heat/cold packs into the pockets formed therein, and FIG. 16D is the flat pattern of FIG. 16C shown after inserting of the heat/cold packs into the pockets. The carpal tunnel is located in the wrist and contains the medial nerve. The medial nerve runs from the forearm to the hand and controls feeling on the inside of the hand around the thumb, index finger, and long fingers. When the medial nerve is compressed, it can lead to numbness, burning or tingling of the hand and the affected fingers (see FIG. 17A). The compression and the thermal cooling provided by cold packs used in the pockets of compression sleeve 206 may be used to reduce pressure on the medial nerve. De Quervains Tenosynovitis (DQT) is inflammation of tendons on the side of the wrist at the base of the thumb (see FIG. 17B). These tendons include the extensor pollicis brevis and the abductor pollicis longus tendons (i.e., the first compartment tendons—see FIG. 15Ci), which extend the joints of the thumb. A high compression level and thermal cooling provided by cold packs used in pockets of the compression sleeve 206 may treat DQT by reducing rubbing of the tendons in the first dorsal compartment (see FIG. 15Ci).

Figure 18:
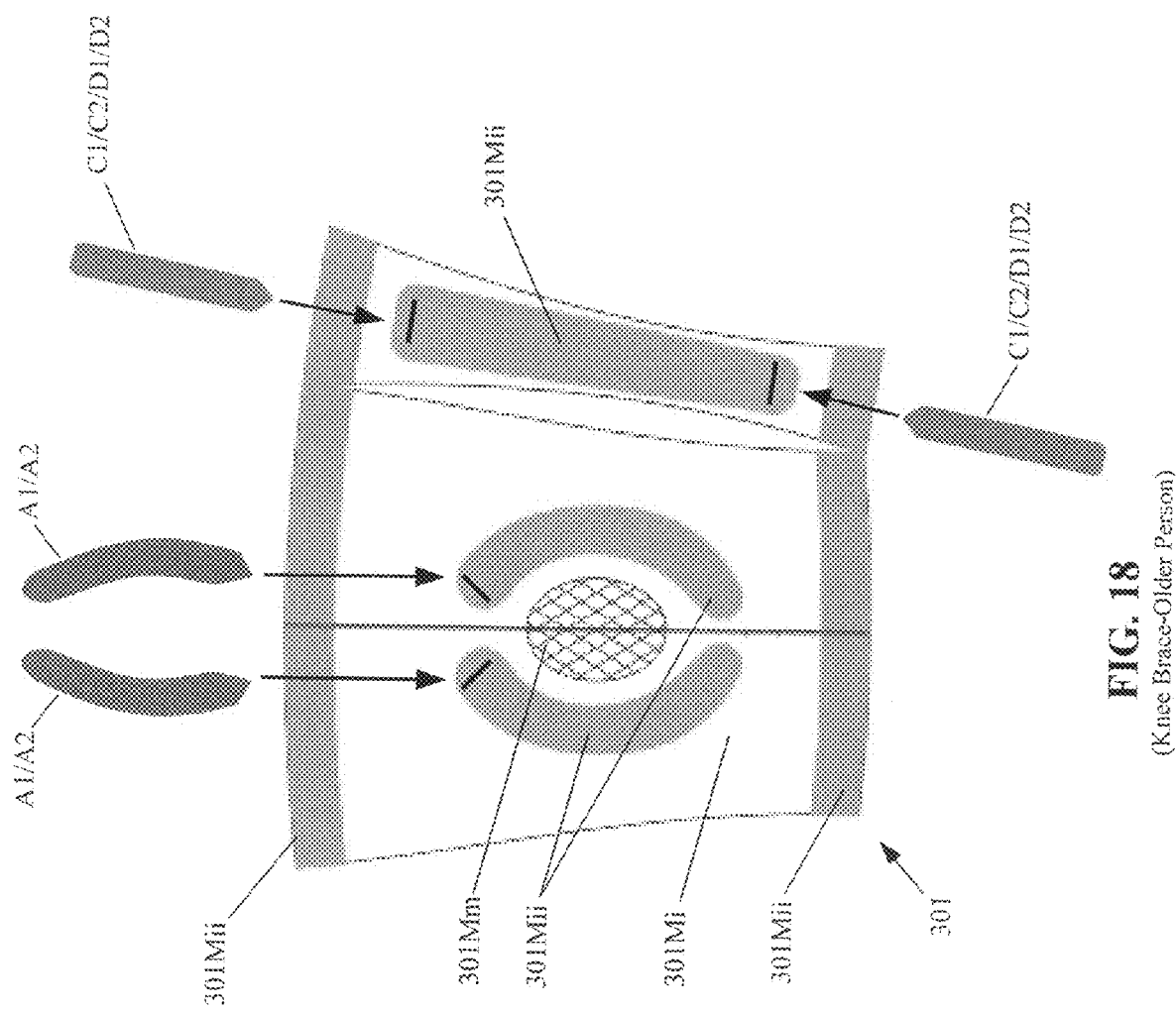
FIG. 18 is a flat pattern for a front portion of a therapeutic knee compression for an older person, having openings formed to receive heat/cold packs into pockets therein to apply heat and/or cold therapy under compression to regions of a leg.

FIG. 18 is a compression sleeve 301 configured for applying compression and thermal treatments (heating or cooling) to a wearer's knee joint and surrounding area, and may include: a primary layer of material 301Mi, which may be elastic; a liner that creates particularly positioned and shaped pockets proximate to the knee region to receive one or more custom heat/cold packs through openings; and particularly located layers of high compression material 301Mii that overlie the pocket(s) and may overlie other areas as well (e.g., the bands at the two ends of the sleeve to help retain the sleeve in position at the knee). A mesh material 301Mm may be used at the knee, as shown in FIG. 18, and may be the only layer used thereat, or may instead be used in combination with the elastic primary layer of material 301Mi, which may be continuous throughout the sleeve. Two arcuate regions of the high compression material 301Mii may surround the mesh material 301Mm that is to be positioned over the wearer's knee, and the arcuate regions may have respective pockets underneath each region to receive either an A1 heat pack or an A2 heat pack. These particularly positioned pockets are formed such that the thermal packs A1 and A2 surround the patella, except for a small portion at the upper and lower ends where the pockets begin and terminate (i.e., surrounding about 85% to about 90% of the patella), as seen in FIG. 18. The high compression material 301Mii positioned to overlie the pockets may serve to prevent local deformation of the sleeve (and local deformation in the other garments where used), and improves the effectiveness of the heat/cold packs positioned underneath. A straight region of the high compression material 301Mii may be centered on the back side of the sleeve, and may receive either one single long heat pack therein, or may instead receive two elongated heat packs (e.g., C1/C2/D1/D2 sized heat packs) that may be inserted from opposite ends of the pockets through two different openings (where the pocket may be sized in every case to match the particular heat/cold pack size). As noted above, each pocket of the compression garment 301 is designed to completely enclose the particularly designed (i.e., sized/shaped) thermal pack after having been fully inserted into the pocket, through the opening (i.e., the layers of high compression material will seal the opening after the heat pack has been fully inserted).

Figure 21:
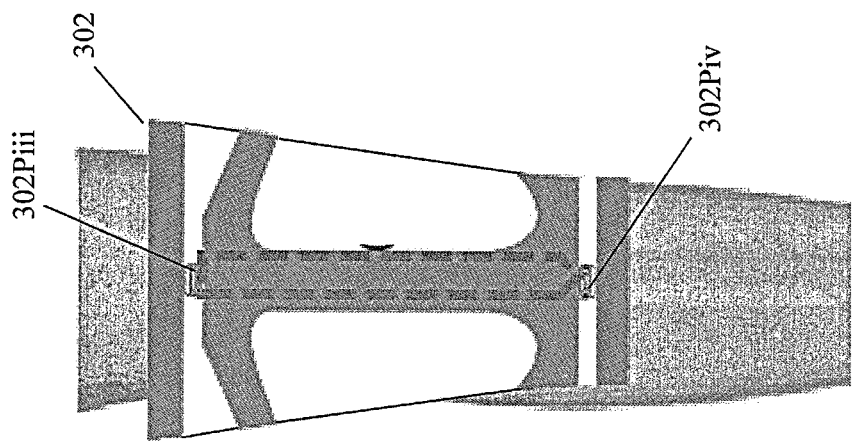
FIG. 21 is the rear of the therapeutic knee compression shown in FIG. 20, but is shown with a single long heat pack positioned in the pocket, instead of two smaller length heat packs.
Figure 20:
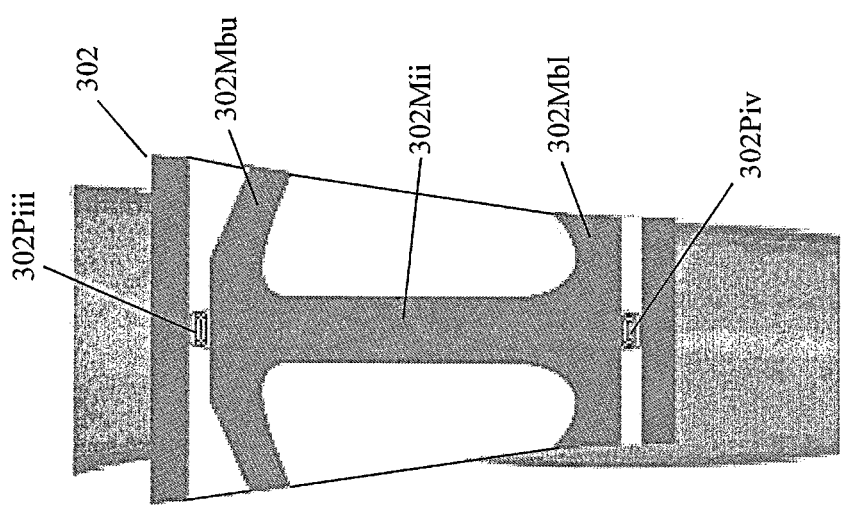
FIG. 20 is a view of the rear of the therapeutic knee compression of FIG. 19.
Figure 19:
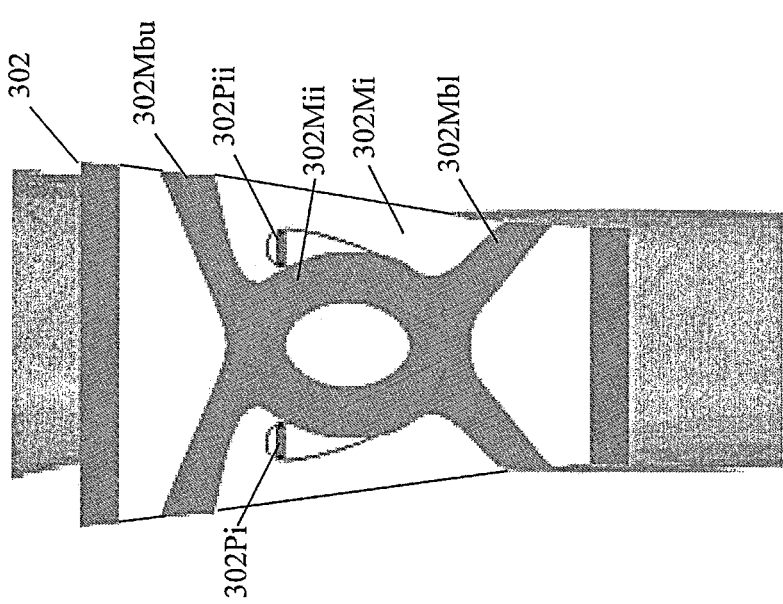
FIG. 19 is a view of the front of another embodiment of a therapeutic knee compression.

FIG. 19 and FIG. 20 are views of the front and rear of a knee compression sleeve 302 configured for applying compression and thermal treatments to a wearer's knee joint and surrounding area using: a primary layer of elastic material 302Mi; a liner that creates particularly positioned and shaped pockets; and particularly located layers of high compression material 302Mii that overlie the pockets. The compression sleeve 302 may be formed similar to the compression sleeve 301 but instead of having the two separate arcuate regions of high compression material 302Mii on opposite sides of the knee, they may be joined to form a continuous oval shaped region, which may transition at its upper end to an upper band 302Mbu that may encircle the leg above the knee, and may transition at its lower end to a lower band 302Mbl that may encircle the leg below the knee, which continuous bands of high compression material being coupled to the oval band may further the application of uniform compressive pressure to the heat packs at the noted locations and further improve their efficacy. (Note that this arrangement for the high compression material, including the oval and leg-encircling portions, may also be used on the compression sleeve 301 to further improve the application of thermal treatments provided therein). The upper and lower bands 302Mbu and 302Mbl may also merge (i.e., be integral) with the high compression material 302Mii located at the back of the sleeve, as shown in FIG. 20. The compression sleeve 302 may receive an A1 or an A2 heat pack into each of the front pockets through openings 302Pi and 302Pii, and may also receive either two elongated heat packs (C1/C2) into the rear pocket though openings 302Piii and 302Piv (FIG. 20—C1/C2/D1/D2) or only one elongated heat pack (D1/D1) as shown in FIG. 21.

Figure 22B:
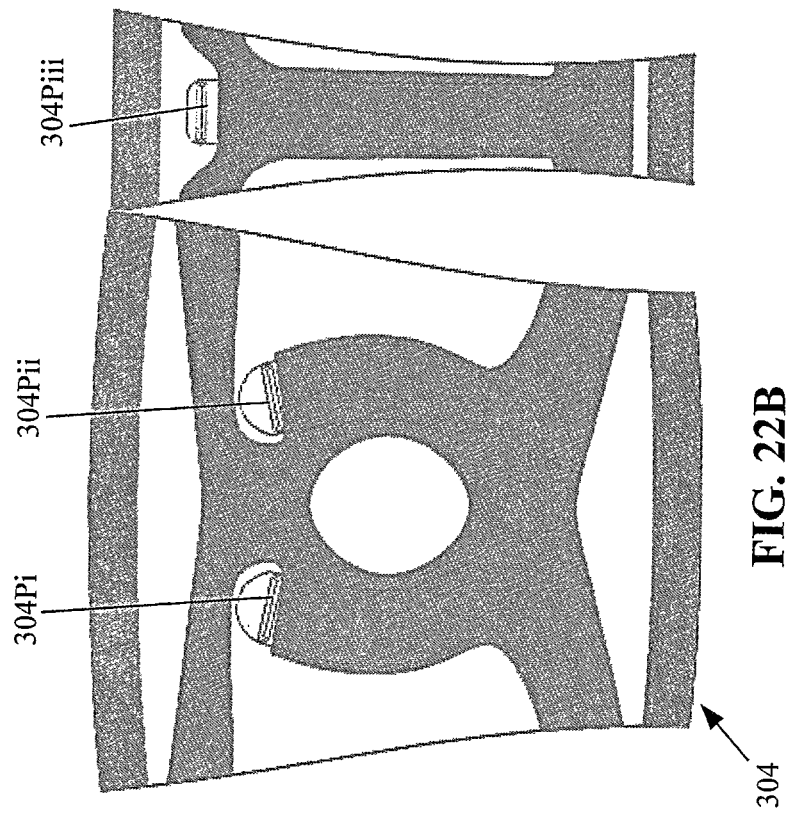
FIG. 22B is the flat pattern of FIG. 22A, but shown with the compression and the heat/cold packs being sized for a large, an extra-large, and a double extra-large wearer.
Figure 22A:
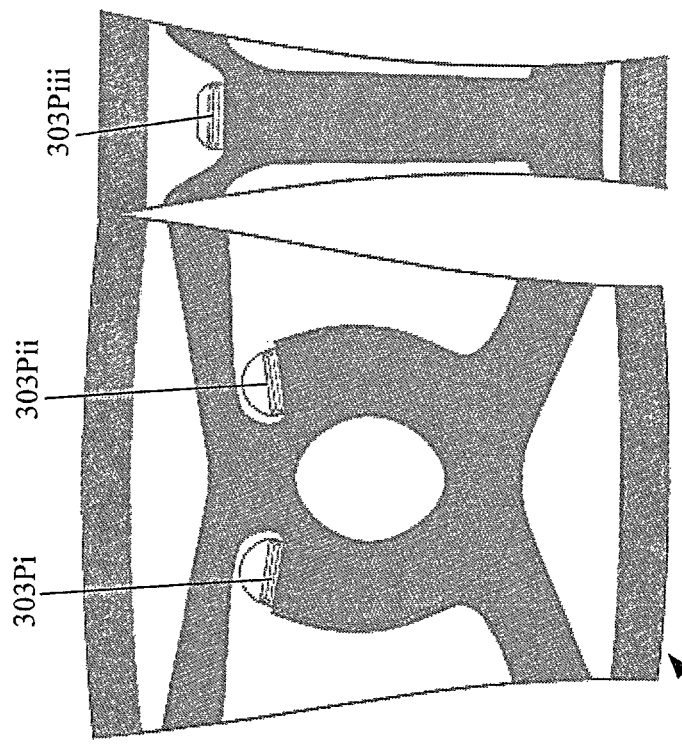
FIG. 22A is a flat pattern for another embodiment of a therapeutic knee compression, being configured for an older person, with the compression and the heat/cold packs sized for an extra-small, small, and medium sized wearer.
Figure 23B:
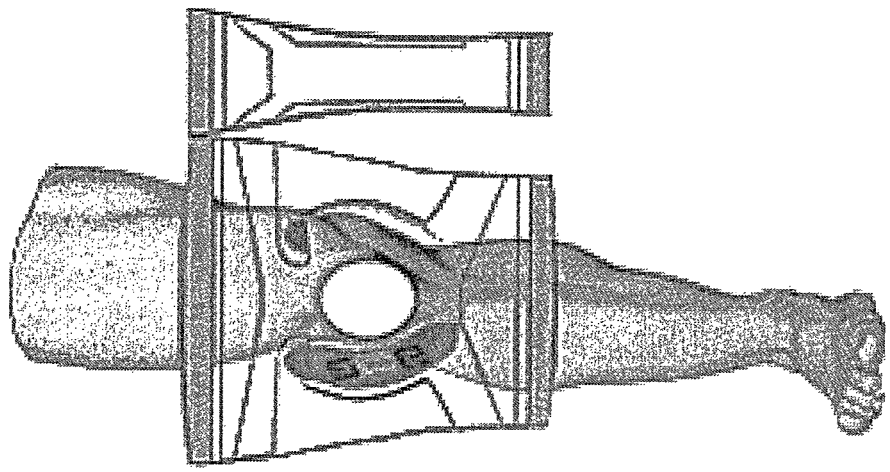
FIG. 23B shows the flat pattern of the therapeutic knee compression of FIGS. 22A-22B overlaid onto a leg to illustrate treatment provided for quadriceps muscle strain.
Figure 23A:
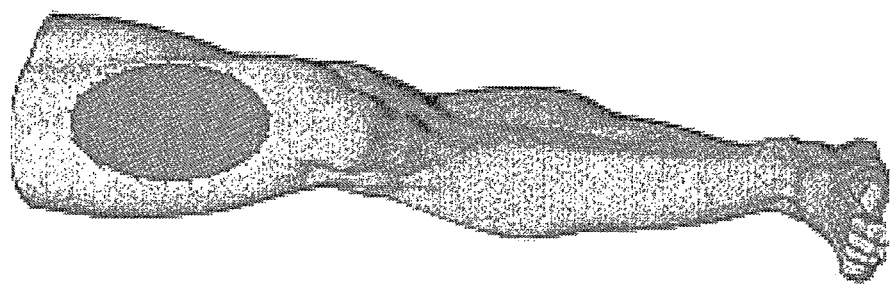
FIG. 23A is an image showing the region of the leg that may be affected by quadriceps muscle strain.
Figure 23D:
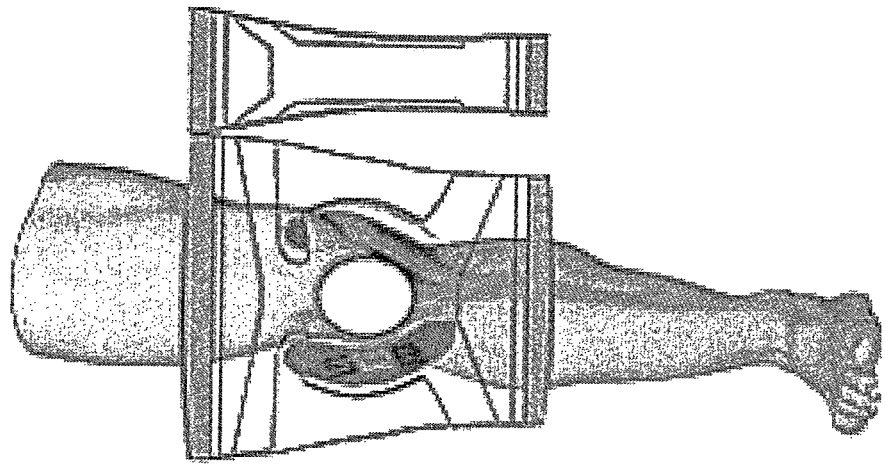
FIG. 23D shows the flat pattern of the therapeutic knee compression of FIGS. 22A-22B overlaid onto a leg to illustrate treatment provided for quadriceps tendon strain.
Figure 23C:
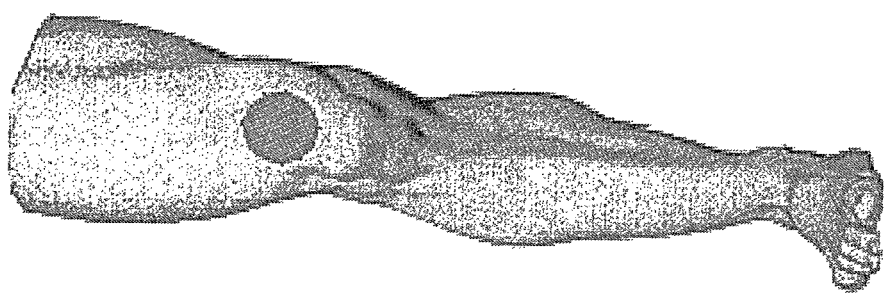
FIG. 23C is an image showing the region of the leg that may be affected by quadriceps tendon strain.
Figure 23F:
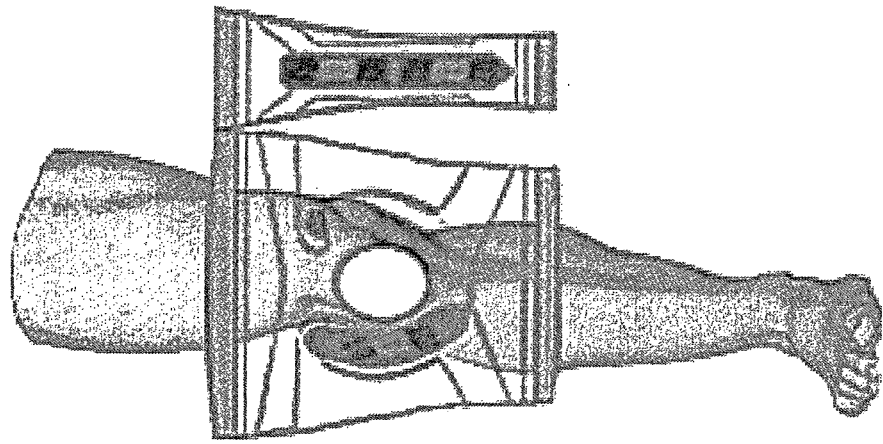
FIG. 23F shows the flat pattern of the therapeutic knee compression of FIGS. 22A-22B overlaid onto a leg to illustrate treatment provided for osteoarthritis.
Figure 23E:
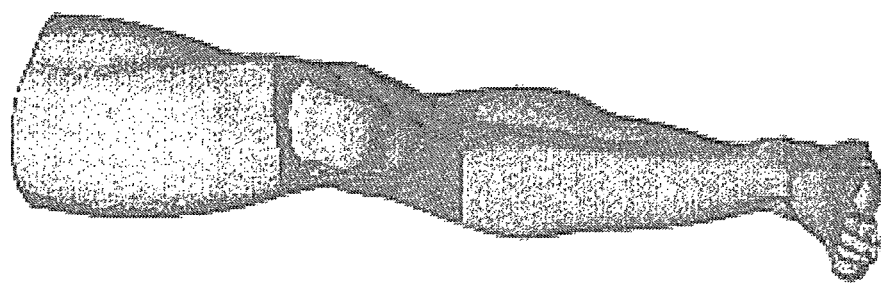
FIG. 23E is an image showing the region of the leg that may be affected by osteoarthritis.
Figure 23H:
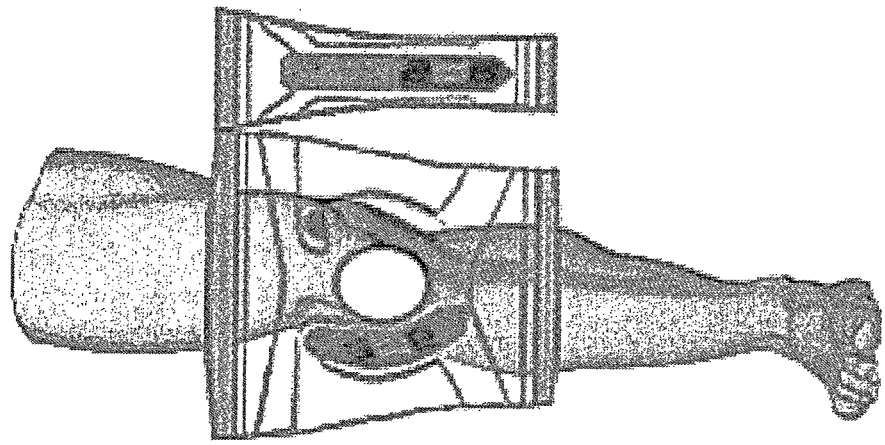
FIG. 23H shows the flat pattern of the therapeutic knee compression of FIGS. 22A-22B overlaid onto a leg to illustrate treatment provided for rheumatoid arthritis.
Figure 23G:
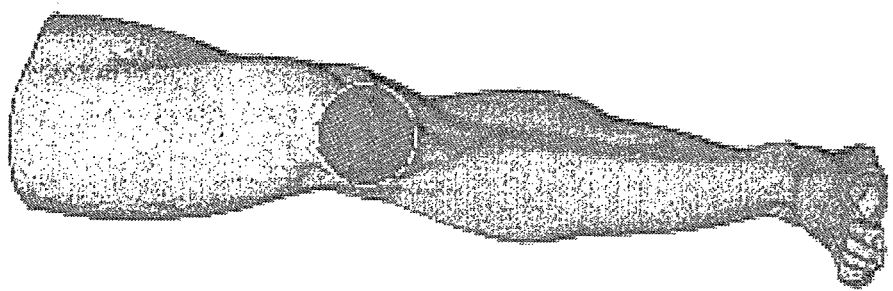
FIG. 23G is an image showing the region of the leg that may be affected by rheumatoid arthritis.
Figure 23J:
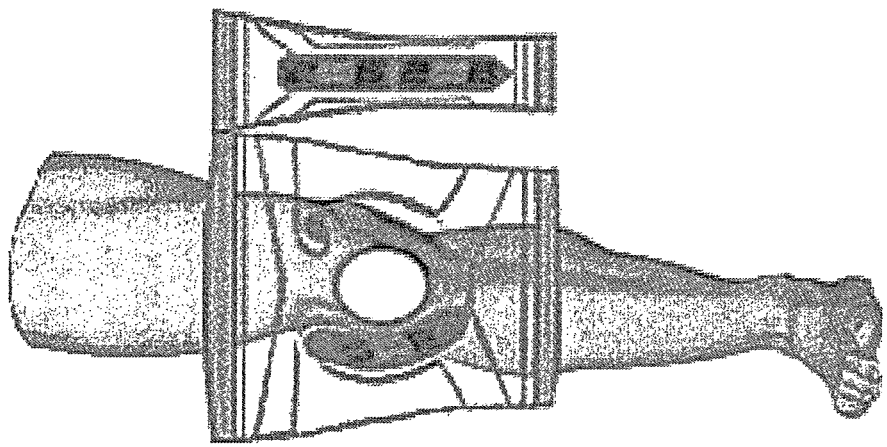
FIG. 23J shows the flat pattern of the therapeutic knee compression of FIGS. 22A-22B overlaid onto a leg to illustrate treatment provided for a bow legged condition.
Figure 23I:
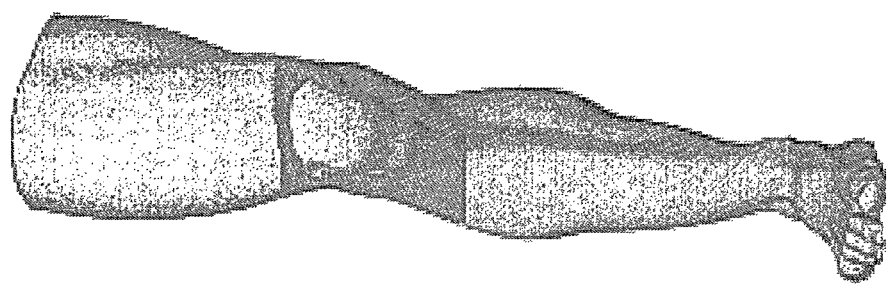
FIG. 23I is an image showing the region of the leg that may be bow legged.
Figure 23L:
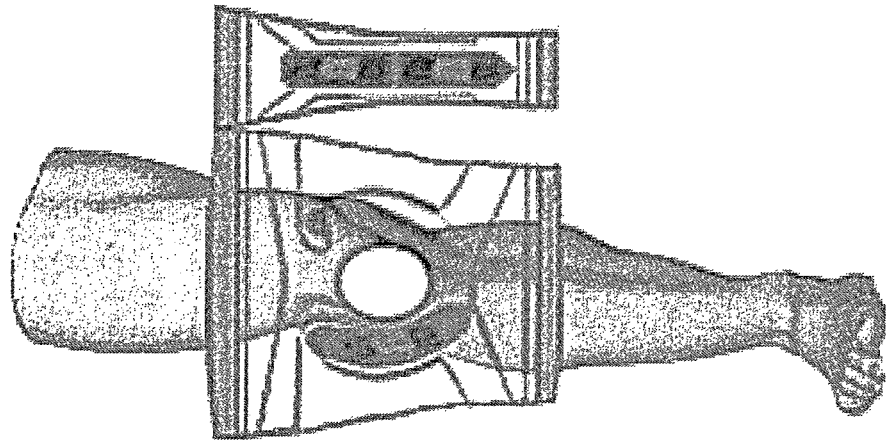
FIG. 23L shows the flat pattern of the therapeutic knee compression of FIGS. 22A-22B overlaid onto a leg to illustrate treatment provided for a knock knee condition.
Figure 23K:
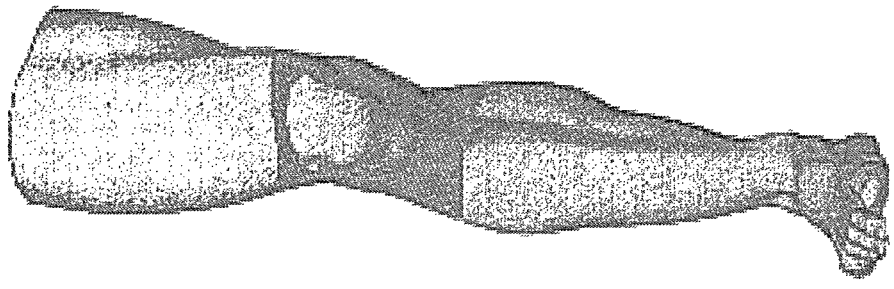
FIG. 23K is an image showing the region of the leg that may be affected by knock knee.
Figure 23N:
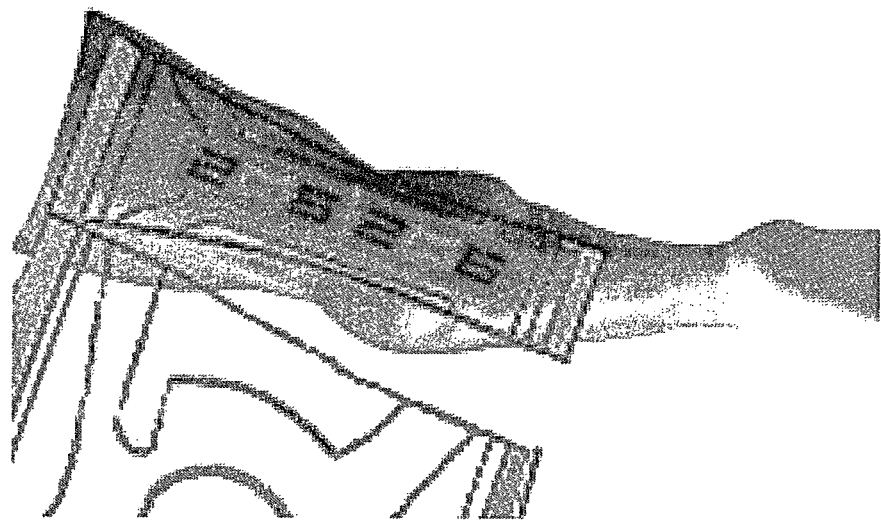
FIG. 23N shows the flat pattern of the therapeutic knee compression of FIGS. 22A-22B overlaid onto a leg to illustrate treatment provided for a hamstring injury.
Figure 23M:
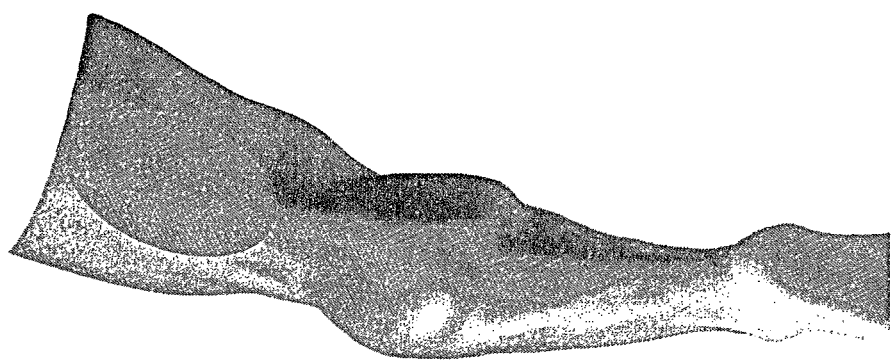
FIG. 23M is an image showing the region of the leg that may be affected by a hamstring injury.
Figure 23P:
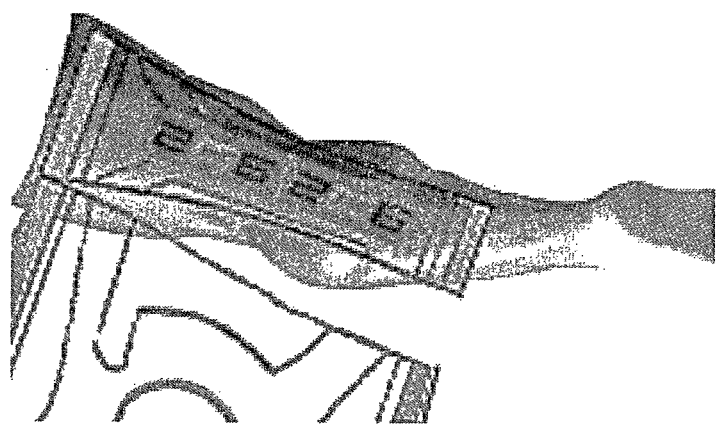
FIG. 23P shows the flat pattern of the therapeutic knee compression of FIGS. 22A-22B overlaid onto a leg to illustrate treatment provided for a strain of the proximal calf muscle.
Figure 23O:
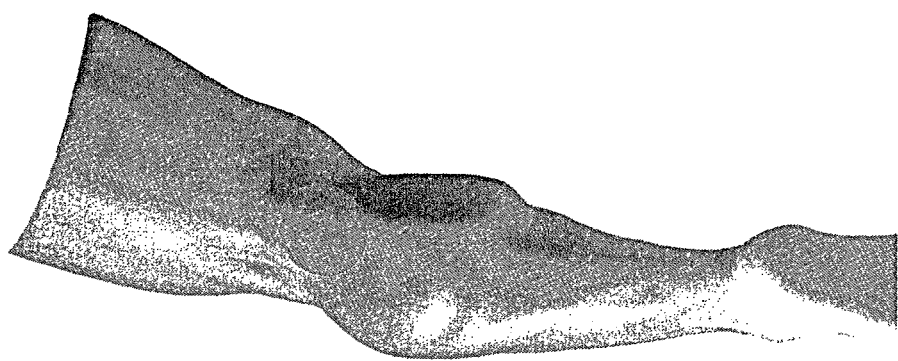
FIG. 23O is an image showing the region of the leg that may be affected by a strain of the proximal calf muscle.
Figure 23R:
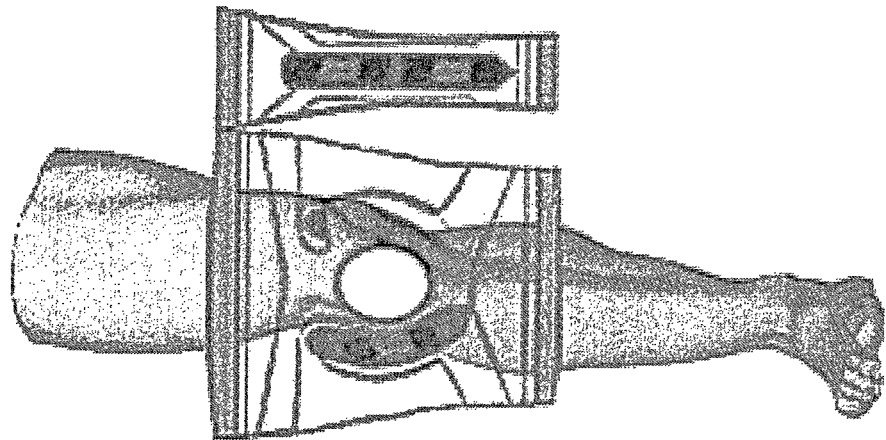
FIG. 23R shows the flat pattern of the therapeutic knee compression of FIGS. 22A-22B overlaid onto a leg to illustrate treatment provided for patellar tendonitis.
Figure 23Q:
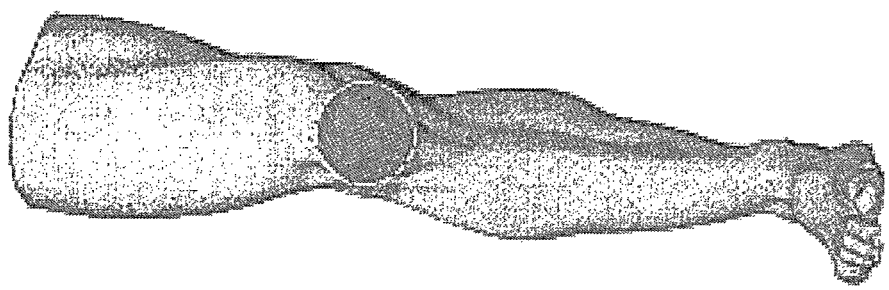
FIG. 23Q is an image showing the region of the leg that may be affected by patellar tendonitis.
Figure 25B:
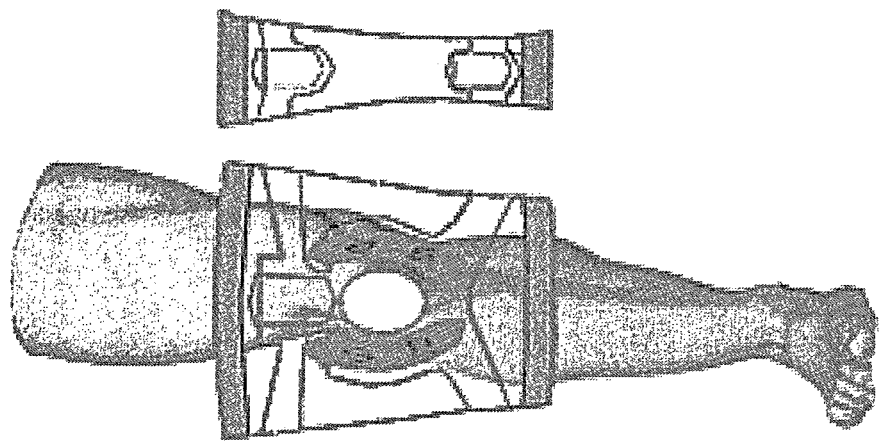
FIG. 25B shows the flat pattern of the therapeutic knee compression of FIGS. 24A-24B overlaid onto a leg to illustrate treatment provided for a leg that may be affected by MCL/LCL sprains.
Figure 25A:
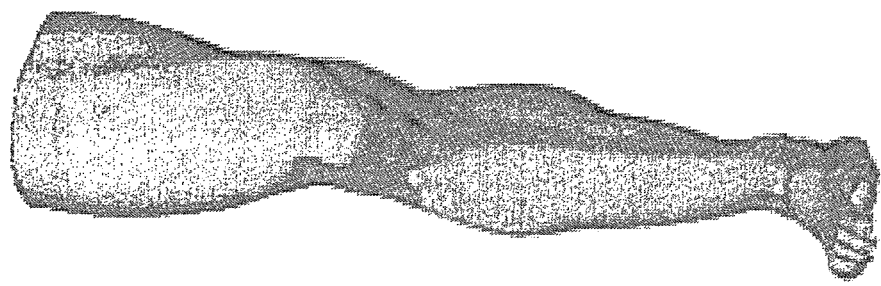
FIG. 25A is an image showing the region of the leg that may be affected by MCL/LCL sprains.

FIG. 22A and FIG. 22B respectively illustrate flat patterns for a knee compression sleeve 303 and a knee compression sleeve 304 each of which may be formed similar to the knee compression sleeve 302 to be used for an older person, but where the knee compression sleeve 303 is proportionally formed to accommodate smaller wearers (i.e., an extra-small, a small, and a medium size leg) and may receive two A1 heat packs into respective pockets through openings 303Pi/303Pii and one D1 heat pack into rear pocket through opening 303Piii, and where the knee compression sleeve 304 is proportionally formed to accommodate larger wearers (i.e., a large, extra-large, and a double extra-large size leg) and may receive two A2 heat packs into respective pockets through openings 304Pi/304Pii and one D1 heat pack into the rear pocket through opening 304Piii. It is noted that the triangular tip of the heat packs may permit them to be positioned within pockets that are very close together, or pockets that may even be interconnected to form one large arcuate (nearly circular) pocket, so that the distal ends of the heat packs may contact each other, to better provide for thermal treatment around a greater percentage of the periphery of the patella than is shown in FIG. 22A-22B, and shown in FIG. 18. The use of the knee compression sleeves 301/302/303/304 and the use of heat or "ice" (i.e., a heat pack or a cold pack) within the pockets therein may be injury and/or location specific as follows (see FIGS. 23A-23R):

Quadriceps Muscle Strain (see FIGS. 23A and 23B Heat/Ice with High Compression) The quadriceps muscle is actually a group of four muscles in the front thigh that connect to the knee just below the knee cap;

Quadriceps Tendon Strain (see FIGS. 23C and 23D Heat/Ice with High Compression) The quadriceps tendon attaches the quadriceps muscles to the patella. The patella is attached to the shinbone (tibia) by the patellar tendon. Working together, the quadriceps muscles, quadriceps tendon and patellar tendon straighten the knee;

Osteoarthritis (see FIGS. 23E and 23F—Heat/ice with High Compression) Osteoarthritis (OA) is caused by aging joints, injury, and obesity. OA symptoms include joint pain and stiffness;

Rheumatoid arthritis (see FIGS. 23G and 23H—Ice with High or low compression) Rheumatoid arthritis (RA) is an autoimmune disease that can cause joint pain and damage throughout your body;

Bow Legged (see FIGS. 23I and 23J—Heat/Ice with High Compression) Bowlegs is a condition in which a person's legs appear bowed out, meaning the knees stay wide apart even when the ankles are together. Bowlegs is also known as congenital genu varum;

Knock-Knee (see FIGS. 23K and 23L—Heat/ice with High Compression) Genu valgum, known as knock-knees, is a knee misalignment that turns the knees inward. When people with knock-knees stand up with their knees together, there's a gap of 3 inches or more between their ankles. This is because the knees are bent so far inward;

Hamstring (Distal) (see FIGS. 23M and 23N—Heat/Ice with High Compression);

Calf Strain (Proximal) (see FIGS. 23O and 25P—Heat/Ice with High compression);

Patellar Tendinitis (see FIGS. 23Q and 23R—Ice with High Compression).

Figure 24B:
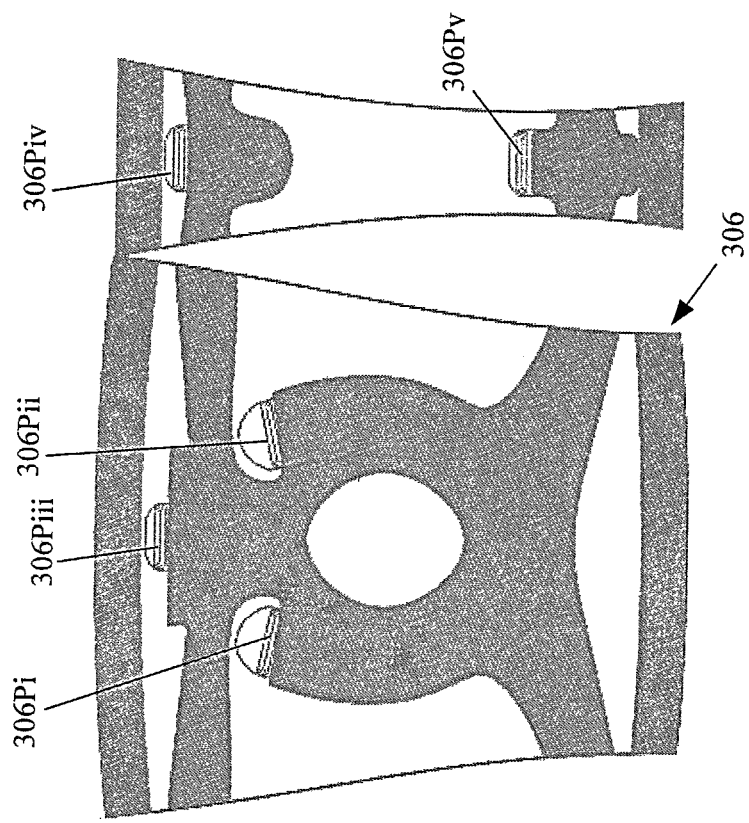
FIG. 24B is the flat pattern of FIG. 24A, but shown with the compression and the heat/cold packs being sized for a large, an extra-large, and a double extra-large wearer.
Figure 24A:
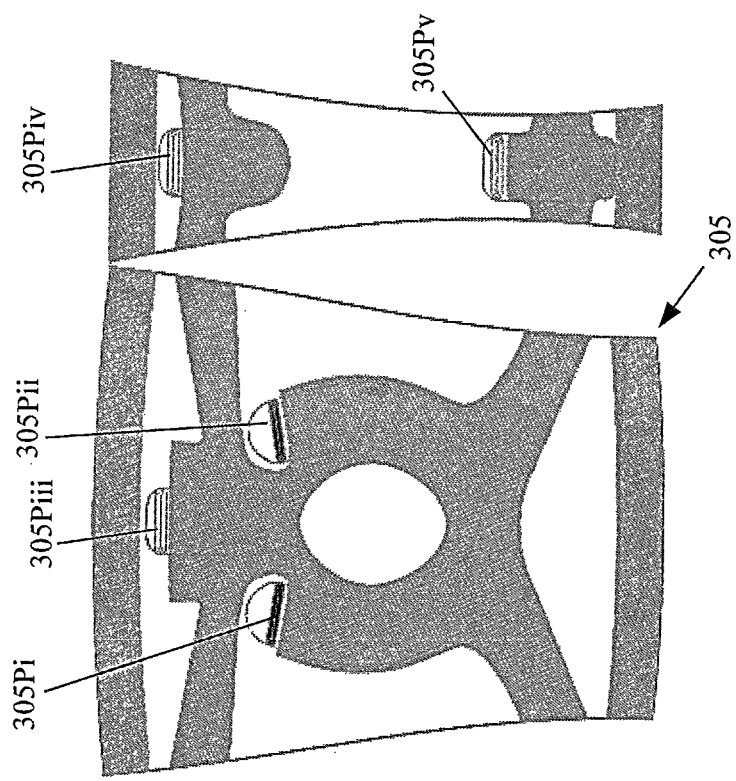
FIG. 24A is a flat pattern for another embodiment of a therapeutic knee compression, being configured for a younger person, with the compression and the heat/cold packs sized for an extra-small, a small, and a medium sized wearer.

FIG. 24A and FIG. 24B respectively illustrate flat patterns for a knee compression sleeve 305 and a knee compression sleeve 306 each of which may be formed similar to the knee compression sleeves 303/304 but are instead particularly formed to be used for a younger person, where the knee compression sleeve 305 is proportionally formed to accommodate smaller wearers (i.e., an extra-small, a small, and a medium size leg) and may receive two A1 heat packs into respective pockets through openings 305Pi/305Pii and a one C1 heat pack through opening 305Piii, and two C1 heat packs into respective rear pockets through openings 305Piv/305Pv, and where the knee compression sleeve 306 is proportionally formed to accommodate larger wearers (i.e., a large, extra-large, and a double extra-large size leg) and may receive two A2 heat packs into respective pockets through openings 306Pi/306Pii and a one C2 heat pack through opening 306Piii, and two C2 heat packs into respective rear pockets through opening 306Piv/306Pv. (Note the C2 heat pack positioned above the patella provides a large surface area that is configured to provide efficacious thermal treatments to the tendon connected to the quadriceps muscle).

The use of the knee compression sleeves 305/306 and the use of heat or "ice" (i.e., a heat pack or a cold pack) within the pockets therein may be injury and/or location specific as follows (see FIGS. 25A-25L):

MCL/LCL Sprains (see FIGS. 25A and 25B—Ice with High Compression) Sprains of the Medial Collateral Ligament (MCL) and Lateral Collateral Ligament (LCL) are knee injuries. The MCL is the ligament located on the inside of the knee joint. It links the thighbone (femur) and shinbone (tibia). The LCL runs along the outside of the knee joint.

Figure 25D:
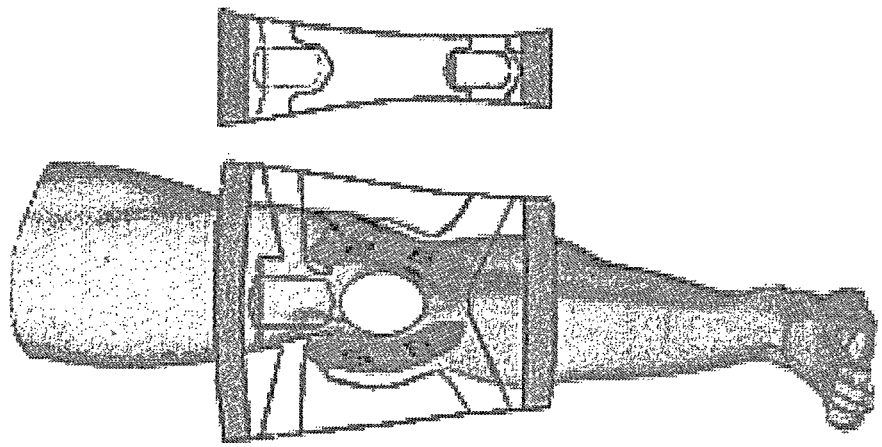
FIG. 25D shows the flat pattern of the therapeutic knee compression of FIGS. 24A-24B overlaid onto a leg to illustrate treatment provided for a leg that may be affected by CMP/PFPS Chondromalacia Patella/PatelloFemoral Pain Syndrome.
Figure 25C:
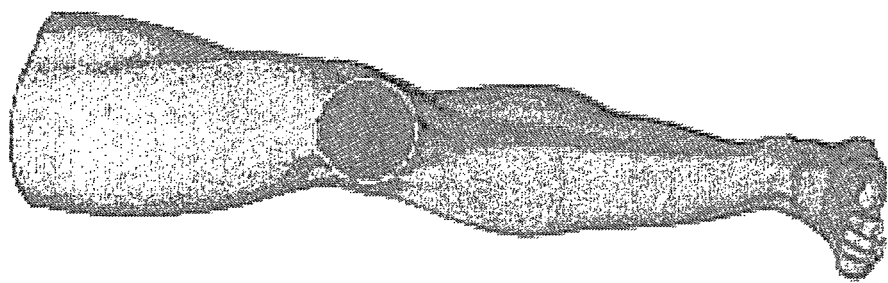
FIG. 25C is an image showing the region of the leg that may be affected by CMP/PFPS Chondromalacia Patella/PatelloFemoral Pain Syndrome.
Figure 25F:
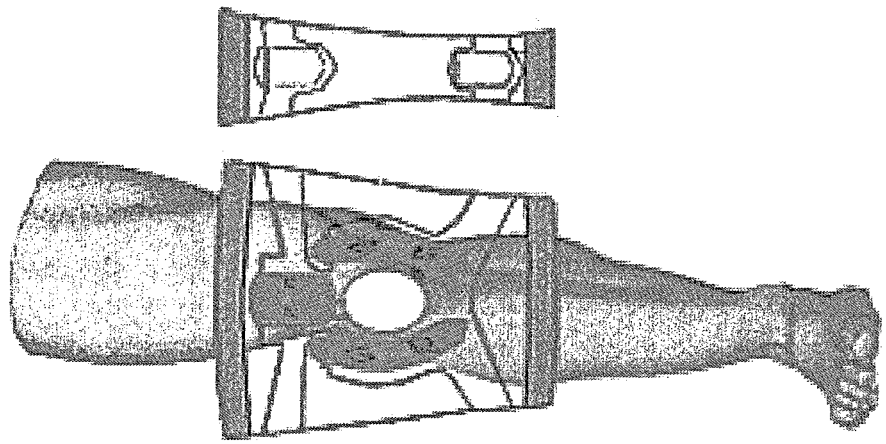
FIG. 25F shows the flat pattern of the therapeutic knee compression of FIGS. 24A-24B overlaid onto a leg to illustrate treatment provided for a leg that may be affected by Jumper's Knee—Patellar Tendinitis.
Figure 25E:
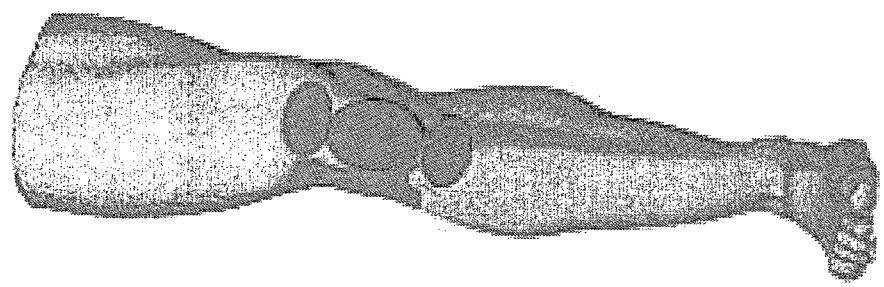
FIG. 25E is an image showing the region of the leg that may be affected by Jumper's Knee—Patellar Tendinitis.
Figure 25H:
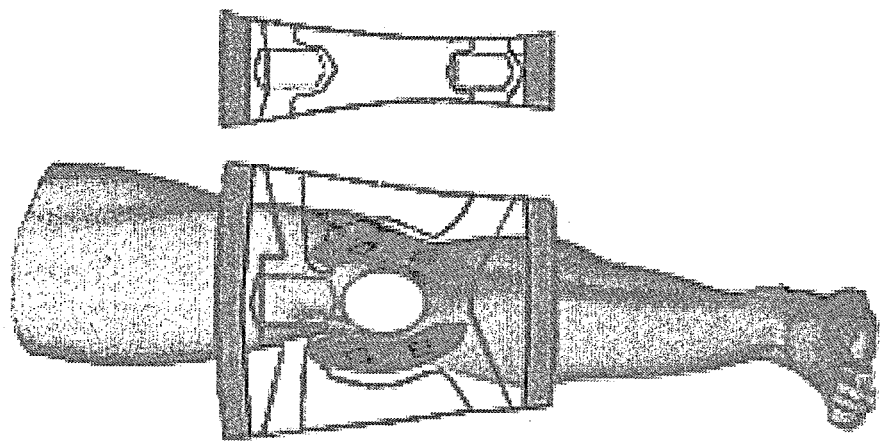
FIG. 25H shows the flat pattern of the therapeutic knee compression of FIGS. 24A-24B overlaid onto a leg to illustrate treatment provided for a leg that may be affected by an Osgood Schlatter—Tibial Tubercle Apophyseal traction injury.
Figure 25G:
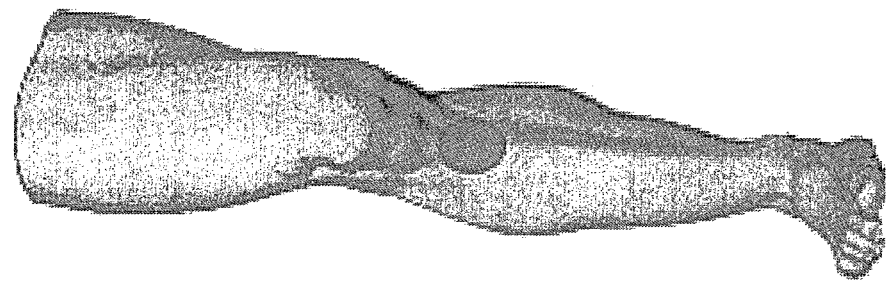
FIG. 25G is an image showing the region of the leg that may be affected by an Osgood Schlatter—Tibial Tubercle Apophyseal traction injury.
Figure 25J:
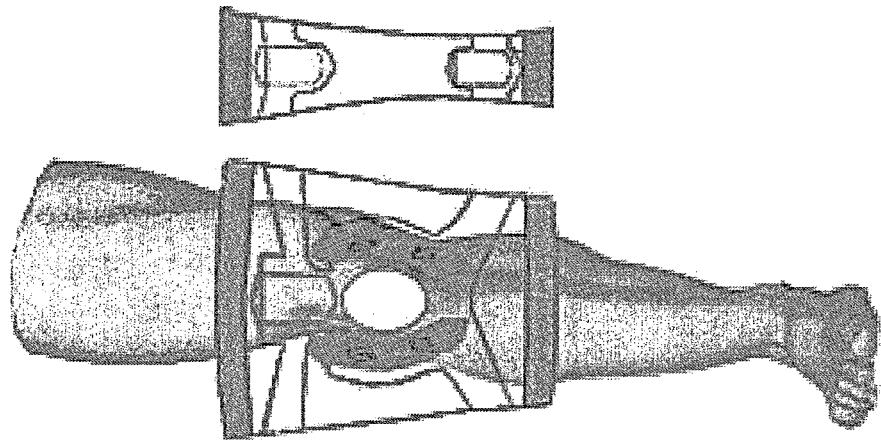
FIG. 25J shows the flat pattern of the therapeutic knee compression of FIGS. 24A-24B overlaid onto a leg to illustrate treatment provided for a leg that may be affected by Medial Plica Syndrome.
Figure 25I:
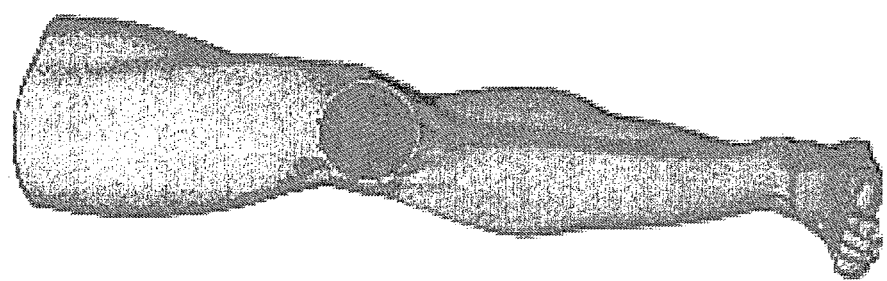
FIG. 25I is an image showing the region of the leg that may be affected by Medial Plica Syndrome.
Figure 25L:
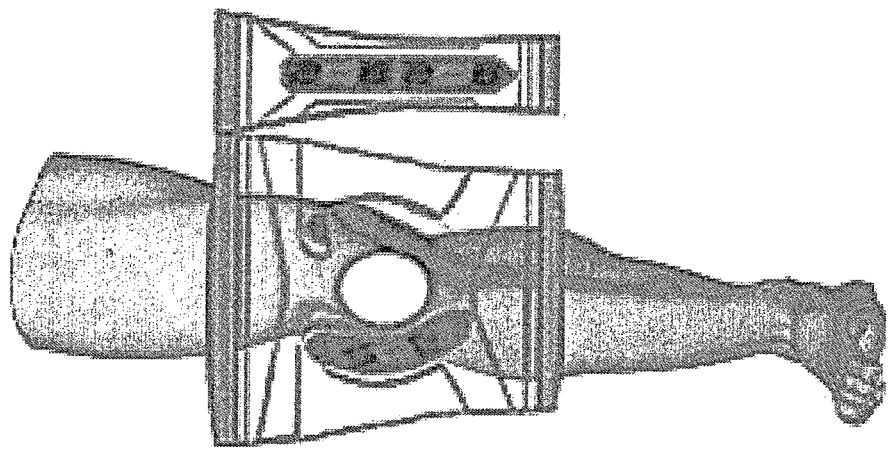
FIG. 25L shows the flat pattern of the therapeutic knee compression of FIGS. 24A-24B overlaid onto a leg to illustrate treatment provided for a leg that may be affected by Quadriceps/Hamstring Muscle Strain.
Figure 25K:
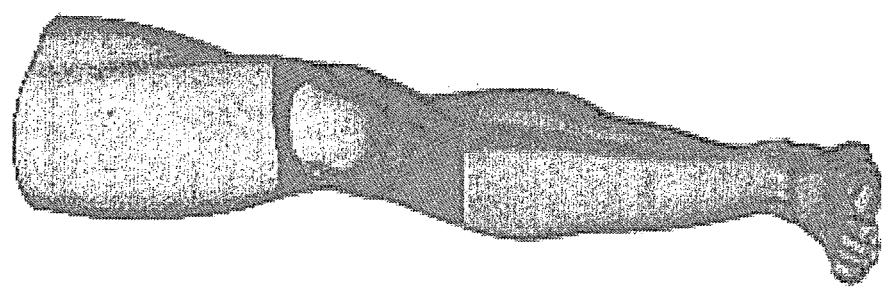
FIG. 25K is an image showing the region of the leg that may be affected by Quadriceps/Hamstring Muscle Strain.

CMP/PFPS Chondromalacia Patella/PatelloFemoral Pain Syndrome (see FIGS. 25C and 25D—Ice with High compression). Chondromalacia patellae (CMP) is referred to as anterior knee pain due to the physical and biomechanical changes. The articular cartilage of the posterior surface of the patella is going though degenerative changes which manifests as a softening, swelling, fraying, and erosion of the hyaline cartilage underlying the patella and sclerosis of underlying bone. PatelloFemoral Pain Syndrome (PFPS) is the most common cause of knee pain in the outpatient setting. It is caused by imbalances in the forces controlling patellar tracking during knee flexion and extension, particularly with overloading of the joint.

Jumper's Knee—Patellar Tendinitis (see FIGS. 25E and 25F—Ice with High Compression) Jumper's knee, also known as patellar tendinitis, is a condition characterized by inflammation of the patellar tendon. This connects the kneecap (patella) to the shin bone (tibia). Jumper's knee weakens the tendon, and if untreated, can lead to tears in the tendon.

Osgood Schlatter—Tibial Tubercle Apophyseal traction injury (see FIGS. 25G and 25H—Ice with High Compression)—Osgood-Schlatter disease is a common cause of knee pain in growing adolescents. It is an inflammation of the area just below the knee where the tendon from the kneecap (patellar tendon) attaches to the shinbone (tibia).

Medial Plica Syndrome (see FIGS. 25I and 25J—Ice with High Compression) Plica syndrome happens when one of the plica is inflamed, usually due to an injury. This often happens in the middle of the kneecap, which is known as medial plica syndrome.

Quadriceps/Hamstring Muscle Strain (see FIGS. 25K and 25L)—Heat/Ice with High Compression in front knee areas and Low Compression behind knee so as to not reduce joint mobility or compress nerves/assenters behind the knee.

Figure 26:
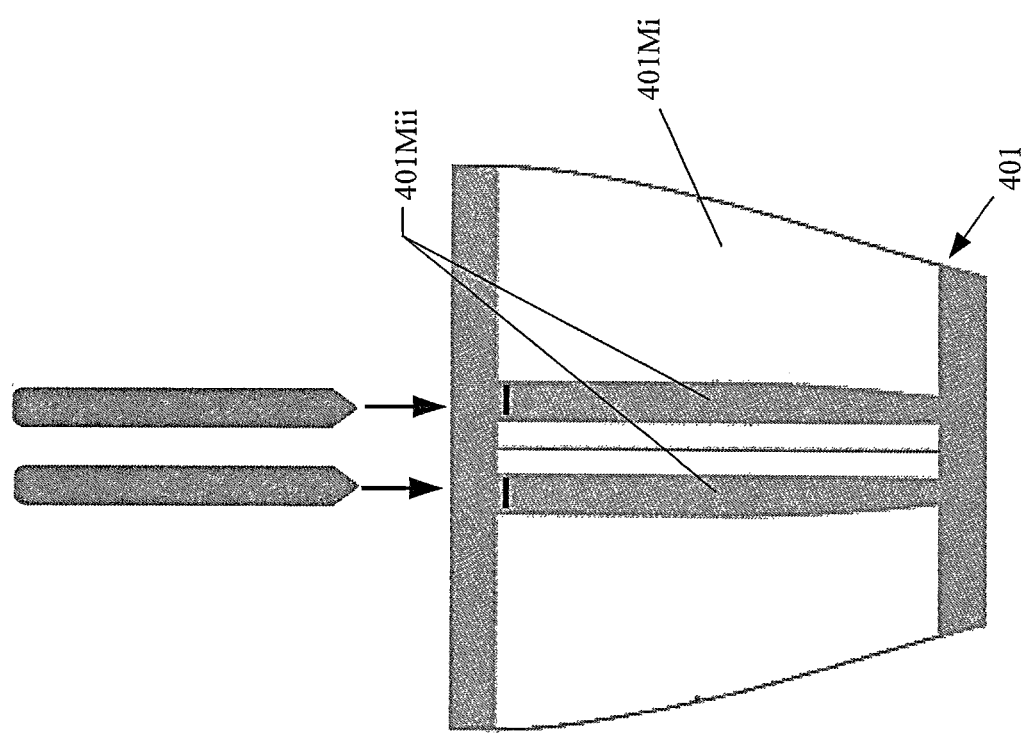
FIG. 26 is a flat pattern for a therapeutic shin compression, being configured to treat shin splints.

FIG. 26 shows a flat pattern for a compression sleeve 401 configured for applying compression and thermal treatments (heating or cooling) to a wearer's shin and surrounding area, and may include: a primary layer of material 401Mi, which may be elastic; a liner that creates particularly positioned and shaped pockets proximate to the shin region to receive one or more custom heat/cold packs through openings; and particularly located layers of high compression material 401Mii that overlie the pocket(s) and may overlie other areas as well (e.g., the bands at the two ends of the sleeve to help retain the sleeve in position at the knee). Two straight regions of the high compression material 401Mii may extend from the upper band of high compression materials to the lowermost band to be positioned over the wearer's shin region (i.e., spaced apart to overlie and extend slightly beyond opposites sides of the tibia), and may have respective pockets underneath each straight region to receive heat/cold packs therein (e.g., D1/D2). In other embodiments, the two straight regions of the high compression material may instead be conjoined to extend completely over the wearer's shin region (i.e., having no small gap therebetween).

The compression sleeve 401 may be used to treat the following injuries:
  Shin Splint: Anterior Tibialis Tendonitis (Use ice) High Compression
  Shin Splint: Posterior Tibialis Tendonitis (Use ice) High Compression
  Calf strain/Termis Leg (medial Gastrocnemius strain) (Heat/Ice) High Compression FIG. 27 and FIG. 28 show a compression sleeve 402 that may be formed the same as compression sleeve 401 but with each of the two straight bands of high compression material 402Mii having portions that extend angularly, whereby the first straight region has two angular extensions (402Mbi and 402Mbii) respectively extending to the upper and lower bands, and the second straight region has two angular extensions (402Mbiii and 402Mbiv) also respectively extending to the upper and lower bands from the opposite side of that region.

Figure 29B:
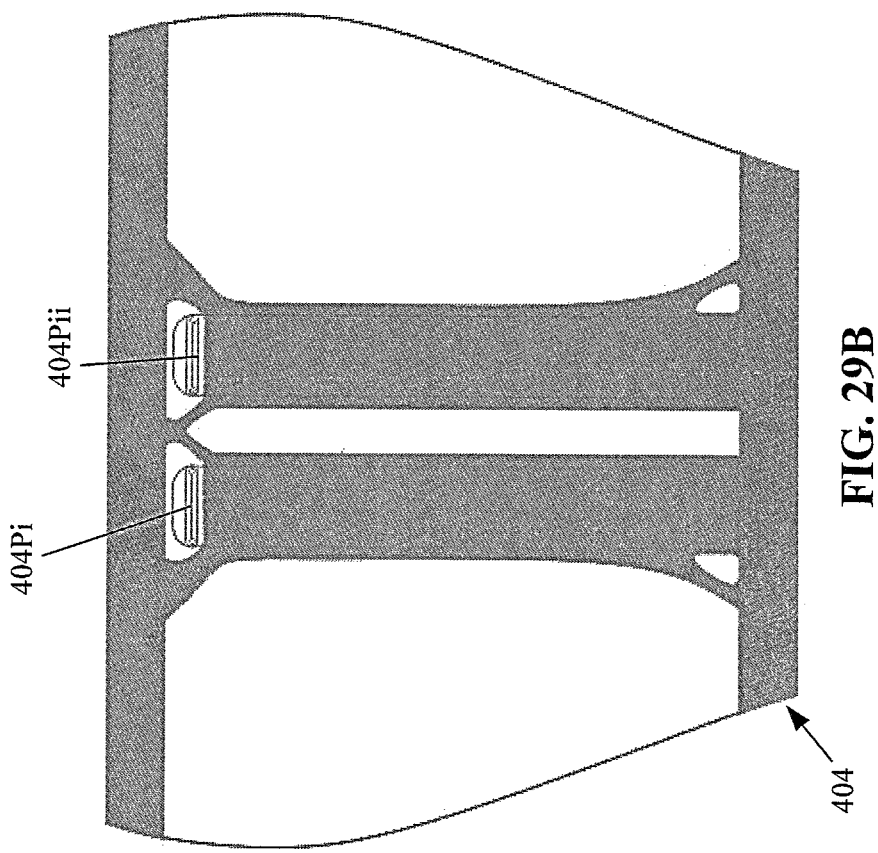
FIG. 29B is the flat pattern of FIG. 29A, but shown with the compression and the heat/cold packs being sized for a large, an extra-large, and a double extra-large wearer.
Figure 29A:
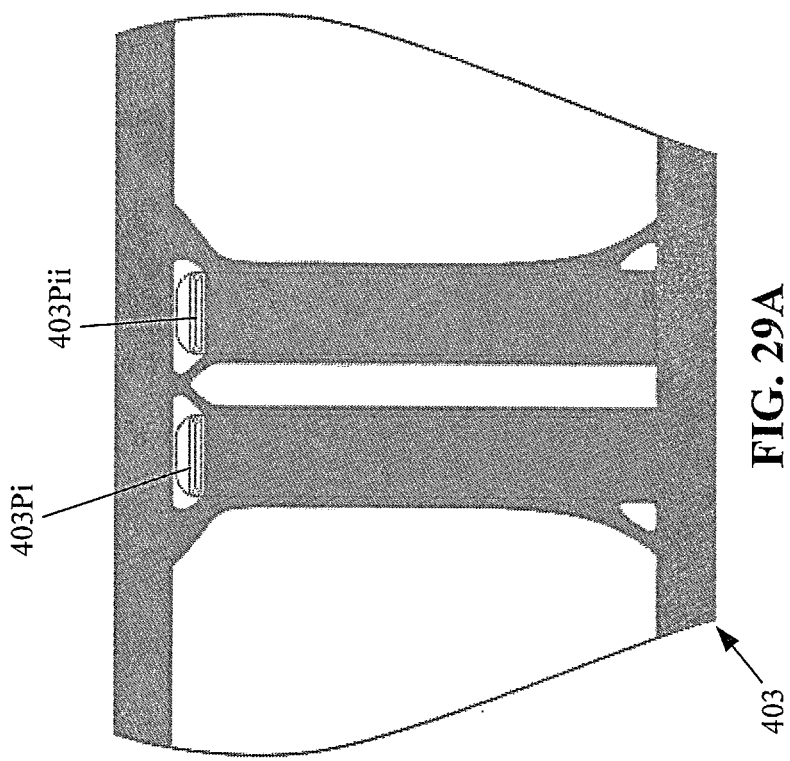
FIG. 29A is a flat pattern for another embodiment of a therapeutic shin compression, with the compression and the heat/cold packs being sized for an extra-small, a small, and a medium sized wearer.
Figure 30A:
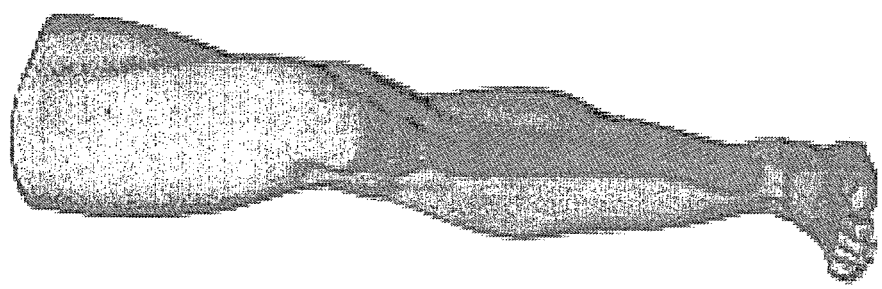
FIG. 30A is an image showing the region of the leg that may be affected by anterior tibialis tendonitis.
Figure 30B:
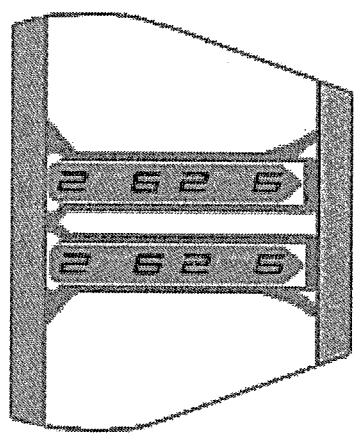
FIG. 30B shows the flat pattern of the therapeutic knee compression of FIGS. 29A-29B to illustrate treatment provided for a leg that may be affected by anterior tibialis tendonitis.
Figure 30D:
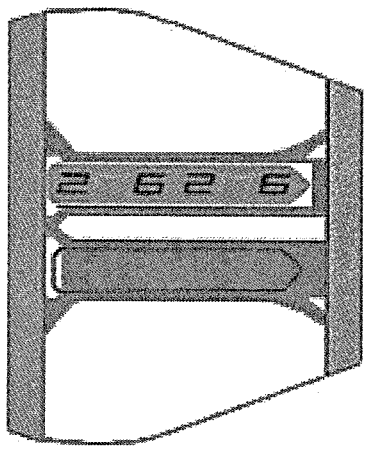
FIG. 30D shows the flat pattern of the therapeutic knee compression of FIGS. 29A-29B to illustrate treatment provided for a leg that may be affected by posterior tibialis tendonitis.
Figure 30C:
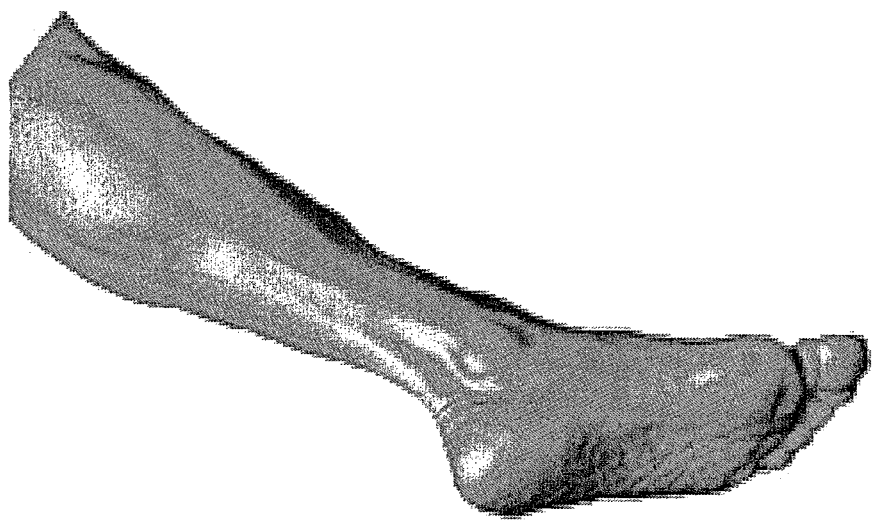
FIG. 30C is an image showing the region of the leg that may be affected by posterior tibialis tendonitis.

FIG. 29A and FIG. 29B respectively illustrate flat patterns for a shin compression sleeve 403 and a shin compression sleeve 404 each of which may be formed similar to the shin compression sleeves 402, but where the shin compression sleeve 403 is proportionally formed to accommodate smaller wearers (e.g., an extra-small, a small, and a medium size leg) and may receive two D1 heat packs into respective pockets through openings 403Pi/403Pii, and where the shin compression sleeve 404 is proportionally formed to accommodate larger wearers (e.g., a large, extra-large, and a double extra-large size leg) and may receive two D2 heat packs into respective pockets through openings 404Pi/404Pii.

Shin splints are common in runners, dancers and military recruits. Medically known as Medial Tibial Stress Syndrome, shin splints often occur in athletes who have recently intensified or changed their training routines. The increased activity overworks the muscles, tendons and bone tissue. The use of the shin compression sleeves 403/404 and the use of "ice" (i.e., a cold pack) within the pockets therein may be injury and/or location specific as follows (see FIGS. 30A-30D):

Shin Splint: Anterior Tibialis Tendonitis (see FIGS. 30A and 30B—Ice with High Compression) Anterior Tibialis Tendonitis is an irritation and swelling of one of the main tendons that lifts the foot up—the anterior tibial tendon which is also known as the tibialis anterior. This condition leads to pain in the front of the ankle or the medial midfoot where it inserts on the bone
  Shin Splint: Posterior Tibialis Tendonitis (see FIGS. 30C and 30D—Ice with High Compression) Posterior tibial tendon dysfunction is one of the most common problems of the foot and ankle. It occurs when the posterior tibial tendon becomes inflamed or torn. As a result, the tendon may not be able to provide stability and support for the arch of the foot, resulting in flatfoot.
  Calf strain/Tennis Leg—Medial Gastrocnemius Strain (Heat/Ice with High Compression) A medial gastrocnemius strain (MGS) is a specific type of injury to the calf muscle in the back of the leg. A muscle strain occurs when the muscle is stretched too far, which causes tears to occur within the muscle. A calf strain occurs when the muscle in the back of the leg sustains this type of injury.

Figure 31:
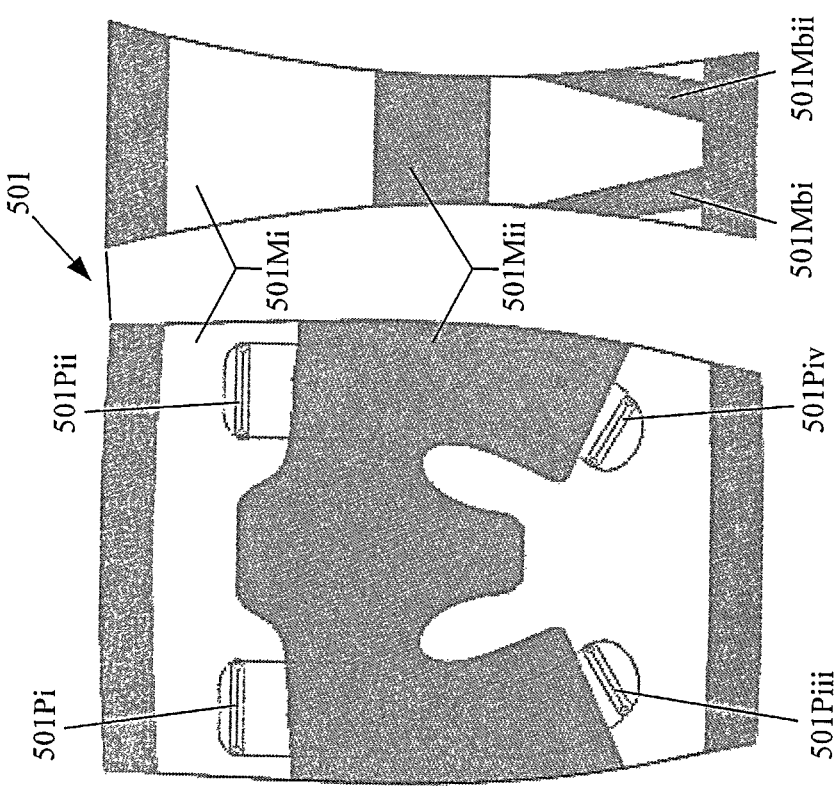
FIG. 31 illustrates flat patterns for an arm compression configured to treat tennis elbow, being configured for an older person, with the compression and the heat/cold packs sized for an extra-small, a small, and a medium sized wearer.

FIG. 31 shows a compression sleeve 501 configured for applying compression and thermal treatments (heating or cooling) to the elbow joint and surrounding area of an older wearer, and may include: a primary layer of material 501Mi, which may be elastic; a liner that creates particularly positioned and shaped pockets that receive one or more custom heat/cold packs through openings; and particularly located layers of high compression material 501Mii that overlie the pocket(s) and form an irregularly shaped central band, and which high compression materials may overlie other areas as well (e.g., the bands at the two ends of the sleeve to help retain the sleeve on the arm in position with respect to the elbow). The irregularly shaped central band of high compression material may have two angular extensions (501Mbi and 501Mbii) that may each extend to one of the end bands.

Figure 32:
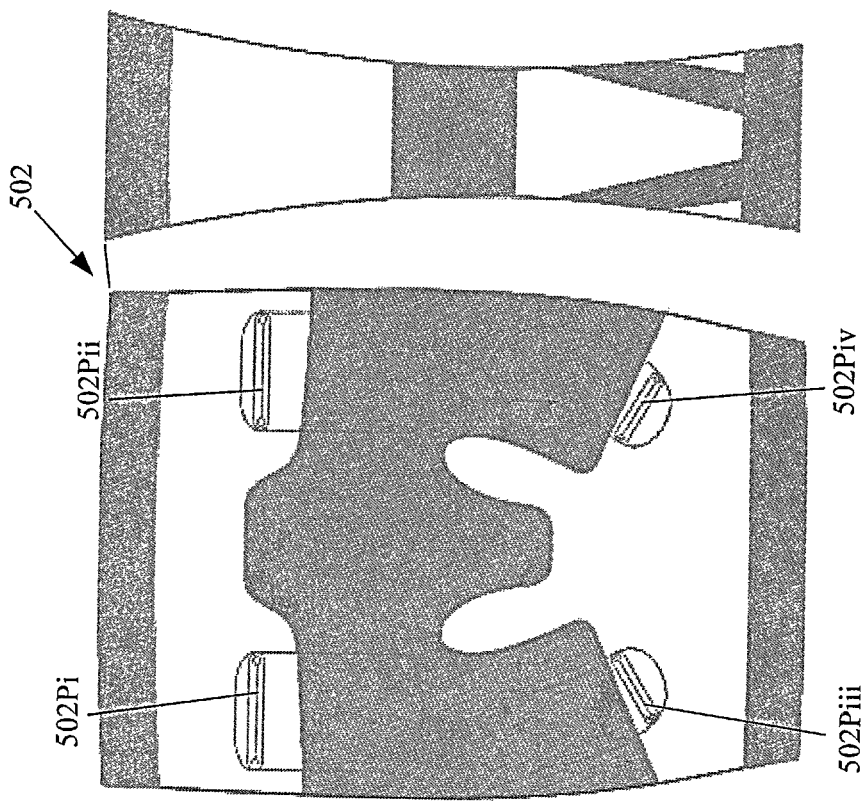
FIG. 32 is the flat pattern of FIG. 31, but shown with the compression and the heat/cold packs being sized for a large, an extra-large, and a double extra-large older wearer.

The compression sleeve 501 may be proportionally formed to accommodate smaller wearers (i.e., an extra-small, a small, and a medium size arm) and may receive two C1 heat packs into respective pockets through openings 501Pi/501Pii, and may receive two F1 heat packs into respective pockets through openings 501Piii/501Piv. The compression sleeve 502 shown in FIG. 32 may be formed the same as sleeve 501, being for an older wearer, but may be proportionally formed to accommodate larger wearers (i.e., a large, extra-large, and a double extra-large size arm) and may receive two C2 heat packs into respective pockets through openings 502Pi/502Pii, and may receive two F1 heat packs into respective pockets through openings 502Piii/502Piv.

Figure 33B:
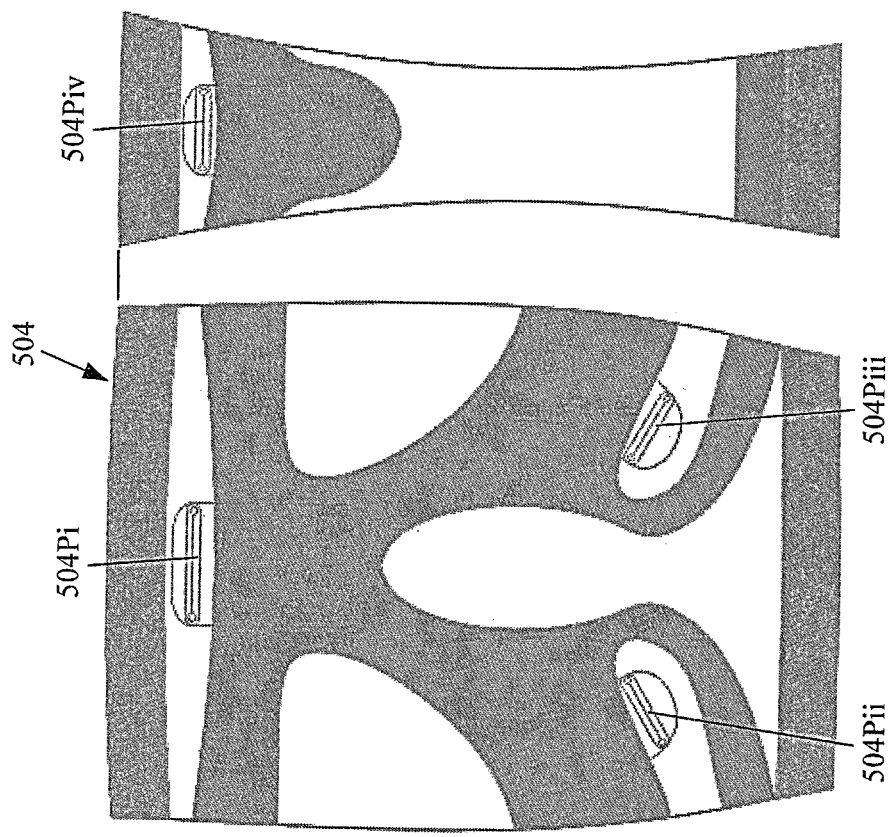
FIG. 33B is the flat pattern of FIG. 33A, but shown with the compression and the heat/cold packs being sized for a large, an extra-large, and a double extra-large younger wearer.
Figure 33A:
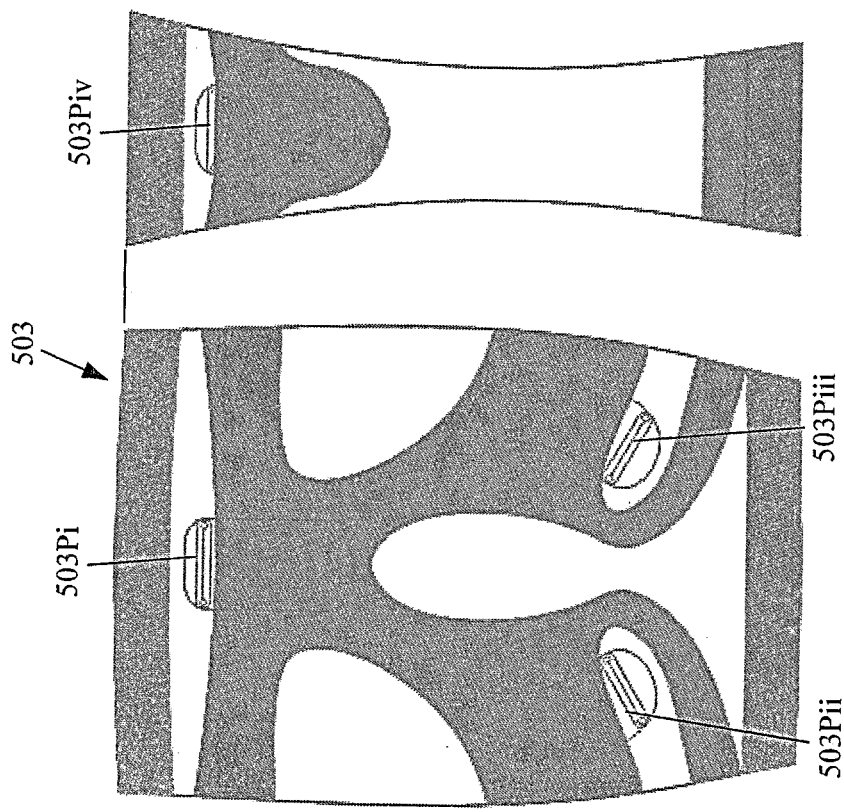
FIG. 33A illustrates flat patterns for an arm compression configured to treat tennis elbow, being configured for a younger person, with the compression and the heat/cold packs sized for an extra-small, a small, and a medium sized wearer.

FIGS. 33A and 33B illustrate compression sleeves 503 and 504 that are configured for applying compression and thermal treatments (heating or cooling) to the elbow joint and surrounding area of a younger wearer, being formed similar to compression sleeves 501 and 502. However, the compression sleeve 503 may be proportionally formed to accommodate smaller wearers (i.e., an extra-small, a small, and a medium size arm) and may receive one C1 heat pack into a pocket through opening 503Pi and may receive two F1 heat packs into respective pockets through openings 503Pii/503Piii, and one C1 heat/cold pack on the rear side through opening 503Piv; while the compression sleeve 504 may be proportionally formed to accommodate larger young wearers (i.e., a large, extra-large, and a double extra-large size arm) and may receive one C2 heat pack into a pocket through opening 504Pi and may receive two F1 heat packs into respective pockets through openings 504Pii/504Piii, and one C2 heat/cold pack on the rear side through opening 504Piv.

The compression sleeves 501/502/503/504 may be used to treat elbow injuries, as follows:
Ulnar Collateral ligament sprain (Throwing Athlete) (Use Ice) High Compression
Distal Biceps Strain Tendonitis (Use Heat/Ice) High Compression
Ulnar Nerve (Cubital Tunnel Syndrome) (Use heat) *Low Compression Behind Elbow
Tennis Elbow: Lateral Epicondylitis (Use ice in circle around lateral epicondyles; Use heat in tapered Oval Down forearm extensor muscle) High compression
Golf Elbow: Medical Epicondyles (Use ice in circle around medical epicondyles; Use heat in tapered Oval Down Forearm Flex or muscles, if needed. Not necessary)
Biceps Strain (Heat/ice) high Compression
Triceps Strain (heat/Ice) high Compression FIG. 34A illustrates a flat pattern for an arm compression sleeve 505 configured to treat golf or tennis elbow injuries, and may be helpful to anyone who has generally injured the elbow, bicep or triceps area from strain, over use, repetitive use or accident. The compression sleeve 505 may be formed similar to compression sleeves 501 and 502, but may be formed to receive one C1 or C2 heat/cold pack into each of a first pair of pockets (where the pocket may be sized in every case to match the particular heat/cold pack size), and may receive two F1 heat/cold packs into a second pair of pockets.

Treatment through the use of the arm compression sleeve 505 and heat or "ice" (i.e., a heat pack or a cold pack) within the pockets therein may be injury and/or location specific as follows (see FIGS. 34B-34G):
Tennis Elbow: Lateral Epicondylitis (see FIGS. 34B and 34D—Use ICE in circle around the lateral epicondyles; Use heat in tapered curved pocket down forearm extensor muscle), and high compression. High compression behind the elbow over the ulnar nerve helps reduce over-extension to approximation of the joint. Tennis elbow is an inflammation of the tendons that join the forearm muscles on the outside of the elbow. The forearm muscles and tendons become damaged from overuse-repeating the same motions again and again. This leads to pain and tenderness on the outside of the elbow.
Golf Elbow: Medial Epicondylitis (see FIGS. 34C and 34D—Use ICE in circle around medial epicondyles; Use heat in tapered curve down Forearm Flex or muscles, if needed but not necessary), and high compression. Golfer's elbow is a condition that causes pain where the tendons of the forearm muscles attach to the bony bump on the inside of the elbow. The pain might spread into the forearm and wrist. Golfer's elbow (inside elbow) is similar to tennis elbow which occurs on the outside of the elbow.
Biceps Strain: Heat/Ice with High Compression (see FIGS. 34E and 34G). There are a variety of causes for a bicep tear or strain including:
Constant overuse-sports that require repetitive movement on the bicep in the shoulder or elbow can cause a bicep tear or strain; and
Acute injury-moving or twisting your elbow in an unfamiliar way can cause a bicep tear or strain, for example, falling on an outstretched arm.
Triceps Strain: Heat/Ice with High Compression (see FIGS. 34F and 34G). A triceps strain typically occurs due to a sudden, forceful contraction (or less commonly, a stretch) of the triceps muscle; during heavy pushing or straightening of the elbow against resistance (such as performing explosive dips, pushups, bench presses, cable triceps exercises etc.). At the gym, the use of heavy weights, quick movements may increase the likelihood of the condition occurring; may also occur in sports involving throwing (such as cricket or baseball) or sport involving heavy falls or blocking. Triceps strain occurs more commonly in the older deconditioned athlete, especially following an inadequate warm-up.

FIG. 34H illustrates a flat pattern for an arm compression sleeve 506 configured to treat golf or tennis elbow injuries, and may be helpful to anyone who has generally injured the elbow, bicep or triceps area from strain, over use, repetitive use or accident. The compression sleeve 506 may be formed similar to compression sleeves 501 and 502, but may be formed to receive one C1 or C2 heat/cold pack into each of a first pocket and two F1 heat/cold packs into a pair of pockets all being on the medial side, and may receive one C1 or C2 heat/cold pack into a pocket on the lateral side.

Treatment through the use of the arm compression sleeve 506 and heat or "ice" (i.e., a heat pack or a cold pack) within the pockets therein may be injury and/or location specific as follows (see FIGS. 34I-34N):

Ulnar Collateral Ligament Sprain—Throwing Athlete. (See FIG. 34I-34J—Use Ice with High Compression*). An ulnar collateral ligament injury can range from a mild stretch to a full tear. An ulnar collateral ligament tear is usually the result of a sports injury that involves repetitive overuse associated with pitching or throwing. A first-degree sprain occurs when the ligament is strained without it becoming stretched.

Distal Biceps Strain Tendinitis (See FIG. 34K-34L—Use Heat/Ice with High Compression*). Tendinosis of the biceps tendon can be painless or it can cause dull or sharp pain in the area of the tendon just past the front of the elbow in the forearm. In some cases, tendinosis can lead to partial tendon tears or complete tendon rupture. Biceps tendinosis is one of several possible causes of pain around the elbow.

Ulnar Nerve—Cubital Tunnel Syndrome. (See FIG. 34M-34N—Use HEAT with *Low Compression Behind Elbow). Cubital Tunnel Syndrome is a condition that involves pressure or stretching of the ulnar nerve (also known as the "funny bone" nerve), which can cause numbness or tingling in the ring and small fingers, pain in the forearm, and/or weakness in the hand.

Golf Elbow: Medial Epicondylitis (Use ICE in circle around medial epicondyles; Use heat in tapered curve down Forearm Flex or muscles, if needed but not necessary.) High compression*. Golfer's elbow is a condition that causes pain where the tendons of the forearm muscles attach to the bony bump on the inside of the elbow. The pain might spread into the forearm and wrist. Golfer's elbow (inside elbow) is similar to tennis elbow which occurs on the outside of the elbow.

High Compression behind Elbow over ulnar nerve helps reduce over-extension to approximation of the joint.

Low Compression is located behind elbow so as to not impede joint movement.

FIG. 34O illustrates a flat pattern for a full arm compression sleeve 507 configured to generally treat middle age to older individuals whose muscle pain may also involve connective tissue. Arm compression sleeve 507 is configured to treat injury or strain to the upper or lower arm and elbow regions. Being specifically focused on treatment for the larger tendons, muscle groups and connective tissue of the arm, the compression is beneficial to any pain or injury that may radiate from upper to lower arm and elbow or vice versa as well. The arm compression sleeve 507 may be formed similar to compression sleeves 501 and 502, but may be longer and have a different arrangement for the pockets. The arm compression sleeve 507 may be formed to receive a C1 or C2 heat/cold pack into each of a first pair of pockets on the medial side for the upper arm, two F1 heat/cold packs into a second pair of pockets on the medial side, and a C1/C2 heat/cold pack into a pocket on the medial side for the lower arm. There may also be an additional pocket on the upper arm that may receive a C1 heat/cold pack.

Conditions treated through the use of the arm compression sleeve 507 and heat or "ice" (i.e., a heat pack or a cold pack) within the pockets therein may be injury and/or location specific as follows (see FIGS. 34P-34U):

Supports distal biceps and triceps to prevent "traction overload injury" when arm decelerates in throwing sports (i.e. the follow through). See FIGS. 34P-34Q. High compression over biceps reduces risk of distal biceps tendon rupture. A distal biceps tendon rupture is a tear of the tendon from the forearm bone (radius). Ruptures of the distal bicep tendon are almost always caused by a sudden injury to the elbow. This can happen when lifting objects that are too heavy, resulting in the elbow being forced straight when the bicep is under tension. Provides increased stability in back of elbow to reduce stress with full elbow extension. Larger area flexor/exterior muscle groups (older individuals more likely to get tennis and golfer's elbow)

Supports medial and lateral forearm muscle groups (see FIGS. 34R-34S) to decrease Varus and Valgus stress. A Varus deformity is an excessive inward angulation (medial angulation, that is, towards the body's midline) of the distal segment of a bone or joint. The opposite of Varus is called Valgus (lateral angulation). The terms Varus and Valgus always refer to the direction that the distal segment of the joint points.

Wrist area compression (see FIGS. 34T-34U) provides pressure to prevent "bowstringing" of flexor tendons during sports. Fingers and wrist were "made to flex"—but NOT at the same time. Although the long flexor tendons possess a natural tendency to bow string, and even though the flexor retinaculum (transverse carpal ligament, TCL) functions to prevent bowstringing, the mechanism becomes overused with constant finger flexion accompanied by wrist flexion. This combination feels unnatural and typically only occurs when specific job tasks require the combination to hold or assemble an object. The pressure exerted on the tendons as they glide and rub across the distal edge of the TCL results in inflammation leading to swelling. The ensuing pressure in the carpal tunnel entraps the median nerve yielding carpal tunnel syndrome. Additionally there is direct pressure on the median nerve as it is sandwiched between the flexor tendons and the TCL.

High compression over biceps reduces risk of distal biceps tendon rupture. A distal biceps tendon rupture is a tear of the tendon from the forearm bone (radius). Ruptures of the distal bicep tendon are almost always caused by a sudden injury to the elbow. This can happen when lifting objects that are too heavy, resulting in the elbow being forced straight when the bicep is under tension. Provides increased stability in back of elbow to reduce stress with full elbow extension. Larger area flexor/exterior muscle groups (older individuals more likely to get tennis and golfer's elbow).

FIG. 34Oi illustrates a flat pattern for a full arm compression 507' configured to generally treat middle age to older individuals whose muscle pain may also involve connective tissue, being formed the same as the arm compression 507 shown in FIG. 34O, but which includes one additional pocket to receive an additional C1/C2 heat/cold pack to be located on the medial side near the upper arm. Both of the full arm compressions 507 and 507', as well as all of the other compressions, may have an opening into each pocket as described hereinabove.

FIG. 34V illustrates a flat pattern for a full arm compression sleeve 508 configured to generally treat younger to middle age individuals with a muscle injury or strain to the upper or lower arm and elbow regions. Being specifically focused on treatment for the larger tendon and muscle groups of the arm, the compression 508 is beneficial to any pain or injury that may radiate from upper to lower arm or vice versa as well. The arm compression sleeve 508 may be formed similar to compression sleeve 507, but may have a slightly different arrangement for the pockets. The arm compression sleeve 508 may be formed to receive a C1 or C2 heat/cold pack into each of a first pair of pockets on the medial side for the upper arm, two F1 heat/cold packs into a second pair of pockets on the medial side, and a C1 or C2 heat/cold pack into a pocket on the medial side for the lower arm, the same as compression sleeve 507. However, arm compression sleeve 508 may also be formed to receive one C1 or C2 heat/cold pack into a pocket on the lateral side.

Conditions treated through the use of the arm compression sleeve 508 and heat or "ice" (i.e., a heat pack or a cold pack) within the pockets therein may be injury and/or location specific as shown in FIGS. 34W-34ZZZ, and may include: supporting distal biceps and triceps to prevent "traction overload injury"; supporting medial and lateral forearm muscle groups (see FIGS. 34R-34S) to decrease Varus and Valgus stress; and providing compression pressure to the wrist area to prevent "bowstringing" of flexor tendons during sports.

FIG. 35 and FIG. 36 show front and rear views of a short-length pants compression garment 601 configured for treating muscles of a younger wearer (e.g., the quadriceps, hip flexor muscles, the high adductor muscles, the high hamstring, etc.) with openings formed to receive heat/cold packs into pockets (FIGS. 37-42) therein to apply heat and/or cold therapy under compression, shown after being donned by a wearer. The short-length pants compression garment 601 may include: a primary layer of material 601Mi, which may be elastic; a liner that creates particularly positioned and shaped pockets that receive one or more custom heat/cold packs through openings; and particularly located layers of high compression material 601Mii that overlie the pockets and which high compression materials may overlie other areas as well (e.g., the regions on the inside of the thighs). The waist band and bands at the lower portion of the leg regions may also be formed of the high compression material 601Mii.

FIG. 43 shows a flat pattern for a short-length pants compression garment 602 that may be formed similar to the compression garment 601, being configured for a younger wearer and having: a primary layer of material 602Mi, which may be elastic; a liner that creates particularly positioned and shaped pockets that receive one or more custom heat/cold packs through openings; and particularly located layers of high compression material 602Mii that overlie the pockets. In addition, the high compression material 602Mii that overlies each of the pockets of the short-length pants compression garment 602 may have angular extensions that connect to form a central band of high compression material around the circumference of the left thigh and also the right thigh, as seen in FIG. 43. The compression pants 602 may be proportionally formed to accommodate smaller wearers (i.e., an extra-small, a small, and a medium size person) and may receive one B1 heat pack into each of the four pockets through openings 602Pi/602Pii/602Piii/602Piv, and where the short length pants 602 may be proportionally formed to accommodate larger wearers (i.e., a large, extra-large, and a double extra-large size person) and may receive one B2 heat pack into each of the four pockets through openings 602Pi/602Pii/602Piii/602Piv. FIG. 43A shows a second embodiment, being a short-length pants compression garment 602A that may be formed the same as compression garment 602, but is configured for a younger wearer, and which has two additional pockets located in the groin area that may each receive an E1 heat/cold pack therein through openings 602Pv/602Pvi.

Conditions treated through the use of the short-length pants compression garments 602/602A using heat or "ice" (i.e., a heat pack or a cold pack) within the pockets therein may be injury and/or location specific:

Front High Quad/Hip Flexor/Pointer. (see FIGS. 43B and 43C—Use HEAT/ICE on front of thigh, quad area for injury or pain; use compression only for hip flexor/pointer areas). The hip flexors are several muscles that bring the legs and trunk together in a flexion movement. They allow movement of the leg or knee up towards the torso, as well as to bending the torso forward at the hip. The hip flexor muscles can be torn or strained through sudden movements or falls.

Front High Adductor Muscles (Origin at groin by pubic tubercle). (see FIGS. 43D and 43E—Use HEAT/ICE on all areas for symptoms, injury or pain.) An adductor muscle strain is an acute injury to the groin muscles on the medial aspect (inside) of the thigh. Although several different muscles can be injured, the most common are the Adductor Longus, Medius, and Magnus, and the Gracilis.

Back High Hamstring (Origin by ischial tuberosity). (see FIGS. 43F and 43G—Use HEAT/ICE on back of thigh, hamstring area for injury or pain) The ischial tuberosity (or tuberosity of the ischium, tuber ischiadicum), also known informally as the sit bones, or as a pair—the sitting bones—is a large swelling posteriorly on the superior ramus of the ischium. It marks the lateral boundary of the pelvic outlet.

FIG. 44 and FIG. 45 show front and rear views of a short-length pants compression garment 603 configured for treating joints of an older wearer (e.g., greater trochanteric bursitis, hip osteoarthritis, etc.), with openings formed to receive heat/cold packs into pockets therein (FIGS. 46-51) to apply heat and/or cold therapy under compression, shown after being donned by a wearer. The short-length pants compression garment 603 may include: a primary layer of material 603Mi, which may be elastic; a liner that creates particularly positioned and shaped pockets that receive one or more custom heat/cold packs through openings; and particularly located layers of high compression material 603Mii that overlie the pockets and which high compression materials may overlie other areas as well (e.g., the regions on the inside of the thighs). The waist band and bands at the lower portion of the leg regions may also be formed of the high compression material 603Mii.

FIG. 52 shows a flat pattern for a short-length pants compression garment 604 that may be formed similar to the compression garment 603, being configured for an older wearer and having: a primary layer of material 604Mi, which may be elastic; a liner that creates particularly positioned and shaped pockets that receive one or more custom heat/cold packs through openings; and particularly located layers of high compression material 604Mii that overlie the pockets. The waist band and the bands at the lower portion of the leg regions may also be formed of the high compression material 604Mii. In addition, the high compression material 604Mii that overlies each of the pockets of the short-length pants compression garment 604 may have angular extensions that connect to the waist band and the bands at the lower portion of the leg regions, as seen in FIG. 52. The compression garment 604 may be proportionally formed to accommodate smaller wearers (i.e., an extra-small, a small, and a medium size person) and may receive one B1 heat pack into each of the two upper pockets through openings 604Pi/604Pii, and may receive one E1 heat pack into each of the two lower pockets through openings 602Piii/602Piv. The compression garment 604 may also be proportionally formed to accommodate larger wearers (i.e., a large, extra-large, and a double extra-large size person) and being so formed may receive one B1 or B2 heat pack into each of the two upper pockets through openings 604Pi/604Pii, and may receive one E1 heat pack into each of the two lower pockets through openings 602Piii/602Piv. FIG. 52A shows another flat pattern for a short-length pants compression garment 604A that is formed the same as compression garment 604, but which also has two additional pockets located in the groin area that may each receive an E1 heat/cold pack therein through openings 604Piii/604Piv. Some conditions that may be treated through the use of the short-length pants compression garments 604A using heat or "ice" are shown in FIGS. 52B-52E.

FIG. 53 shows a flat pattern for a mid-length pants compression garment 701 configured for treating muscles of a younger wearer (e.g., quad muscle, adductor magnus and longus, hamstring muscle belly, gastrocnemius, etc.), with openings formed to receive heat/cold packs into pockets therein to apply heat and/or cold therapy under compression, shown after being donned by a wearer. The mid-length pants compression garment 701 may include: a primary layer of material 701Mi, which may be elastic; a liner that creates particularly positioned and shaped pockets that receive one or more custom heat/cold packs through openings; and particularly located layers of high compression material 701Mii that overlie the pockets. In addition, the high compression material 701Mii that overlies each of the pockets of the mid-length pants compression garment 701 may have angular extensions that connect to form two central bands of high compression material around the circumference of the left thigh and also the right thigh, as seen in FIG. 53. The waist band and bands at the lower portion of the leg regions may also be formed of the high compression material 701Mii. The compression sleeve 701 may be formed to receive a B1 or B2 heat pack into each of four pockets through openings 701Pi/701Pii/701Piii/701Piv, and may receive a B2 heat pack into each of two pockets through openings 701Pv/701Pvi. FIG. 53A is a flat pattern of another mid-length pants compression garment 701A that is configured for a younger wearer, being formed the same as the flat pattern in FIG. 53, but with two additional pockets located at the left and right groin areas that may each receive an E1 or E2 heat/cold pack therein through respective openings 701Pvii and 701Pviii. Some conditions that may be treated through the use of the short-length pants compression garment 701A using heat or "ice" are shown in FIGS. 53B-53I.

FIG. 54 shows a flat pattern for a mid-length pants compression garment 702 that may be formed similar to the compression garment 701, but is configured for an older wearer and has: a primary layer of material 702Mi, which may be elastic; a liner that creates particularly positioned and shaped pockets that receive one or more custom heat/cold packs through openings; and particularly located layers of high compression material 702Mii that overlie the pockets. In addition, the high compression material 702Mii that overlies each of the pockets of the mid-length pants compression garment 702 may have angular extensions that connect to form a pair of central bands of high compression material around the circumference of the left thigh and also the right thigh, as seen in FIG. 54. The mid-length pants compression garment 702 may be formed to accommodate smaller wearers (i.e., an extra-small, a small, and a medium size person) and may receive one B1 heat pack into each of the two pockets through respective openings 702Pi and 702Pii, and one A1 heat/cold pack into each of two other pockets through respective openings 702Piii/702Piv. Where the mid-length pants compression garment 702 may be proportionally formed to accommodate larger wearers (i.e., a large, extra-large, and a double extra-large size person) it may instead receive one B2 heat pack into each of the two quad pockets through respective openings 702Pi/702Pii.

FIG. 54A is a flat pattern of another mid-length pants compression garment 703 that is configured for an older wearer, being formed similar to the flat pattern in FIG. 54, having two pockets for heat/cold packs for the left and right quads (i.e., being received through openings 703Pi/703Pii), different shaped pockets located at each calf area to receive an E1 or E2 heat/cold pack through openings 703Pvii and 703Pviii, with two additional pockets for heat/cold packs for the left and right hips to receive a B1 or B2 heat/cold pack through openings 703Piii and 703Piv, and two additional pockets located at the left and right groin areas to receive an or E1 an E2 heat/cold pack through openings 703Pv and 703Pvi. Some conditions that may be treated through the use of the mid-length pants compression garments 702 and 702A using heat or "ice" are shown in FIGS. 54B-54K.

FIG. 55 is a flat pattern of another compression garment configured as full-length pants 801 for use by a younger wearer, with openings formed to receive heat/cold packs into pockets therein to apply heat and/or cold therapy under compression. The full-length pants compression 801 may be formed with a primary layer of material 801Mi, which may be elastic, a liner that creates the particularly shaped pockets, and the particularly located layer or layers of higher compression material 801Mii (shown shaded in FIG. 55). The full-length pants compression garment 801 may have: left and right side pockets that each receive one B1 or B2 heat/cold pack through openings 801Pi, 801Pii, 801Piii, and 801Piv, which are positioned then over the quad and hamstring muscles; left and right side pockets that each receive one B1 or B2 heat/cold pack through openings 801Pv and 801Pvi, which are positioned over the calf muscles; left and right side pockets that each receive one E1 or E2 heat/cold pack through openings 801Pvii and 801Pviii, which are positioned over the groin muscles; and left and right side pockets that each receive one E1 or E2 heat/cold pack through openings 801Pix and 801Px, which are positioned over the Achilles tendon. Some conditions that may be treated through the use of the full-length pants compression garment 801 using heat or "ice" are shown in FIGS. 55A-55J.

FIG. 56 is a flat pattern of another compression garment configured as full-length pants 901 for use by an older wearer, with openings formed to receive heat/cold packs into pockets therein to apply heat and/or cold therapy under compression. The full-length pants compression 901 may be formed with a primary layer of material 901Mi, which may be elastic, a liner that creates the particularly shaped pockets, and the particularly located layer or layers of higher compression material 901Mii (shown shaded in FIG. 56). The full-length pants compression garment 901 may have: left and right side pockets that each receive one B1 or B2 heat/cold pack through openings 901Piii, and 901Piv, which are positioned then over the hip joints; left and right side pockets that each receive one E1 or E2 heat/cold pack through openings 901Pvii and 901Pviii, which are positioned over the groin muscles; left and right side pockets that each receive one B1 or B2 heat/cold pack through openings 901Pi and 901Pii, which are positioned over the quad muscles; and left and right side pockets that each receive one E1 or E2 heat/cold pack through openings 901Pv and 901Pvi, which are positioned over the Achilles tendon. Some conditions that may be treated through the use of the full-length pants compression garment 901 using heat or "ice" are shown in FIGS. 56A-56L.

FIG. 57 is a flat pattern of a full-leg compression garment 1001 configured for use by a younger wearer, with openings formed to receive heat/cold packs into pockets therein to apply heat and/or cold therapy under compression. The full-leg compression 1001 may be formed with a primary layer of material 1001Mi, which may be elastic, a liner that creates the particularly shaped pockets, and the particularly located layer or layers of higher compression material 1001Mii (shown shaded in FIG. 57) which are particularly shaped to be able to apply a sufficient amount of pressure onto each of the heat/cold packs. The full-leg compression garment 1001 may have: a pair of pockets that each receive one B1 or B2 heat/cold pack through openings 1001Pi and 1001Pii, which are then positioned over the quad and hamstring muscles respectively; a pocket that receives one B1 or B2 heat/cold pack through opening 1001Piii, which is to be positioned over the calf muscle; and one pocket that receives an E1 or E2 heat/cold pack through opening 1001Piv, which is to be positioned over the Achilles tendon. Some conditions that may be treated through the use of the full-leg compression garment 1001 using heat or "ice" are shown in FIGS. 57A-57J.

FIG. 58 is a flat pattern of a full-leg compression garment 1101 configured for use by an older wearer, with openings formed to receive heat/cold packs into pockets therein to apply heat and/or cold therapy under compression. The full-leg compression 1101 may be formed with a primary layer of material 1101Mi, which may be elastic, a liner that creates the particularly shaped pockets, and the particularly located layer or layers of higher compression material 1101Mii (shown shaded in FIG. 58) which are particularly shaped to be able to apply a sufficient amount of pressure onto each of the heat/cold packs. The full-leg compression garment 1101 may have: a pocket that receives a B1 or B2 heat/cold pack through opening 1101Pi, which is then positioned over the quad muscle; one pocket that receives an E1 or E2 heat/cold pack through opening 1101Pii, which is to be positioned over the Achilles tendon; and a pocket that receives one E1 or E2 heat/cold pack through opening 1101Piii, which is to be positioned over the adjacent groin muscle. Some conditions that may be treated through the use of the full-leg compression garment 1101 using heat or "ice" are shown in FIGS. 58A-58J.

FIG. 59 is a flat pattern of a thigh compression garment 1201, with openings formed to receive heat/cold packs into pockets therein to apply heat and/or cold therapy under compression. The thigh compression 1201 may be formed with a primary layer of material 1201Mi, which may be elastic, a liner that creates the particularly shaped pockets, and the particularly located layer or layers of higher compression material 1201Mii (shown shaded in FIG. 59) which are particularly shaped to be able to apply a sufficient amount of pressure onto each of the heat/cold packs. The thigh compression garment 1201 may have: a pair of pockets that each receive a C1 or C2 heat/cold pack through openings 1201Pi and 1201Pii, which are then positioned over portions of the quad muscle; one pocket that receives an E1 or E2 heat/cold pack through opening 1201Piii, which is to be positioned over the adjacent groin muscle; and a pocket that receives one B1 or B2 heat/cold pack through opening 1201Piv, which is to be positioned over the hamstring muscle. Some conditions that may be treated through the use of the thigh compression garment 1201 using heat or "ice" are shown in FIGS. 59A-59F.

FIG. 60 is a flat pattern of a calf compression garment 1301, with openings formed to receive heat/cold packs into pockets therein to apply heat and/or cold therapy under compression. The calf compression 1301 may be formed with a primary layer of material 1301Mi, which may be elastic, a liner that creates the particularly shaped pockets, and the particularly located layer or layers of higher compression material 1301Mii (shown shaded in FIG. 60) which are particularly shaped to be able to apply a sufficient amount of pressure onto each of the heat/cold packs. The calf compression garment 1301 may have: a pocket that receives an A1 or A2 heat/cold pack through opening 1301Pi, and a pocket that receives a C1 or C2 heat/cold pack through opening 1301Pii, which heat/cold packs are to be positioned over particular portions of the calf muscle. Some conditions that may be treated through the use of the calf compression garment 1301 using heat or "ice" are shown in FIGS. 60A-60B.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A knee brace comprising: a sleeve, said sleeve comprising: a primary layer formed of an elastic material configured to apply a first level of compression; said sleeve formed to fit on at least a portion of a leg of a wearer to cover the knee, and to extend a first distance beyond the knee onto the thigh region of the wearer to a first end, and to extend a second distance away from the knee onto at least a portion of the calf region of the wearer to a second end; a first opening and a first pocket formed in said sleeve, said first opening and said first pocket configured to receive a first correspondingly sized and shaped thermal pack, said first pocket comprising an arcuate shape having a first curved side and a second curved side, said first opening and said first pocket configured to be positioned on the anterior of the leg, whereat said first curved side is positioned in proximity to a first portion of the patella when said knee brace is worn, and said second curved side is positioned distally from the first portion of the patella, when said knee brace is worn; a second opening and a second pocket formed in said sleeve, said second opening and said second pocket configured to receive a second thermal pack being correspondingly sized and shaped, said second pocket comprising an arcuate shape having a first curved side and a second curved side, said second opening and said second pocket configured to be positioned on the anterior of the leg, whereat said first curved side of said second pocket is positioned in proximity to a second portion of the patella when said knee brace is worn, and said second curved side of said second pocket is positioned distally from the second portion of the patella, when said knee brace is worn; wherein said sleeve further comprises: a patella encircling band formed of one or more layers of high compression material and configured to completely and continuously encircle the patella, when said knee brace is worn; wherein at least a portion of said patella encircling band is configured to overlie and to apply a second level of compression to each of said first pocket and said second pocket, said second level of compression being greater than the first level of compression; an upper leg encircling band formed of one or more layers of the high compression material and configured to completely encircle a portion of the thigh of the wearer, when said knee brace is worn; a lower leg encircling band formed of one or more layers of the high compression material and configured to completely encircle a portion of the calf region of the wearer, when said knee brace is worn; wherein an upper portion of said patella encircling band is coextensive with a portion of said upper leg encircling band; and wherein a lower portion of said patella encircling band is coextensive with a portion of said lower leg encircling band.

2. The knee brace according to claim 1, further comprising: a third opening and a third pocket formed in said sleeve, said third opening and said third pocket configured to receive a third thermal pack being correspondingly sized and shaped, said third pocket being substantially straight and oriented in an axial direction of the leg to extend on the anterior of the leg towards the patella when said knee brace is worn, with a width of said third pocket being formed to fit between an end of each of said first and second pockets, to surround a third portion of the patella when said knee brace is worn.

3. The knee brace according to claim 2, wherein said first pocket, said second pocket, and said third pocket are configured to surround at least eighty percent of a periphery of the patella.

4. The knee brace according to claim 3, further comprising: a fourth opening and a fourth pocket formed in said sleeve, said fourth opening and said fourth pocket configured to receive a fourth thermal pack being correspondingly sized and shaped, said fourth pocket being substantially straight and oriented to extend in an axial direction on the posterior of the upper leg towards the kneepit when said knee brace is worn; and a fifth opening and a fifth pocket formed in said sleeve, said fifth opening and said fifth pocket configured to receive a fifth thermal pack being correspondingly sized and shaped, said fifth pocket being substantially straight and oriented to extend in an axial direction on the posterior of the lower leg towards the kneepit when said knee brace is worn.

5. The knee brace according to claim 4,
wherein said one or more layers of high compression material are configured to releasably seal said first opening and completely enclose the thermal pack in said first pocket after the thermal pack is fully inserted into said first pocket through said first opening;
wherein said one or more layers of high compression material are configured to releasably seal said second opening and completely enclose the thermal pack in said second pocket after the thermal pack is fully inserted into said second pocket through said second opening; and
wherein said one or more layers of high compression material are configured to releasably seal said third opening and completely enclose the thermal pack in said third pocket after the thermal pack is fully inserted into said third pocket through said third opening.

6. The knee brace according to claim 5,
wherein a profile shape of an interior of each of said first and second pockets comprises a curved gonfalon shape; and
wherein a profile shape of an interior of said third, fourth, and fifth pockets comprises a straight gonfalon shape.

7. The knee brace according to claim 6,
wherein said first curved side of each of said first pocket and said second pocket has a radius of curvature of about 83 mm.

8. The knee brace according to claim 7,
wherein said first curved side of each of said first pocket and said second pocket has a radius of curvature of between 83 mm and 114 mm.

* * * * *